US012668592B2

(12) United States Patent
Lim et al.

(10) Patent No.: US 12,668,592 B2
(45) Date of Patent: Jun. 30, 2026

(54) ORGANIC LIGHT EMITTING DIODE AND ORGANIC LIGHT EMITTING DEVICE INCLUDING THE SAME

(71) Applicant: LG DISPLAY CO., LTD., Seoul (KR)

(72) Inventors: Gi Hwan Lim, Paju-si (KR); Tae Ryang Hong, Paju-si (KR); Jun Yun Kim, Paju-si (KR)

(73) Assignee: LG Display Co., Ltd., Seoul (KR)

(*) Notice: Subject to any disclaimer, the term of this patent is extended or adjusted under 35 U.S.C. 154(b) by 1015 days.

(21) Appl. No.: 17/782,967

(22) PCT Filed: Sep. 7, 2021

(86) PCT No.: PCT/KR2021/012133
§ 371 (c)(1),
(2) Date: Jun. 6, 2022

(87) PCT Pub. No.: WO2022/065750
PCT Pub. Date: Mar. 31, 2022

(65) Prior Publication Data

US 2023/0100457 A1 Mar. 30, 2023

(30) Foreign Application Priority Data

Sep. 28, 2020 (KR) ........................ 10-2020-0125653

(51) Int. Cl.
*H01L 51/50* (2006.01)
*C07D 471/04* (2006.01)
(Continued)

(52) U.S. Cl.
CPC ......... *C07D 471/04* (2013.01); *C07D 487/04* (2013.01); *H10K 50/125* (2023.02);
(Continued)

(58) Field of Classification Search
None
See application file for complete search history.

(56) References Cited

U.S. PATENT DOCUMENTS 10,510,966 B2 12/2019 Jeon et al.
10,566,561 B2 2/2020 Kim et al.
(Continued)

FOREIGN PATENT DOCUMENTS

CN 109994628 A 7/2019
KR 10-2017-0136256 A 12/2017
(Continued)

OTHER PUBLICATIONS

Korean Intellectual Property Office, Office Action, Korean Patent Application No. 10-2020-0125653, Feb. 12, 2025, 21 pages.
(Continued)

*Primary Examiner* — Gregory D Clark
(74) *Attorney, Agent, or Firm* — Fenwick & West LLP

(57) ABSTRACT

The present disclosure relates to an organic light emitting diode that includes a first electrode; a second electrode facing the first electrode; and a first emitting material layer including a first compound and a second compound and positioned between the first and second electrodes, wherein an overlap ratio between an absorption spectrum of the first compound and an emission spectrum of the second compound is equal to or greater than 35%, and an organic light emitting display including the organic light emitting diode.

14 Claims, 8 Drawing Sheets

(51) Int. Cl.

| | |
|---|---|
| ***C07D 487/04*** | (2006.01) |
| ***H10K 50/125*** | (2023.01) |
| ***H10K 85/60*** | (2023.01) |
| *H10K 59/12* | (2023.01) |
| *H10K 101/20* | (2023.01) |

(52) U.S. Cl.
CPC ......... *H10K 85/652* (2023.02); *H10K 85/654* (2023.02); *H10K 85/6572* (2023.02); *H10K 59/12* (2023.02); *H10K 2101/20* (2023.02)

(56) References Cited

U.S. PATENT DOCUMENTS

| | | | | |
|---|---|---|---|---|
| 12,185,624 | B2 | 12/2024 | Tada et al. | |
| 2009/0236974 | A1* | 9/2009 | Tamaru ................ | C09K 11/025 313/504 |
| 2010/0001301 | A1* | 1/2010 | Karg ...................... | H10K 50/86 257/40 |
| 2017/0352816 | A1 | 12/2017 | Jeon et al. | |
| 2018/0090705 | A1 | 3/2018 | Kim et al. | |
| 2018/0175294 | A1 | 6/2018 | Duan et al. | |
| 2018/0248145 | A1* | 8/2018 | Ihn ........................ | H10K 50/805 |
| 2019/0386235 | A1* | 12/2019 | Duan ..................... | H10K 50/15 |
| 2020/0052226 | A1 | 2/2020 | Seo et al. | |
| 2020/0083460 | A1 | 3/2020 | Duan et al. | |
| 2020/0411770 | A1 | 12/2020 | Tada et al. | |

FOREIGN PATENT DOCUMENTS

| | | |
|---|---|---|
| KR | 10-2018-0035528 A | 4/2018 |
| WO | WO 2019/171891 A1 | 9/2019 |

OTHER PUBLICATIONS

German Patent and Trade Mark Office, Office Action, German Patent Application No. 112021005092.3, Mar. 25, 2025, 13 pages.

PCT International Search Report and Written Opinion, PCT Application No. PCT/KR2021/012133, Dec. 14, 2021, 9 pages.

* cited by examiner

ORGANIC LIGHT EMITTING DIODE AND ORGANIC LIGHT EMITTING DEVICE INCLUDING THE SAME

TECHNICAL FIELD

The present disclosure relates to an organic light emitting diode, and more specifically, to an organic light emitting diode having high emitting efficiency and excellent color purity and an organic light emitting display device including the same.

BACKGROUND ART

Recently, requirement for flat panel display devices having small occupied area is increased. Among the flat panel display devices, a technology of an organic light emitting display device, which includes an organic light emitting diode (OLED) and may be called to as an organic electroluminescent device, is rapidly developed.

The OLED emits light by injecting electrons from a cathode as an electron injection electrode and holes from an anode as a hole injection electrode into an emitting material layer (EML), combining the electrons with the holes, generating an exciton, and transforming the exciton from an excited state to a ground state.

A fluorescent material may be used as an emitter in the OLED. However, since only singlet exciton is involved in the emission, the related art fluorescent material has a limitation in the emitting efficiency.

DISCLOSURE OF INVENTION

Technical Problem

Accordingly, the present disclosure is directed to an OLED and an organic light emitting device that substantially obviate one or more of the problems due to the limitations and disadvantages of the related art.

An object of the present disclosure is to provide an OLED having improved emitting efficiency and color purity.

Another object of the present disclosure is to provide an organic light emitting display device including the OLED and having improved emitting efficiency and color purity.

Additional features and advantages of the disclosure will be set forth in the description which follows, and in part will be apparent from the description, or may be learned by practice of the disclosure. The objectives and other advantages of the disclosure will be realized and attained by the structure particularly pointed out in the written description and claims hereof as well as the appended drawings.

Solution to Problem

According to an aspect, the present disclosure provides an organic light emitting diode comprising a first electrode; a second electrode facing the first electrode; and a first emitting material layer including a first compound and a second compound and positioned between the first and second electrodes, wherein the first compound is represented by Formula 1: wherein each of R1 and R2 is independently selected from the group consisting of hydrogen, deuterium, C1 to C20 alkyl group, C6 to C30 aryl group and C3 to C40 heteroaryl group, wherein each of R3 and R4 is independently selected from the group consisting of hydrogen, deuterium, C1 to C20 alkyl group, C6 to C30 aryl group and C4 to C40 heteroaryl group, or at least one pair of adjacent two of R3 and adjacent two R4 are linked to each other to form a fused ring, wherein the second compound is represented by Formula 2: wherein each of R11 and R12 is independently selected from the group consisting of hydrogen, deuterium, cyano, C1 to C20 alkyl group, C6 to C30 aryl group and C3 to C40 heteroaryl group, wherein R13 is selected from the group consisting of hydrogen, deuterium, cyano, C1 to C20 alkyl group, C6 to C30 aryl group and C3 to C40 heteroaryl group, wherein X is selected from the group consisting of cyano, nitro, halogen, C1 to C20 alkyl group substituted with cyano, nitro or halogen, C6 to C30 aryl group substituted with cyano, nitro or halogen and C3 to C40 heteroaryl group substituted with cyano, nitro or halogen, and wherein L is selected from C6 to C30 arylene group, and n is 0 or 1.

[Formula 1]

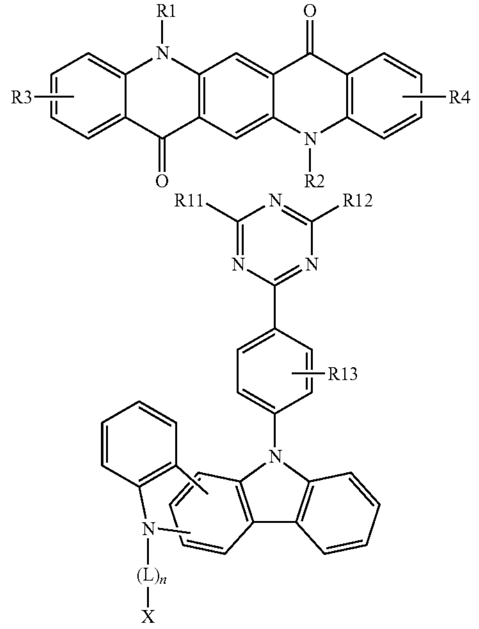

According to another aspect, the present disclosure provides an organic light emitting display device that includes a substrate; the above organic light emitting diode over the substrate; and an encapsulation film covering the organic light emitting diode.

It is to be understood that both the foregoing general description and the following detailed description are examples and are explanatory and are intended to provide further explanation of the disclosure as claimed.

Advantageous Effects of Invention

In an OLED and an organic light emitting device, a first compound being a fluorescent material and a second compound being a delayed fluorescent material, in which an indolocarbazole moiety substituted with an electron withdrawing group and a triazine moiety are linked (connected or combined) via a linker, are included in a single emitting material layer or adjacent emitting material layers. As a result, the emitting properties of the OLED and the organic light emitting device are improved.

Namely, the color purity is improved by the first compound being the fluorescent material, and the emitting efficiency is improved by the second compound being the delayed fluorescent material. As a result, the OLED and the organic light emitting display device having excellent color purity and improved emitting efficiency are provided.

BRIEF DESCRIPTION OF DRAWINGS

The accompanying drawings, which are included to provide a further understanding of the disclosure, are incorporated in and constitute a part of this specification, illustrate implementations of the disclosure and together with the description serve to explain the principles of embodiments of the disclosure.

MODE FOR THE INVENTION

Reference will now be made in detail to aspects of the disclosure, examples of which are illustrated in the accompanying drawings.

The present disclosure relates to an OLED, in which a delayed fluorescent material and a fluorescent material are provided in a single emitting material layer or adjacent emitting material layers, and an organic light emitting device including the OLED. An absorption spectrum of the fluorescent material and an emission spectrum of the delayed fluorescent material are matched. For example, the organic light emitting device may be an organic light emitting display device or an organic lightening device. As an example, an organic light emitting display device, which is a display device including the OLED of the present disclosure, will be mainly described.

Figure 1:
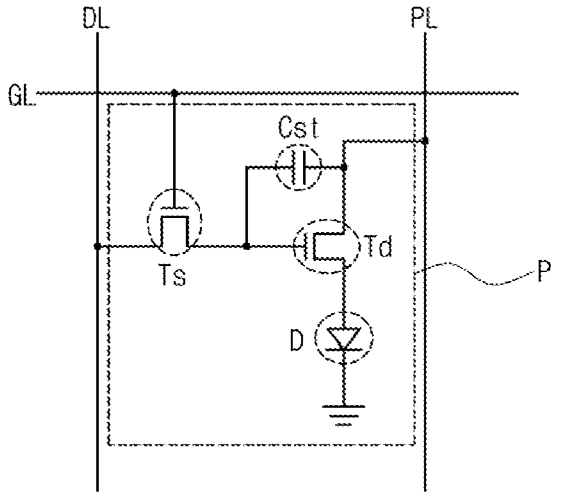
FIG. 1 is a schematic circuit diagram of an organic light emitting display device of the present disclosure.

FIG. 1 is a schematic circuit diagram of an organic light emitting display device of the present disclosure.

As shown in FIG. 1, an organic light emitting display device includes a gate line GL, a data line DL, a power line PL, a switching thin film transistor TFT Ts, a driving TFT Td, a storage capacitor Cst, and an OLED D. The gate line GL and the data line DL cross each other to define a pixel region P. The pixel region P may include a red pixel region, a green pixel region and a blue pixel region.

The switching TFT Ts is connected to the gate line GL and the data line DL, and the driving TFT Td and the storage capacitor Cst are connected to the switching TFT Ts and the power line PL. The OLED D is connected to the driving TFT Td.

In the organic light emitting display device, when the switching TFT Ts is turned on by a gate signal applied through the gate line GL, a data signal from the data line DL is applied to the gate electrode of the driving TFT Td and an electrode of the storage capacitor Cst.

When the driving TFT Td is turned on by the data signal, an electric current is supplied to the OLED D from the power line PL. As a result, the OLED D emits light. In this case, when the driving TFT Td is turned on, a level of an electric current applied from the power line PL to the OLED D is determined such that the OLED D can produce a gray scale.

The storage capacitor Cst serves to maintain the voltage of the gate electrode of the driving TFT Td when the switching TFT Ts is turned off. Accordingly, even if the switching TFT Ts is turned off, a level of an electric current applied from the power line PL to the OLED D is maintained to next frame.

As a result, the organic light emitting display device displays a desired image.

Figure 2:
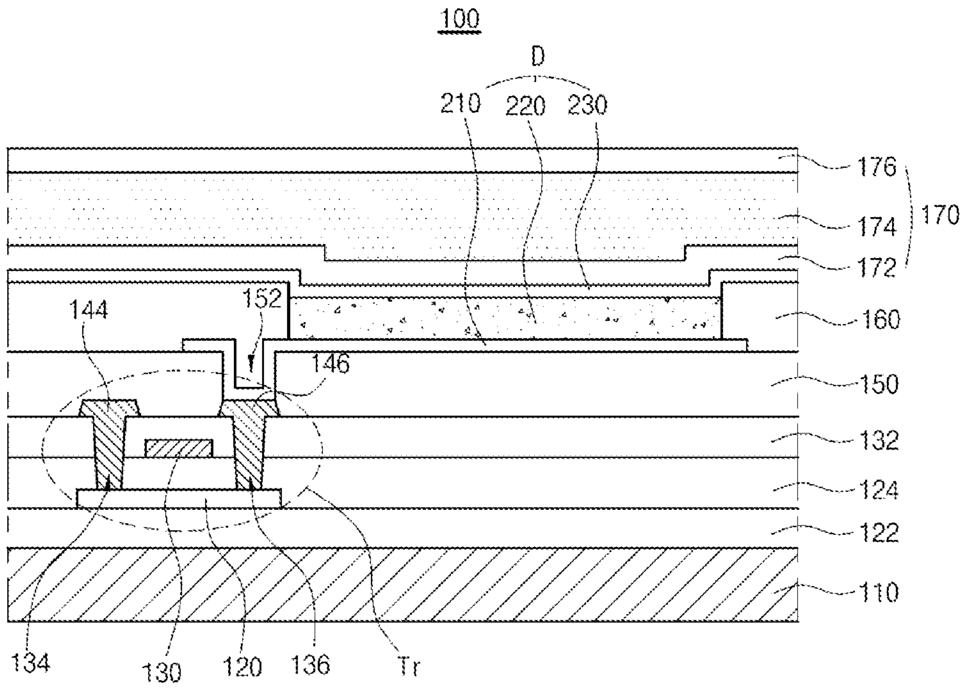
FIG. 2 is a schematic cross-sectional view of an organic light emitting display device according to a first embodiment of the present disclosure.

FIG. 2 is a schematic cross-sectional view of an organic light emitting display device according to a first embodiment of the present disclosure.

As shown in FIG. 2, the organic light emitting display device 100 includes a substrate 110, a TFT Tr and an OLED D connected to the TFT Tr.

The substrate 110 may be a glass substrate or a flexible substrate. For example, the flexible substrate may be a polyimide (PI) substrate, a polyethersulfone (PES) substrate, a polyethylenenaphthalate (PEN) substrate, a polyethylene terephthalate (PET) substrate or a polycarbonate (PC) substrate.

A buffer layer 122 is formed on the substrate, and the TFT Tr is formed on the buffer layer 122. The buffer layer 122 may be omitted.

A semiconductor layer 120 is formed on the buffer layer 122. The semiconductor layer 120 may include an oxide semiconductor material or polycrystalline silicon.

When the semiconductor layer 120 includes the oxide semiconductor material, a light-shielding pattern (not shown) may be formed under the semiconductor layer 120. The light to the semiconductor layer 120 is shielded or blocked by the light-shielding pattern such that thermal degradation of the semiconductor layer 120 can be prevented. On the other hand, when the semiconductor layer 120 includes polycrystalline silicon, impurities may be doped into both sides of the semiconductor layer 120.

A gate insulating layer 124 is formed on the semiconductor layer 120. The gate insulating layer 124 may be formed of an inorganic insulating material such as silicon oxide or silicon nitride.

A gate electrode 130, which is formed of a conductive material, e.g., metal, is formed on the gate insulating layer 124 to correspond to a center of the semiconductor layer 120. In FIG. 2, the gate insulating layer 124 is formed on an entire surface of the substrate 110. Alternatively, the gate insulating layer 124 may be patterned to have the same shape as the gate electrode 130.

An interlayer insulating layer 132, which is formed of an insulating material, is formed on the gate electrode 130. The interlayer insulating layer 132 may be formed of an inorganic insulating material, e.g., silicon oxide or silicon nitride, or an organic insulating material, e.g., benzocyclobutene or photo-acryl.

The interlayer insulating layer 132 includes first and second contact holes 134 and 136 exposing both sides of the semiconductor layer 120. The first and second contact holes 134 and 136 are positioned at both sides of the gate electrode 130 to be spaced apart from the gate electrode 130.

The first and second contact holes 134 and 136 are formed through the gate insulating layer 124. Alternatively, when the gate insulating layer 124 is patterned to have the same shape as the gate electrode 130, the first and second contact holes 134 and 136 are formed only through the interlayer insulating layer 132.

A source electrode 144 and a drain electrode 146, which are formed of a conductive material, e.g., metal, are formed on the interlayer insulating layer 132.

The source electrode 144 and the drain electrode 146 are spaced apart from each other with respect to the gate electrode 130 and respectively contact both sides of the semiconductor layer 120 through the first and second contact holes 134 and 136.

The semiconductor layer 120, the gate electrode 130, the source electrode 144 and the drain electrode 146 constitute the TFT Tr. The TFT Tr serves as a driving element. Namely, the TFT Tr is the driving TFT Td (of FIG. 1).

In the TFT Tr, the gate electrode 130, the source electrode 144, and the drain electrode 146 are positioned over the semiconductor layer 120. Namely, the TFT Tr has a coplanar structure.

Alternatively, in the TFT Tr, the gate electrode may be positioned under the semiconductor layer, and the source and drain electrodes may be positioned over the semiconductor layer such that the TFT Tr may have an inverted staggered structure. In this instance, the semiconductor layer may include amorphous silicon.

Although not shown, the gate line and the data line cross each other to define the pixel region, and the switching TFT is formed to be connected to the gate and data lines. The switching TFT is connected to the TFT Tr as the driving element. In addition, the power line, which may be formed to be parallel to and spaced apart from one of the gate and data lines, and the storage capacitor for maintaining the voltage of the gate electrode of the TFT Tr in one frame may be further formed.

A planarization layer 150 is formed on an entire surface of the substrate 110 to cover the source and drain electrodes 144 and 146. The planarization layer 150 provides a flat top surface and has a drain contact hole 152 exposing the drain electrode 146 of the TFT Tr.

The OLED D is disposed on the planarization layer 150 and includes a first electrode 210, which is connected to the drain electrode 146 of the TFT Tr, a light emitting layer 220 and a second electrode 230. The light emitting layer 220 and the second electrode 230 are sequentially stacked on the first electrode 210. The OLED D is positioned in each of the red, green and blue pixel regions and respectively emits the red, green and blue light.

The first electrode 210 is separately formed in each pixel region. The first electrode 210 may be an anode and may be formed of a conductive material, e.g., a transparent conductive oxide (TCO), having a relatively high work function. For example, the first electrode 210 may be formed of indium-tin-oxide (ITO), indium-zinc-oxide (IZO), indium-tin-zinc-oxide (ITZO), tin oxide (SnO), zinc oxide (ZnO), indium-copper-oxide (ICO) or aluminum-zinc-oxide (Al:ZnO, AZO).

When the organic light emitting display device 100 is operated in a bottom-emission type, the first electrode 210 may have a single-layered structure of the transparent conductive material layer. When the Organic light emitting display device 100 is operated in a top-emission type, a reflection electrode or a reflection layer may be formed under the first electrode 210. For example, the reflection electrode or the reflection layer may be formed of silver (Ag) or aluminum-palladium-copper (APC) alloy. In this instance, the first electrode 210 may have a triple-layered structure of ITO/Ag/ITO or ITO/APC/ITO.

In addition, a bank layer 160 is formed on the planarization layer 150 to cover an edge of the first electrode 210. Namely, the bank layer 160 is positioned at a boundary of the pixel region and exposes a center of the first electrode 210 in the pixel region.

The light emitting layer 220 as an emitting unit is formed on the first electrode 210. The light emitting layer 220 may have a single-layered structure of an emitting material layer (EML) including an emitting material. Alternatively, the light emitting layer 220 may have a multi-layered structure. For example, the light emitting layer 220 may further include at least one of a hole injection layer (HIL), a hole transporting layer (HTL), an electron blocking layer (EBL), a hole blocking layer (HBL), an electron transporting layer (ETL) and an electron injection layer (EIL). The HIL, the HTL and the EBL are sequentially disposed between the first electrode 210 and the EML, and the HBL, the ETL and the EIL are sequentially disposed between the EML and the second electrode 230. In addition, the EML may have a single-layered structure or a multi-layered structure. Moreover, the light emitting layer 220 may include at least two EMLs spaced apart from each other such that the OLED may have a tandem structure.

The second electrode 230 is formed over the substrate 110 where the light emitting layer 220 is formed. The second electrode 230 covers an entire surface of the display area and may be formed of a conductive material having a relatively low work function to serve as a cathode. For example, the second electrode 230 may be formed of aluminum (Al), magnesium (Mg), calcium (Ca), silver (Ag) or their alloy or combination. In the top-emission type organic light emitting display device 100, the second electrode 230 may have a thin profile (small thickness) to provide a light transmittance property (or a semi-transmittance property).

Although not shown, the organic light emitting display device 100 may include a color filter corresponding to the red, green and blue pixel regions. For example, when the OLED D, which has the tandem structure and emits the white light, is formed to all of the red, green and blue pixel regions, a red color filter pattern, a green color filter pattern and a blue color filter pattern may be formed in the red, green and blue pixel regions, respectively, such that a full-color display is provided.

When the organic light emitting display device 100 is operated in a bottom-emission type, the color filter may be disposed between the OLED D and the substrate 110, e.g., between the interlayer insulating layer 132 and the planarization layer 150. Alternatively, when the organic light emitting display device 100 is operated in a top-emission type, the color filter may be disposed over the OLED D, e.g., over the second electrode 230.

An encapsulation film 170 is formed on the second electrode 230 to prevent penetration of moisture into the OLED D. The encapsulation film 170 includes a first inorganic insulating layer 172, an organic insulating layer 174 and a second inorganic insulating layer 176 sequentially stacked, but it is not limited thereto.

The Organic light emitting display device 100 may further include a polarization plate (not shown) for reducing an ambient light reflection. For example, the polarization plate may be a circular polarization plate. In the bottom-emission type organic light emitting display device 100, the polarization plate may be disposed under the substrate 110. In the top-emission type organic light emitting display device 100, the polarization plate may be disposed on or over the encapsulation film 170.

In addition, in the top-emission type organic light emitting display device 100, a cover window (not shown) may be attached to the encapsulation film 170 or the polarization plate. In this instance, the substrate 110 and the cover window have a flexible property such that a flexible organic light emitting display device may be provided.

Figure 3:
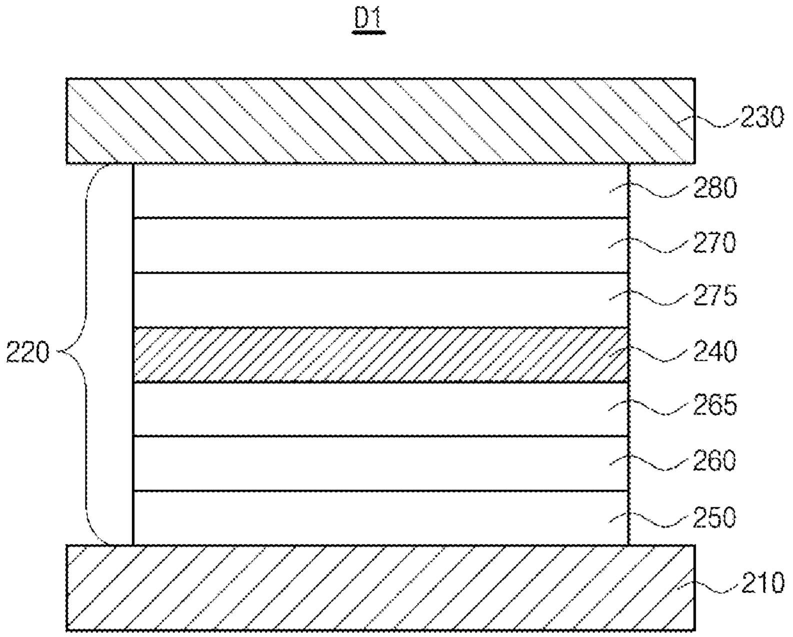
FIG. 3 is a schematic cross-sectional view of an OLED according to a second embodiment of the present disclosure.

FIG. 3 is a schematic cross-sectional view of an OLED according to a second embodiment of the present disclosure.

As shown in FIG. 3, the OLED D1 includes the first and second electrodes 210 and 230, which face each other, and the light emitting layer 220 therebetween. The light emitting layer 220 includes an emitting material layer (EML) 240. The organic light emitting display device 100 (of FIG. 2) may include a red pixel region, a green pixel region and a blue pixel region, and the OLED D1 may be positioned in the green pixel region.

The first electrode 210 may be an anode, and the second electrode 230 may be a cathode.

The light emitting layer 220 further include at least one of a hole transporting layer (HTL) 260 between the first electrode 210 and the EML 240 and an electron transporting layer (ETL) 270 between the second electrode 230 and the EML 240.

In addition, the light emitting layer 220 may further include at least one of a hole injection layer (HIL) 250 between the first electrode 210 and the HTL 260 and an electron injection layer (EIL) 280 between the second electrode 230 and the ETL 270.

Moreover, the light emitting layer 220 may further include at least one of an electron blocking layer (EBL) 265 between the HTL 260 and the EML 240 and a hole blocking layer (HBL) 275 between the EML 240 and the ETL 270.

For example, the HIL 250 may include at least one compound selected from the group consisting of 4,4',4"-tris(3-methylphenylamino)triphenylamine (MTDATA), 4,4',4"-tris(N,N-diphenyl-amino)triphenylamine (NATA), 4,4',4"-tris(N-(naphthalene-1-yl)-N-phenyl-amino)triphenylamine (1T-NATA), 4,4',4"-tris(N-(naphthalene-2-yl)-N-phenyl-amino)triphenylamine (2T-NATA), copper phthalocyanine (CuPc), tris(4-carbazoyl-9-yl-phenyl)amine (TCTA), N,N'-diphenyl-N,N'-bis(1-naphthyl)-1,1'-biphenyl-4,4"-diamine (NPB; NPD), 1,4,5,8,9,11-hexaazatriphenylenehexacarbonitrile (dipyrazino[2,3-f:2'3'-h]quinoxaline-2,3,6,7,10,11-hexacarbonitrile; HAT-CN), 1,3,5-tris[4-(diphenylamino)phenyl]benzene (TDAPB), poly(3,4-ethylenedioxythiphene)polystyrene sulfonate (PEDOT/PSS), and N-(biphenyl-4-yl)-9,9-dimethyl-N-(4-(9-phenyl-9H-carbazol-3-yl)phenyl)-9H-fluoren-2-amine, but it is not limited thereto.

The HTL 260 may include at least one compound selected from the group consisting of N,N'-diphenyl-N,N'-bis(3-methylphenyl)-1,1'-biphenyl-4,4'-diamine; TPD), NPB (NPD), 4,4'-bis(N-carbazolyl)-1,1'-biphenyl (CBP), poly[N,N'-bis(4-butylpnehyl)-N,N'-bis(phenyl)-benzidine](Poly-TPD), (poly[(9,9-dioctylfluorenyl-2,7-diyl)-co-(4,4'-(N-(4-sec-butylphenyl)diphenylamine))](TFB), di-[4-(N,N-di-p-tolyl-amino)-phenyl]cyclohexane (TAPC), 3,5-di(9H-carbazol-9-yl)-N,N-diphenylaniline (DCDPA), N-(biphenyl-4-yl)-9,9-dimethyl-N-(4-(9-phenyl-9H-carbazol-3-yl)phenyl)-9H-fluoren-2-amine, and N-(biphenyl-4-yl)-N-(4-(9-phenyl-9H-carbazol-3-yl)phenyl) biphenyl-4-amine, but it is not limited thereto.

The ETL 270 may include at least one of an oxadiazole-based compound, a triazole-based compound, a phenanthroline-based compound, a benzoxazole-based compound, a benzothiazole-based compound, a benzimidazole-based compound, and a triazine-based compound. For example, the ETL 270 may include at least one compound selected from the group consisting of tris-(8-hydroxyquinoline aluminum (Alq3), 2-biphenyl-4-yl-5-(4-t-butylphenyl)-1,3,4-oxadiazole (PBD), spiro-PBD, lithium quinolate (Liq), 1,3,5-tris(N-phenylbenzimidazol-2-yl)benzene (TPBi), bis(2-methyl-8-quinolinolato-N1,O8)-(1,1'-biphenyl-4-olato) aluminum (BAlq), 4,7-diphenyl-1,10-phenanthroline (Bphen), 2,9-bis(naphthalene-2-yl) 4,7-diphenyl-1,10-phenanthroline (NBphen), 2,9-dimethyl-4,7-diphenyl-1,10-phenathroline (BCP), 3-(4-biphenyl)-4-phenyl-5-tert-butylphenyl-1,2,4-triazole (TAZ), 4-(naphthalen-1-yl)-3,5-diphenyl-4H-1,2,4-triazole (NTAZ), 1,3,5-tri(p-pyrid-3-yl-phenyl)benzene (TpPyPB), 2,4,6-tris(3'-(pyridin-3-yl)biphenyl-3-yl) 1,3,5-triazine (TmPPPyTz), Poly[9,9-bis(3'-((N,N-dimethyl)-N-ethylammonium)-propyl)-2,7-fluorene]-alt-2,7-(9,9-dioctylfluorene)](PFNBr), tris(phenylquinoxaline (TPQ), and diphenyl-4-triphenylsilyl-phenylphosphine oxide (TSPO1), but it is not limited thereto.

The EIL 280 may include at least one of an alkali halide compound, such as LiF, CsF, NaF, or BaF2, and an organometallic compound, such as Liq, lithium benzoate, or sodium stearate, but it is not limited thereto.

The EBL 265, which is positioned between the HTL 260 and the EML 240 to block the electron transfer from the EML 240 into the HTL 260, may include at least one compound selected from the group consisting of TCTA, tris[4-(diethylamino)phenyl]amine, N-(biphenyl-4-yl)-9,9-dimethyl-N-(4-(9-phenyl-9H-carbazol-3-yl)phenyl)-9H-fluoren-2-amine, TAPC, MTDATA, 1,3-bis(carbazol-9-yl)benzene (mCP), 3,3'-bis(N-carbazolyl)-1,1'-biphenyl (mCBP), CuPc, N,N'-bis[4-[bis(3-methylphenyl)amino]phenyl]-N,N'-diphenyl-[1,1'-biphenyl]-4,4'-diamine (DNTPD), TDAPB, DCDPA, and 2,8-bis(9-phenyl-9H-carbazol-3yl)dibenzo[b,d]thiophene), but it is not limited thereto.

The HBL 275, which is positioned between the EML 240 and the ETL 270 to block the hole transfer from the EML 240 into the ETL 270, may include the above material of the ETL 270. For example, the material of the HBL 275 has a HOMO energy level being lower than a material of the EML 240 and may be at least one compound selected from the group consisting of BCP, BAlq, Alq3, PBD, spiro-PBD, Liq, bis-4,6-(3,5-di-3-pyridylphenyl)-2-methylpyrimidine (B3PYMPM), bis[2-(diphenylphosphino)phenyl]teeth oxide (DPEPO), 9-(6-9H-carbazol-9-yl)pyridine-3-yl)-9H-3,9'-bicarbazole, and TSPO1, but it is not limited thereto.

The EML 240 includes a first compound being a fluorescent material (compound) and a second compound being a delayed fluorescent material (compound). The EML 240 including the first and second compounds provides the green emission, and the OLED D1 is disposed in the green pixel region.

The first compound is represented by Formula 1.

[Formula 1]

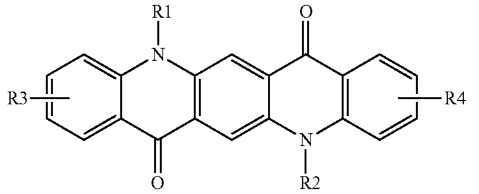

In Formula 1, each of R1 and R2 is independently selected from the group consisting of hydrogen (H), deuterium (D), C1 to C20 alkyl group, C6 to C30 aryl group and C3 to C40 heteroaryl group. Each of R3 and R4 is independently selected from the group consisting of H, D, C1 to C20 alkyl group, C6 to C30 aryl group and C4 to C40 heteroaryl group, or at least one pair of adjacent two of R3 and adjacent two R4 are linked (connected or combined) to each other to form a fused ring.

R1 and R2 may be same or different, and each of R1 and R2 may be independently selected from the group consisting of C1 to C20 alkyl group and C6 to C30 aryl group. For example, each of R1 and R2 may be independently selected from the group consisting of ethyl, isopropyl, tert-butyl and phenyl.

R3 and R4 may be same or different, and each of R3 and R4 may be independently selected from the group consisting of H and C1 to C20 alkyl group. For example, each of R3 and R4 may be independently selected from the group consisting of H, methyl and tert-butyl.

The second compound is represented by Formula 2.

[Formula 2]

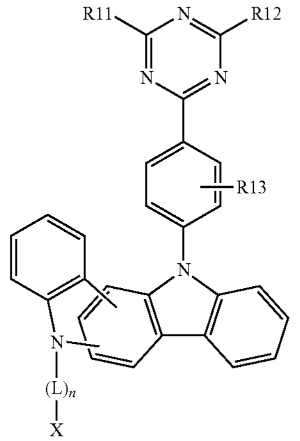

In Formula 2, each of R11 and R12 is independently selected from the group consisting of H, D, cyano, C1 to C20 alkyl group, C6 to C30 aryl group and C3 to C40 heteroaryl group. R13 is selected from the group consisting of H, D, cyano, C1 to C20 alkyl group, C6 to C30 aryl group and C3 to C40 heteroaryl group, and X is selected from the group consisting of cyano, nitro, halogen, C1 to C20 alkyl group substituted with cyano, nitro or halogen, C6 to C30 aryl group substituted with cyano, nitro or halogen and C3 to C40 heteroaryl group substituted with cyano, nitro or halogen. L is selected from C6 to C30 arylene group, and n is 0 or 1.

Namely, the second compound includes an electron withdrawing group, e.g., X, an indolocarbazole moiety, a triazine moiety and a phenylene linker. In this instance, the electron withdrawing group X and the indolocarbazole moiety are linked via a linker, e.g., L, or directly, and the indolocarbazole moiety and the triazine moiety are linked via the phenylene linker.

For example, each of R11 and R12 may be independently selected from C6 to C30 aryl group, e.g., phenyl, and R13 may be cyano. X may be selected from the group consisting of triazine derivative, pyrimidine derivative, pyridine derivative, cyano, alkyl group substituted with halogen. In an embodiment, X may be selected from the group consisting of diphenyltriazinyl, diphenylpyrimidinyl, dimethyltriazinyl, dimethylpyrimidinyl, cyanophenyl and trifluoromethylphеyl. L may be phenylene.

In Formulas 1 and 2, the alkyl group, the aryl group and the heteroaryl group may be unsubstituted or substituted. For example, the substituent to the alkyl group, the aryl group and the heteroaryl group may be D, C1 to C20 alkyl, C6 to C30 aryl or C5 to C30 heteroaryl.

In Formulas 1 and 2, the C6 to C30 aryl (or arylene) group may be selected from the group consisting of phenyl, biphenyl, terphenyl, naphthyl, anthracenyl, pentanenyl, indenyl, indenoindenyl, heptalenyl, biphenylenyl, indacenyl, phenanthrenyl, benzophenanthrenyl, dibenzophenanthrenyl, azulenyl, pyrenyl, fluoranthenyl, triphenylenyl, chrysenyl, tetraphenyl, tetrasenyl, picenyl, pentaphenyl, pentacenyl, fluorenyl, indenofluorenyl and spiro-fluorenyl.

In Formulas 1 and 2, the C5 to C30 heteroaryl group may be selected from the group consisting of pyrrolyl, pyridinyl, pyrimidinyl, pyrazinyl, pyridazinyl, triazinyl, tetrazinyl, imidazolyl, pyrazolyl, indolyl, isoindolyl, indazolyl, indolizinyl, pyrrolizinyl, carbazolyl, benzocarbazolyl, dibenzocarbazolyl, indolocarbazolyl, indenocarbazolyl, benzofurocarbazolyl, benzothienocarbazolyl, quinolinyl, isoquinolinyl, phthalazinyl, quinoxalinyl, sinolinyl, quinazolinyl, quinozolinyl, quinolinyl, purinyl, phthalazinyl, quinoxalinyl, benzoquinolinyl, benzoisoquinolinyl, benzoquinazolinyl, benzoquinoxalinyl, acridinyl, phenanthrolinyl, perimidinyl, phenanthridinyl, pteridinyl, cinnolinyl, naphtharidinyl, furanyl, oxazinyl, oxazolyl, oxadiazolyl, triazolyl, dioxynyl, benzofuranyl, dibenzofuranyl, thiopyranyl, xantenyl, chromaenyl, isochromenyl, thioazinyl, thiophenyl, benzothiophenyl, dibenzothiophenyl, difuropyrazinyl, benzofurodibenzofuranyl, benzothienobenzothiophenyl, benzothienodibenzothiophenyl, benzothienobenzofuranyl, and benzothienodibenzofuranyl.

In addition, in Formulas 1 and 2, the fused ring may be C6 to C20 alicyclic ring, C4-C20 hetero-alicyclic ring, C6-C20 aromatic ring, or C4-C20 heteroaromatic ring.

For example, the first compound may be one of the compounds in Formula 3.

[Formula 3]
1-1
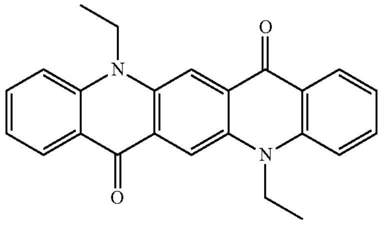
1-2
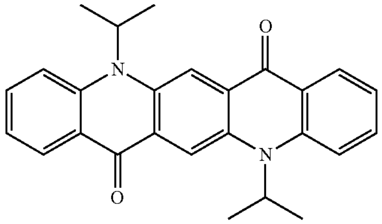
1-3
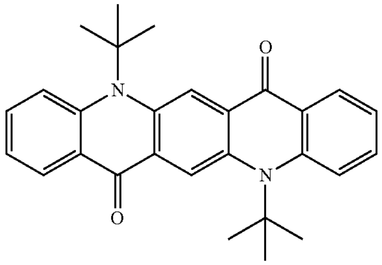
1-4
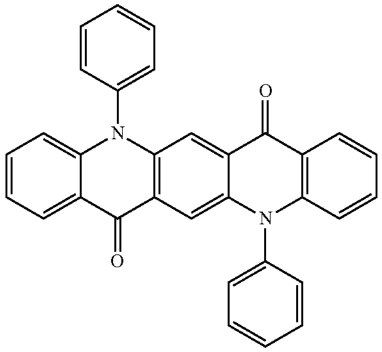
1-5
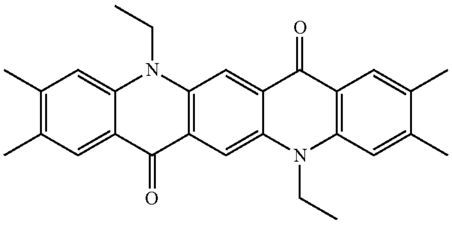
1-6
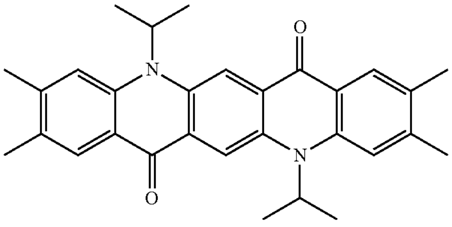
-continued
1-7
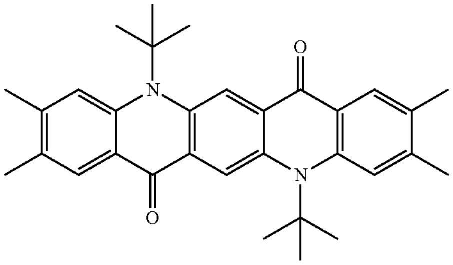
1-8
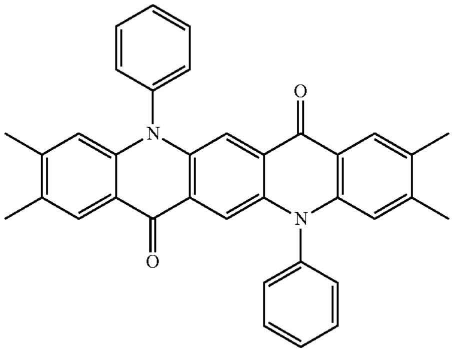
1-9
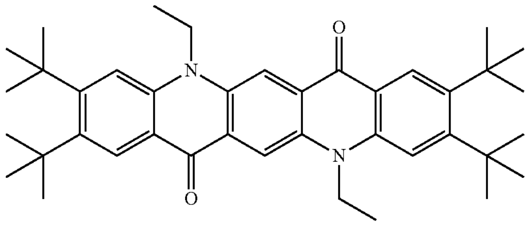
1-10
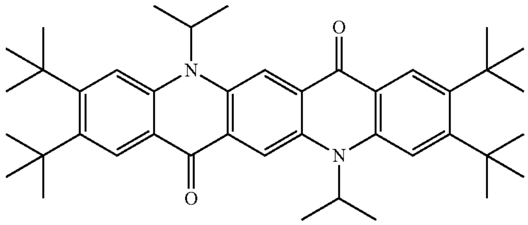
1-11
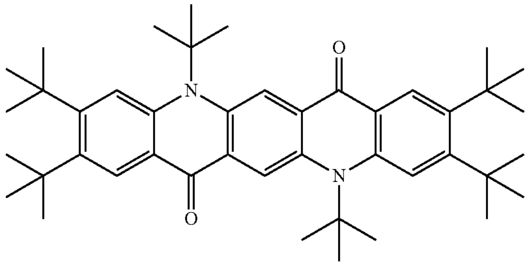

-continued
1-12
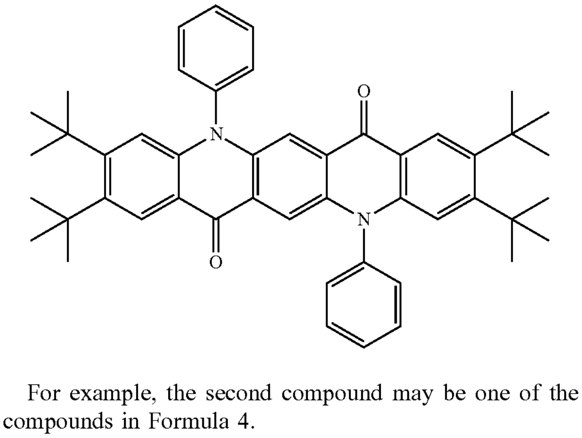
For example, the second compound may be one of the compounds in Formula 4.
[Formula 4]
2-1
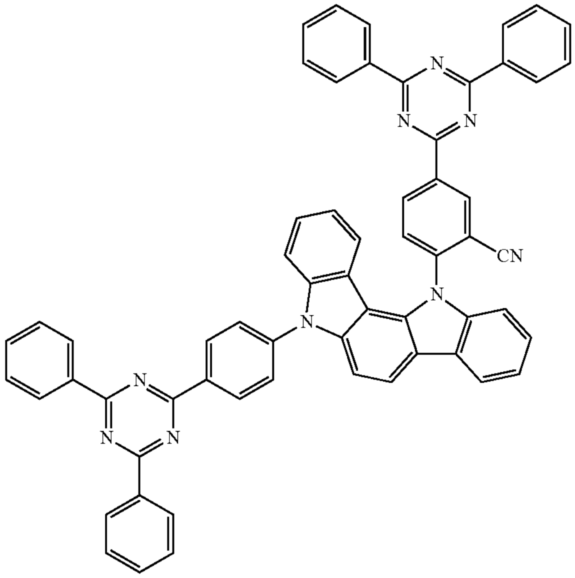
2-2
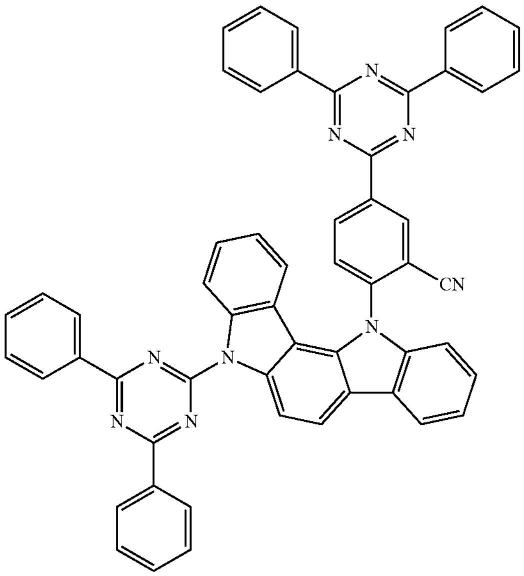
-continued
2-3
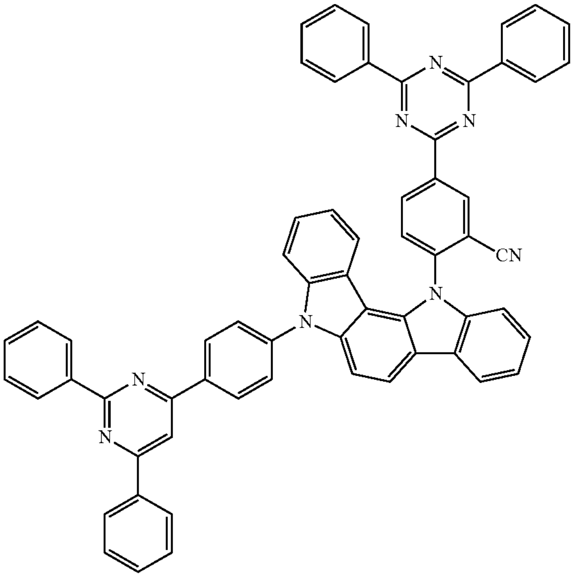
2-4
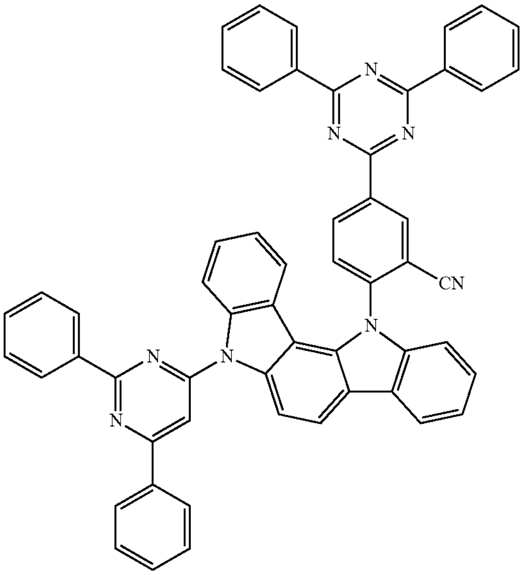

-continued
2-5
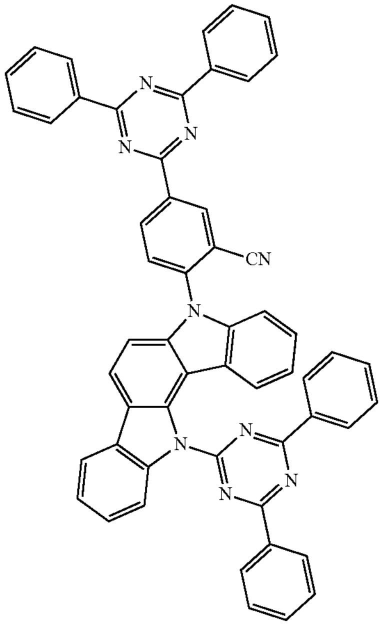
2-6
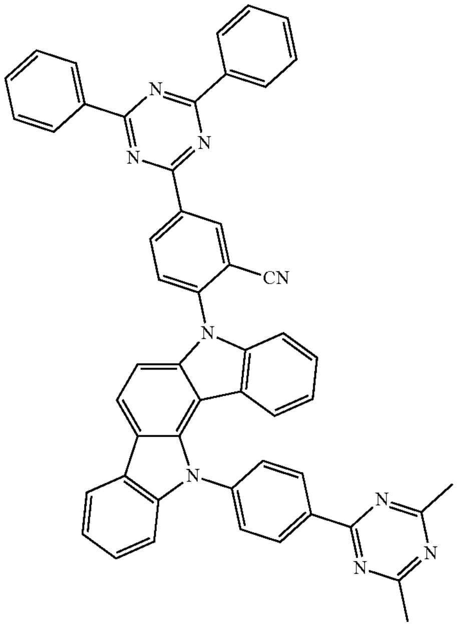
-continued
2-7
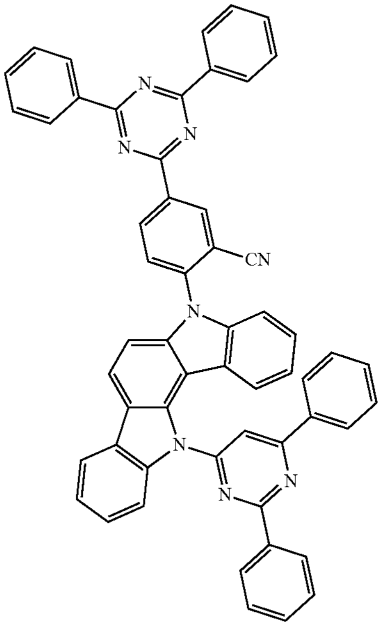
2-8
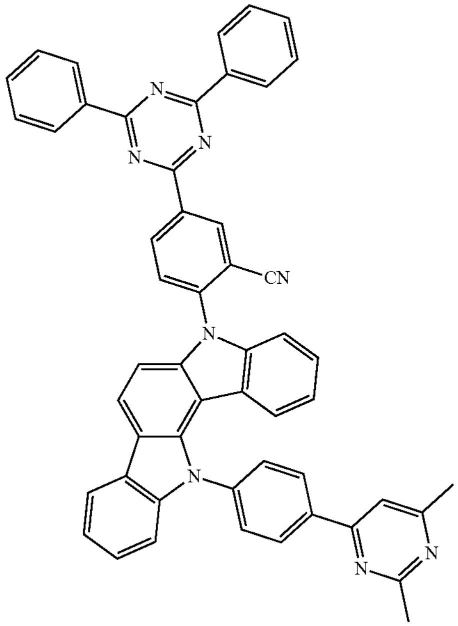

-continued
2-9
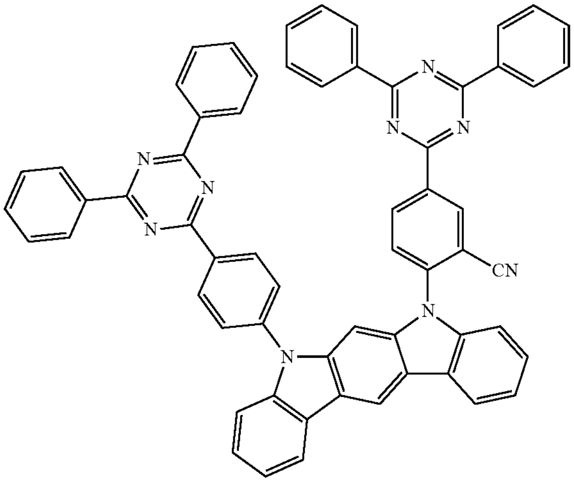
2-10
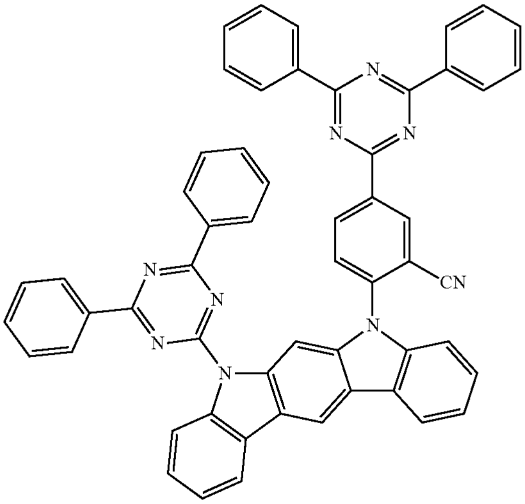
2-11
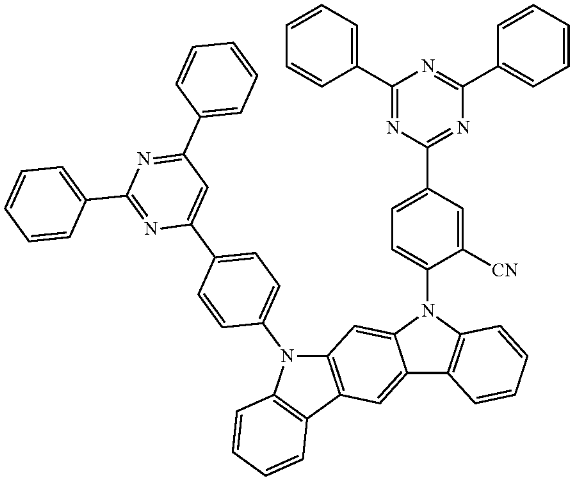
-continued
2-12
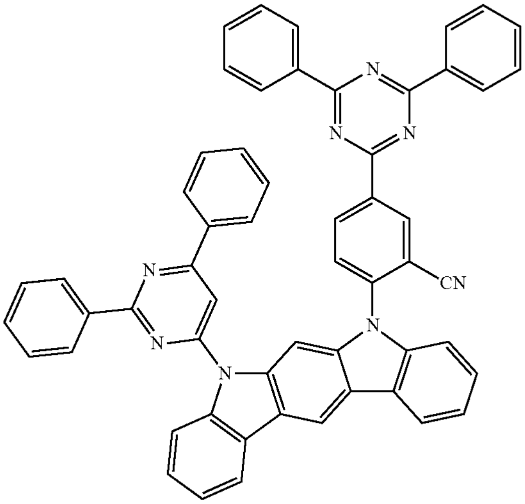
2-13
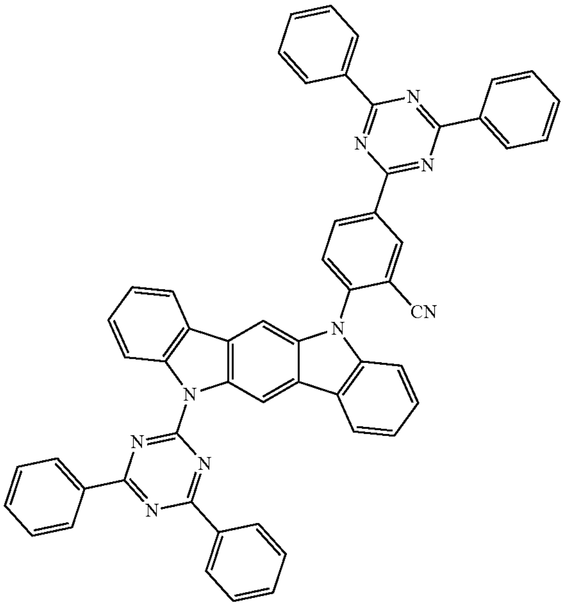

-continued
2-14
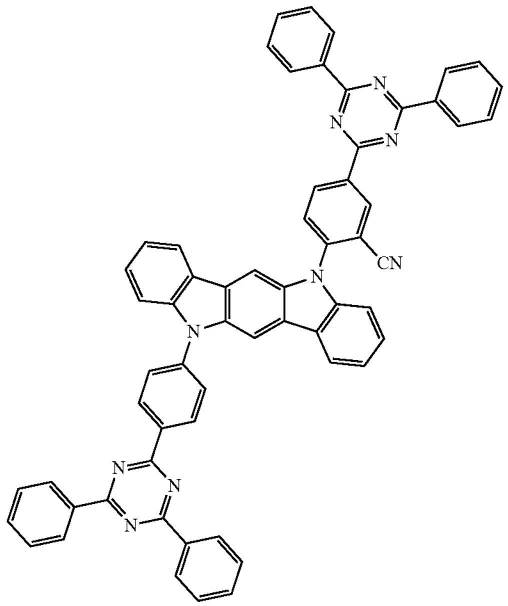
2-15
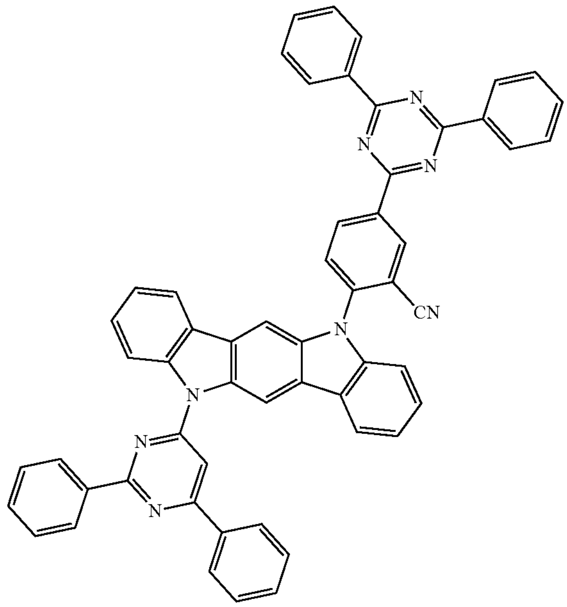
-continued
2-16
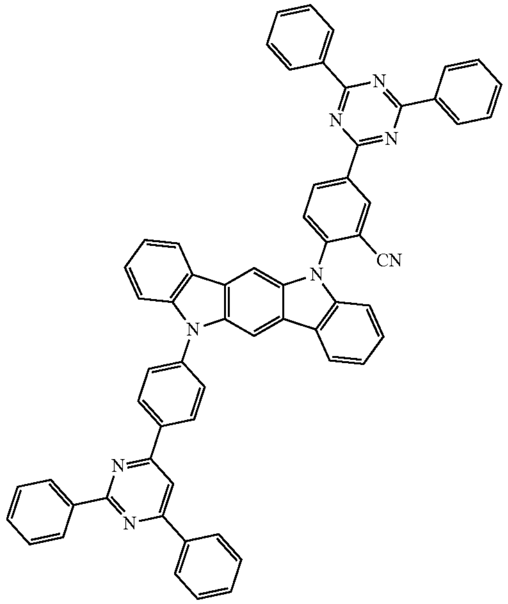
2-17
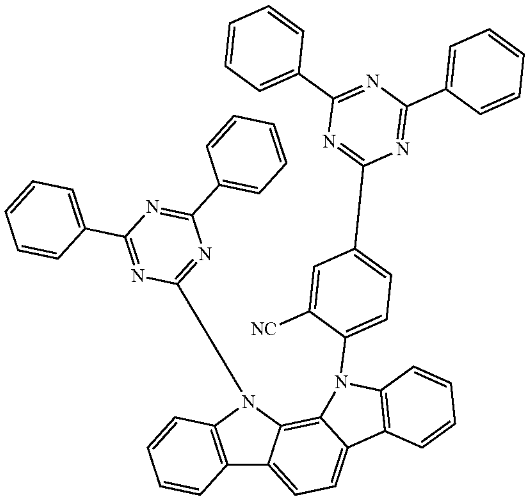
2-18
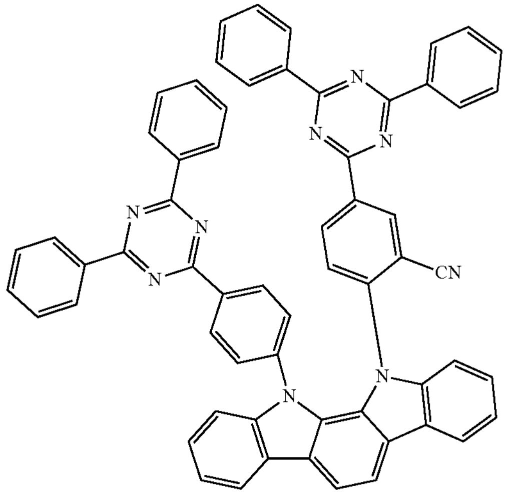

-continued
2-19
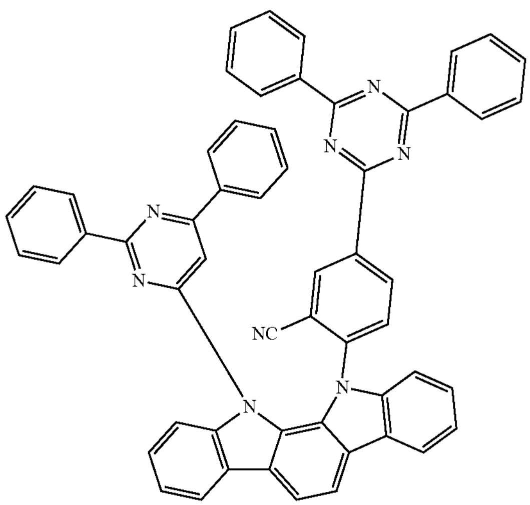
2-20
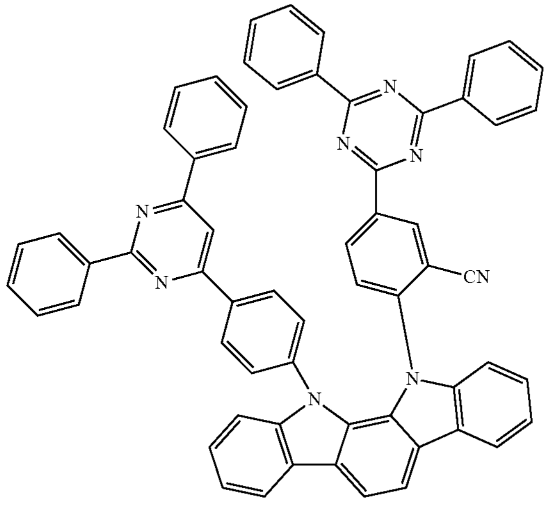
-continued
2-21
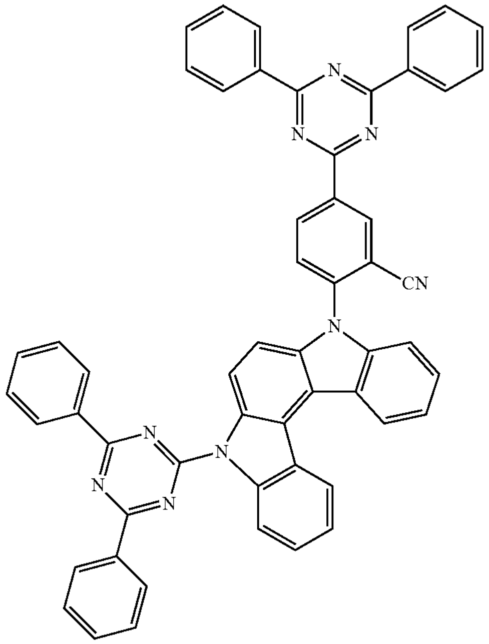
2-22
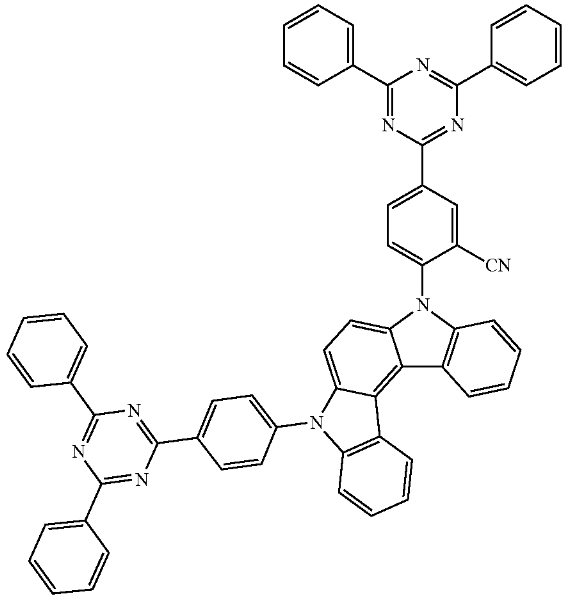

-continued
2-23
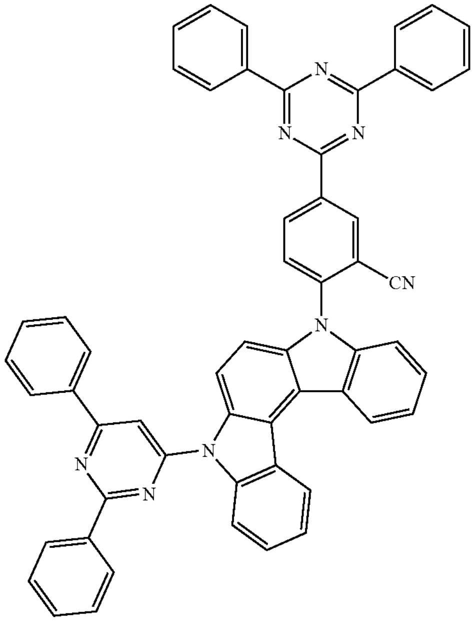
2-24
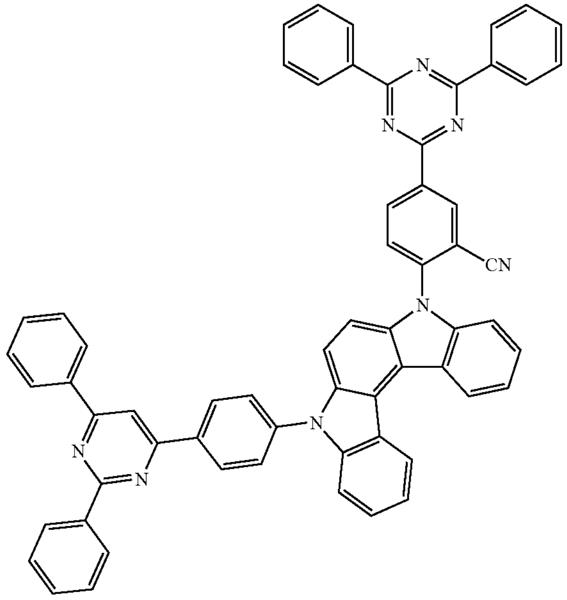
-continued
2-25
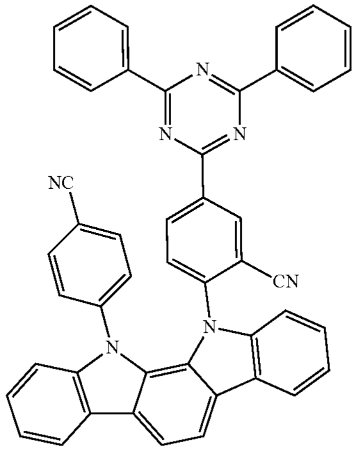
2-26
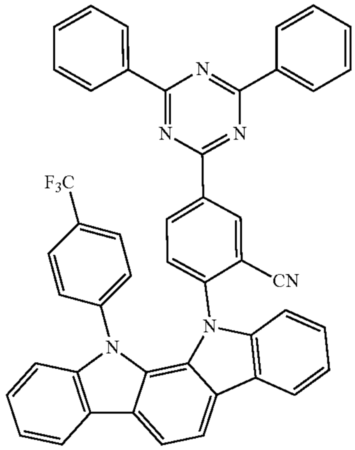
2-27
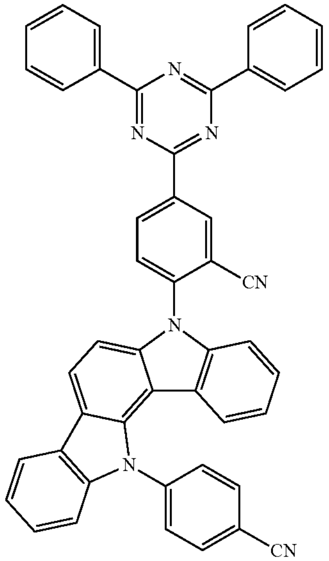

-continued
2-28
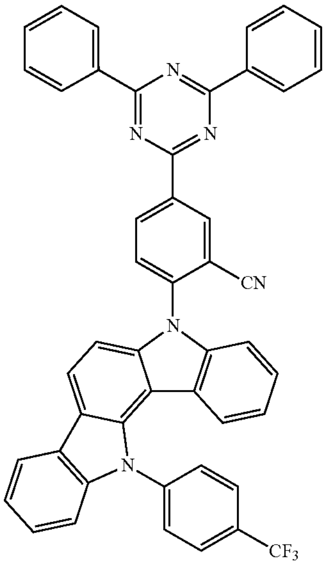
2-29
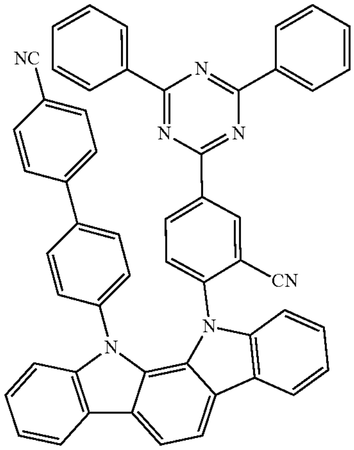
2-30
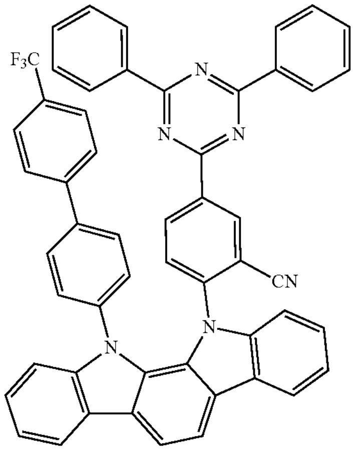
-continued
2-31
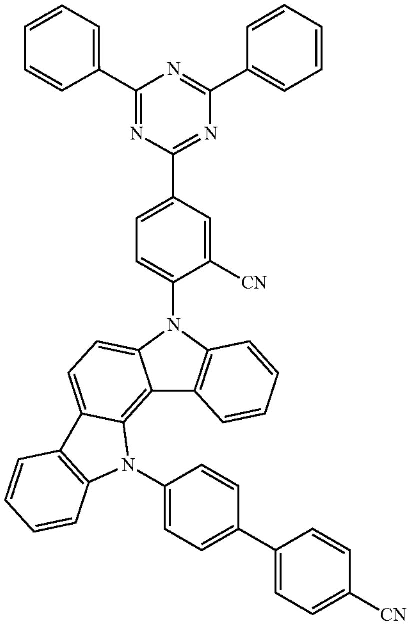
2-32
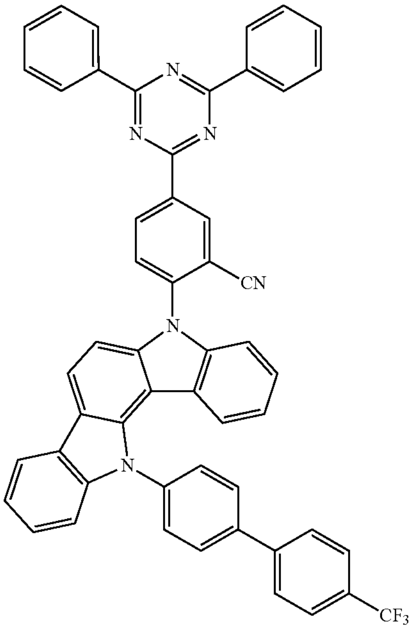

-continued
2-33
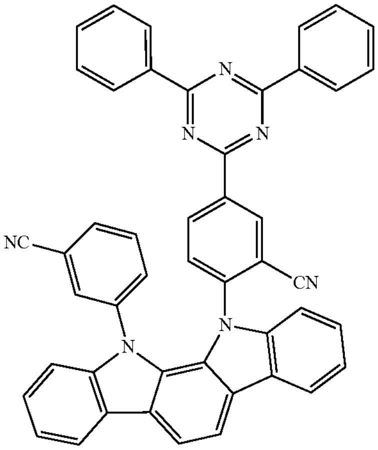
2-34
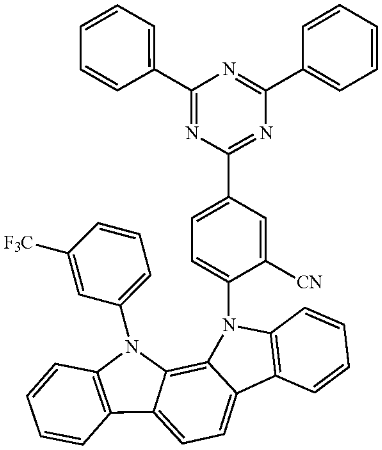
2-35
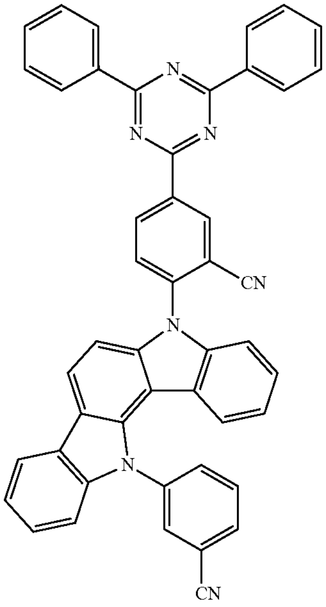
-continued
2-36
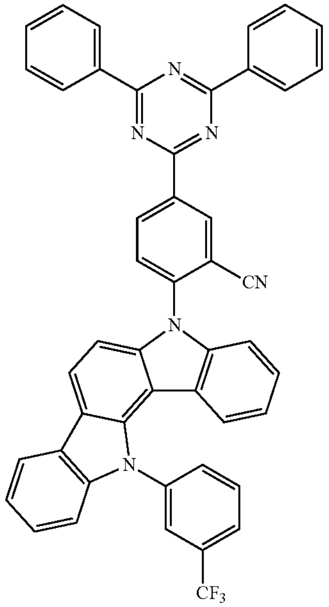
2-37
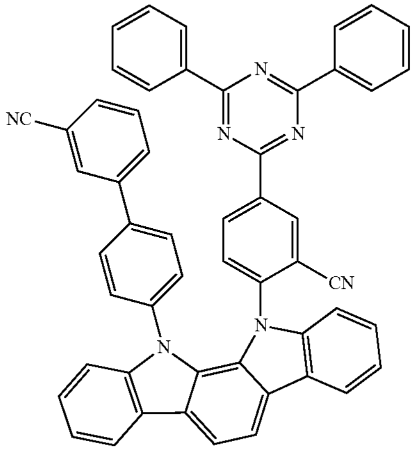
2-38
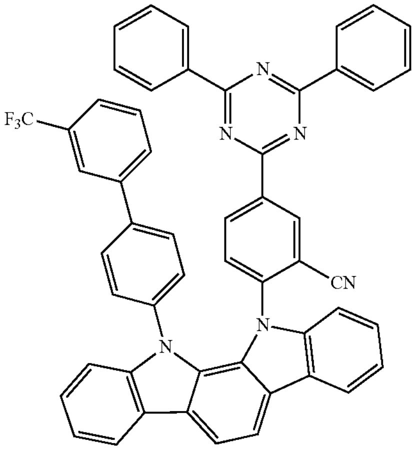

-continued
2-39
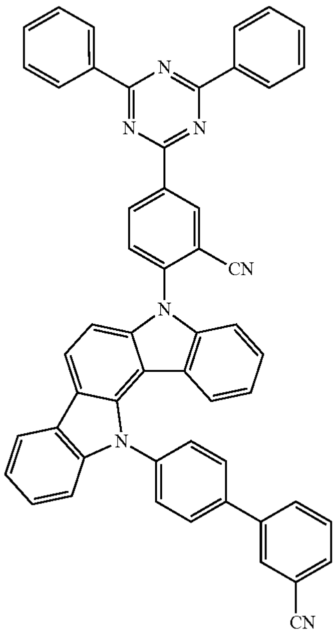
2-40
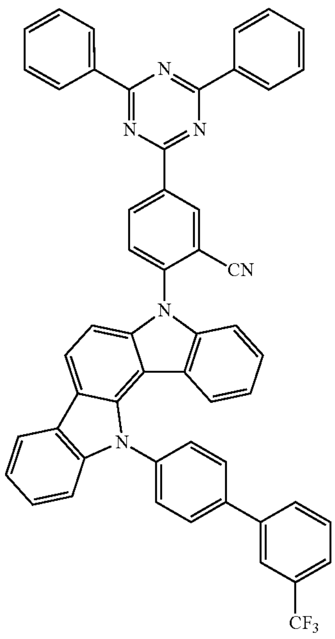
-continued
2-41
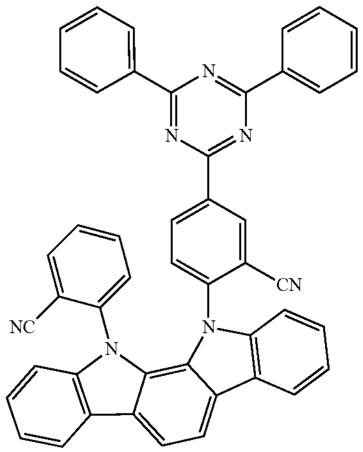
2-42
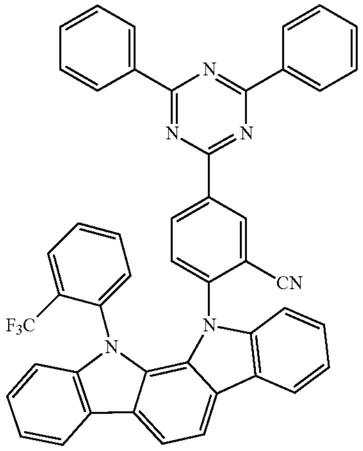
2-43
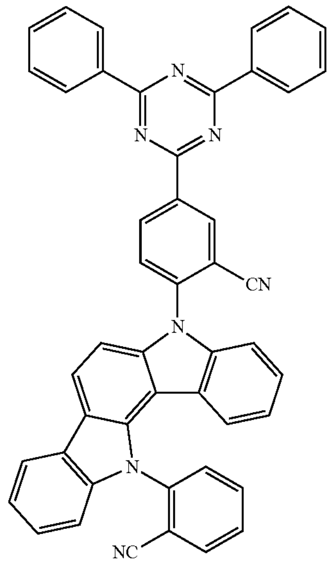

-continued
2-44
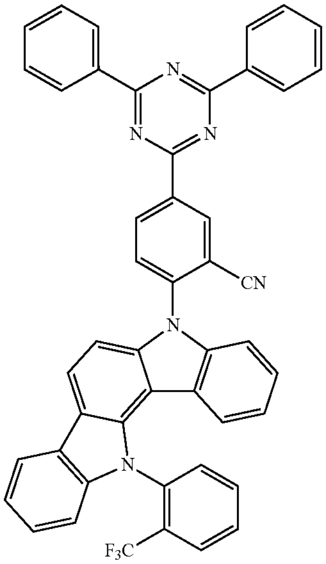
2-45
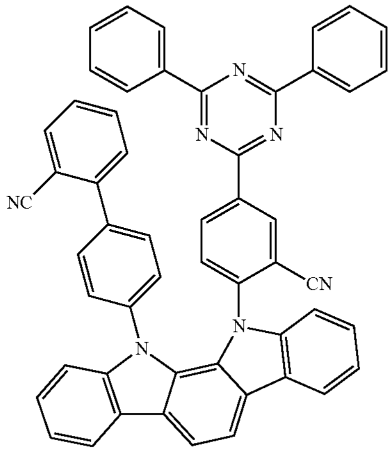
2-46
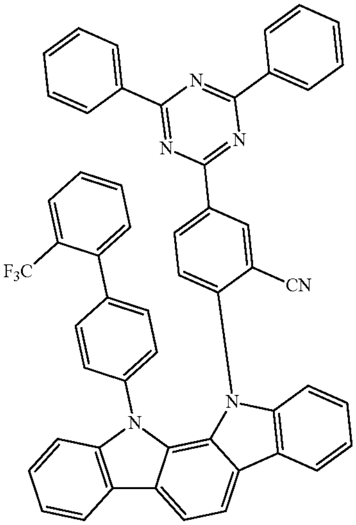
-continued
2-47
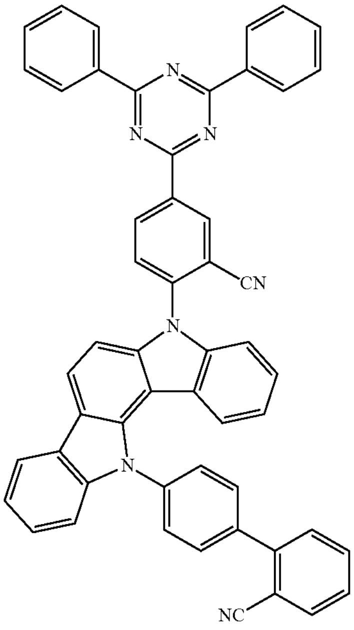
2-48
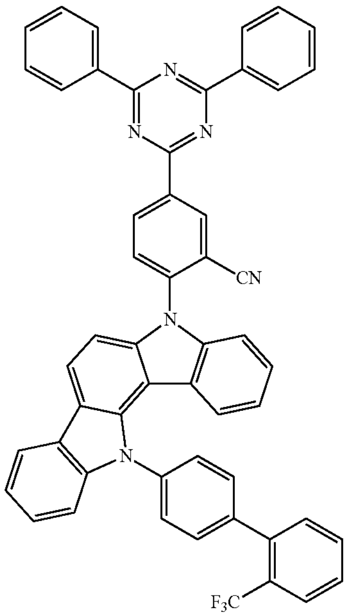

-continued
2-49
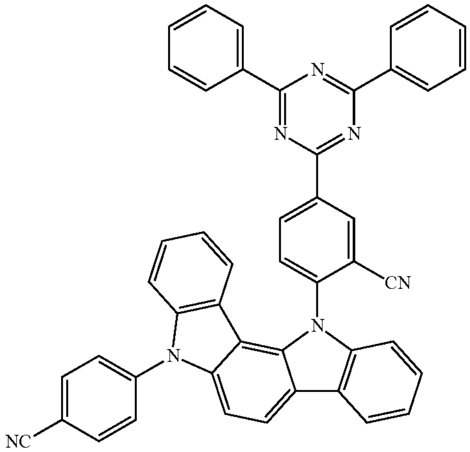
2-50
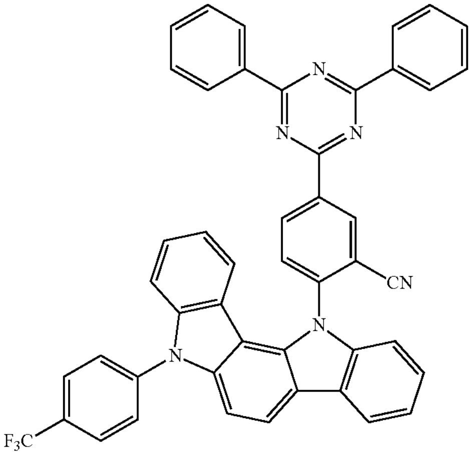
2-51
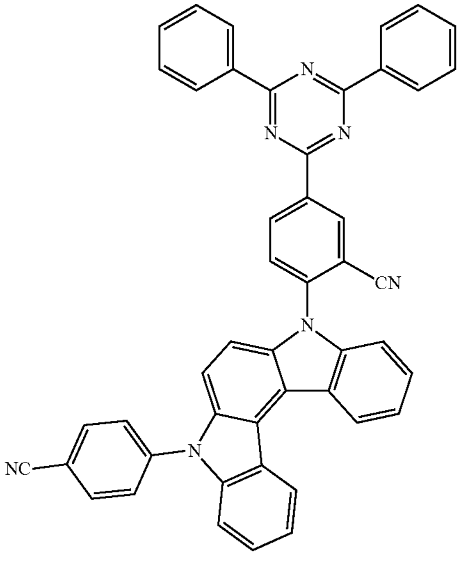
-continued
2-52
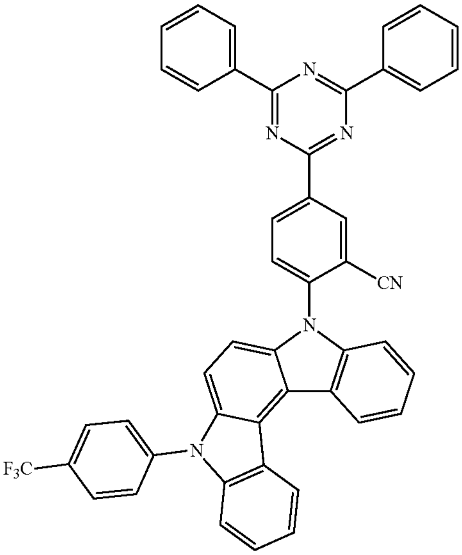
2-53
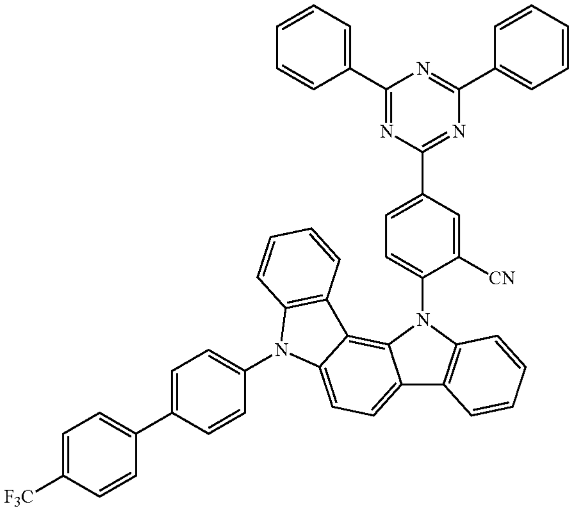
2-54
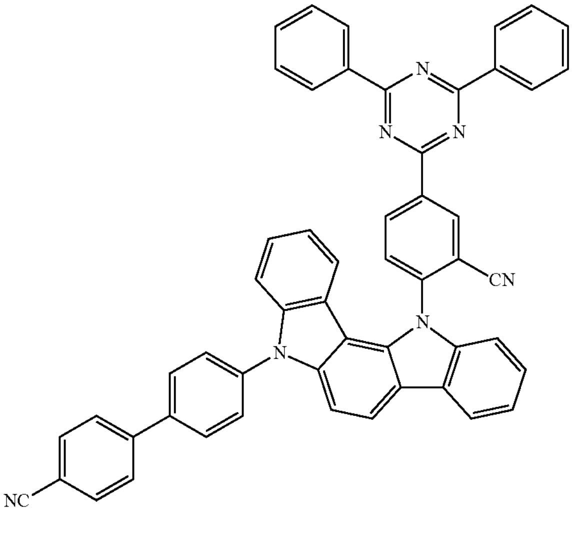

-continued
2-55
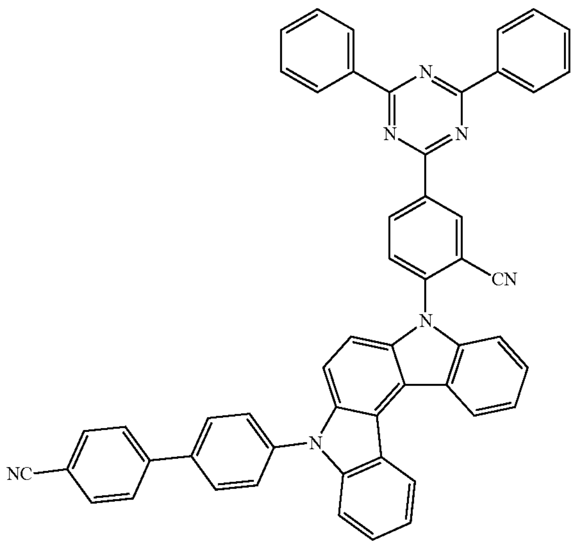
2-56
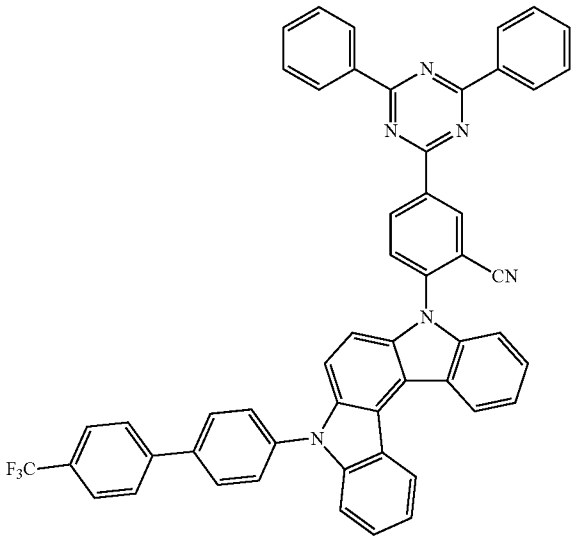
2-57
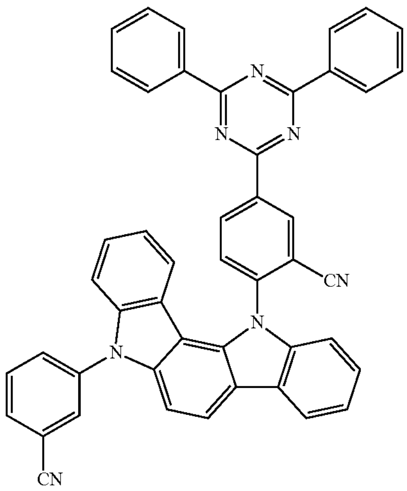
-continued
2-58
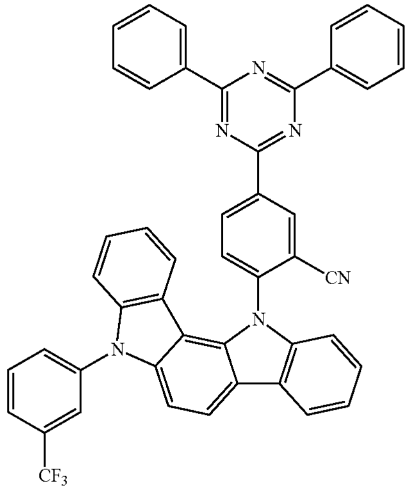
2-59
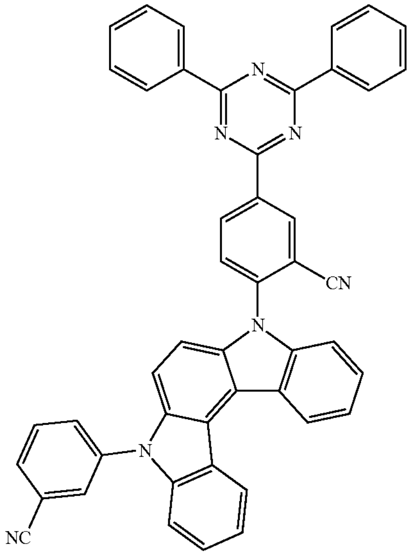
2-60
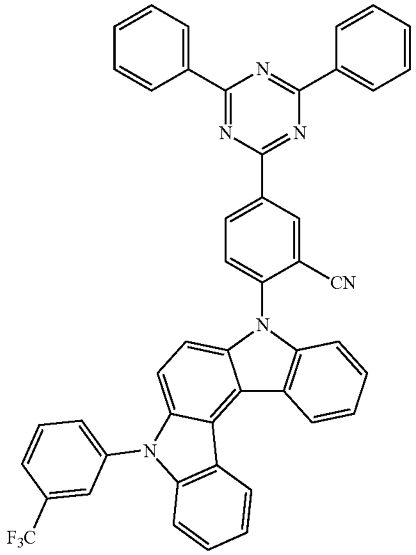

2-61
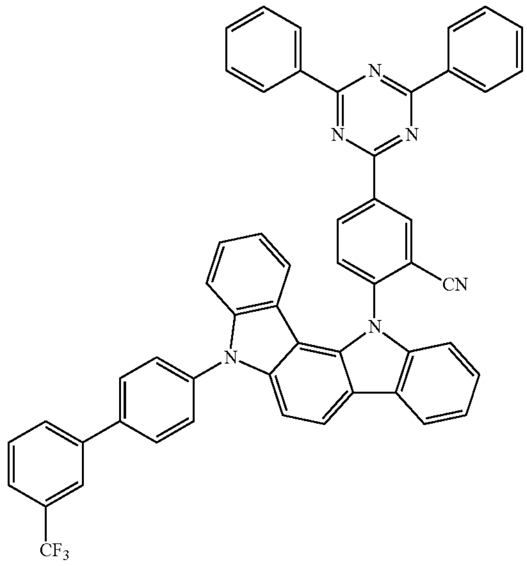
2-62
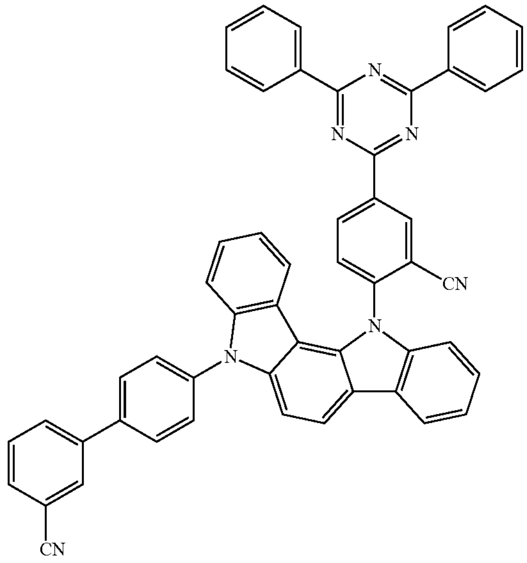
2-63
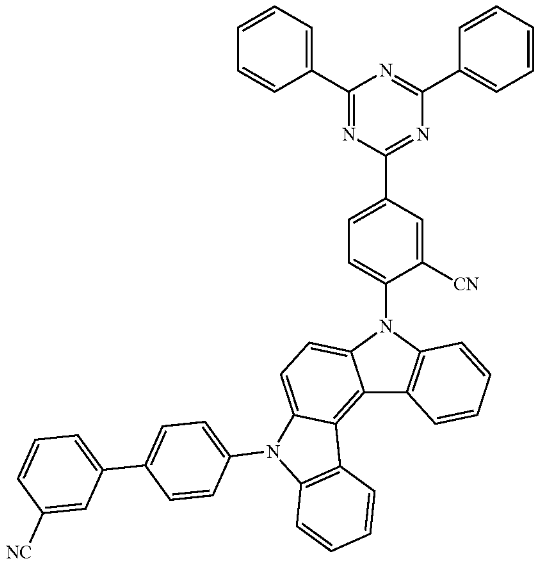
2-64
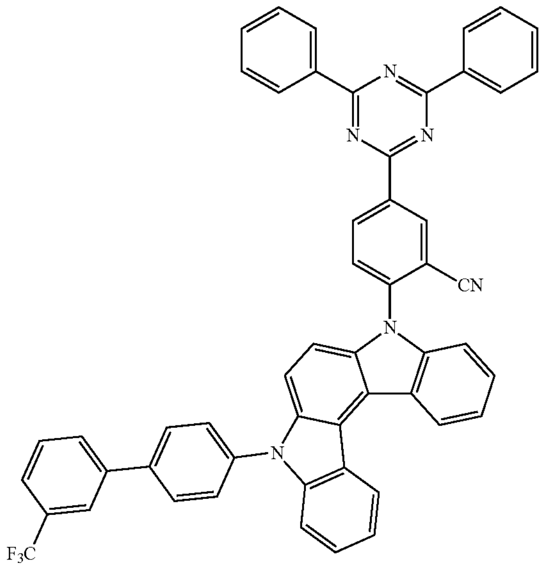
2-65
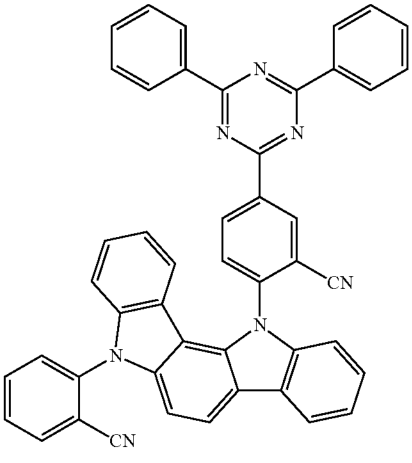

-continued
2-66
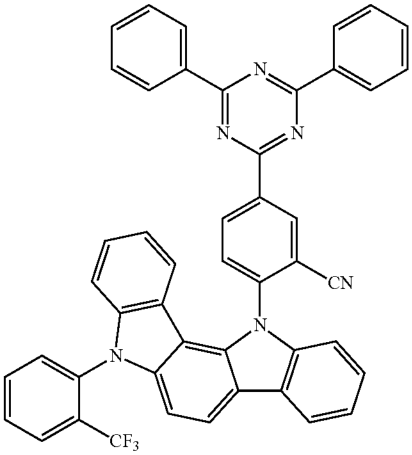
2-67
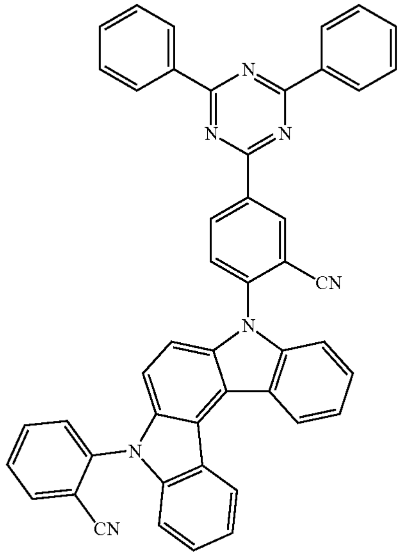
2-68
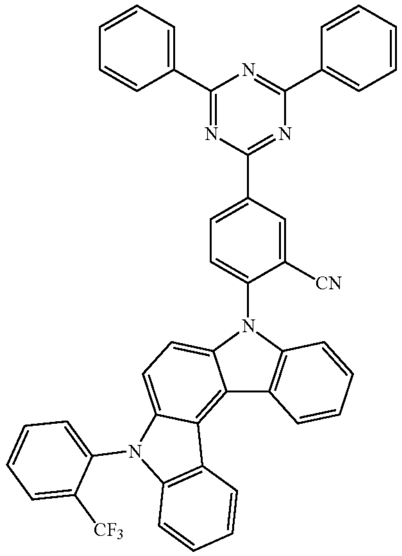
-continued
2-69
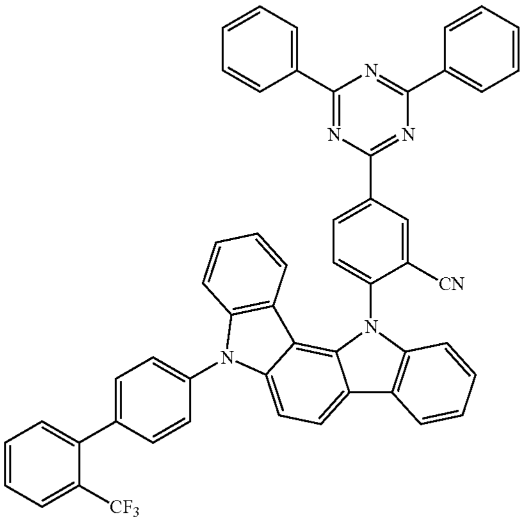
2-70
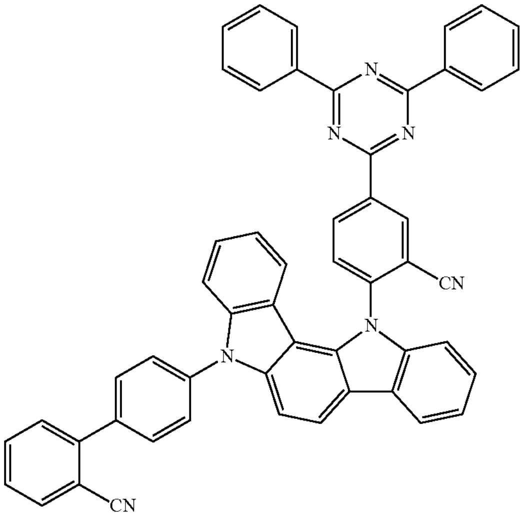
2-71
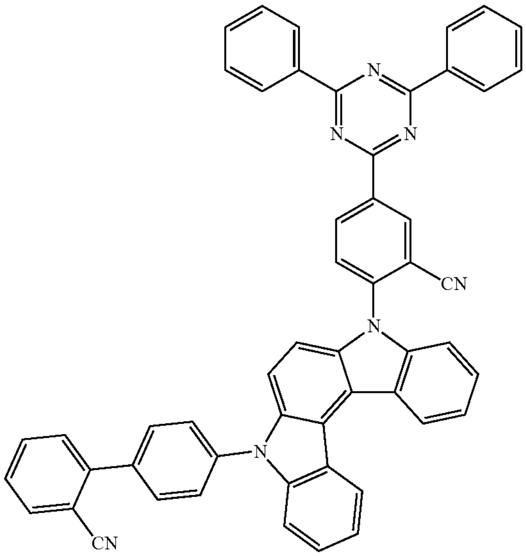

2-72
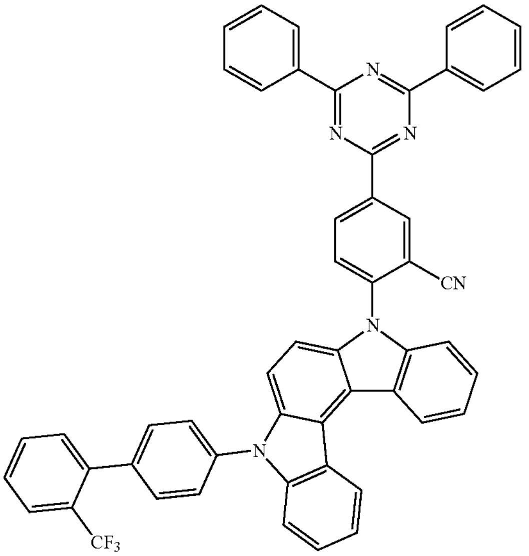
2-73
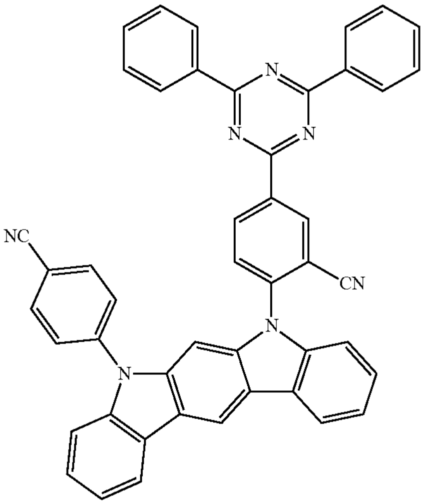
2-74
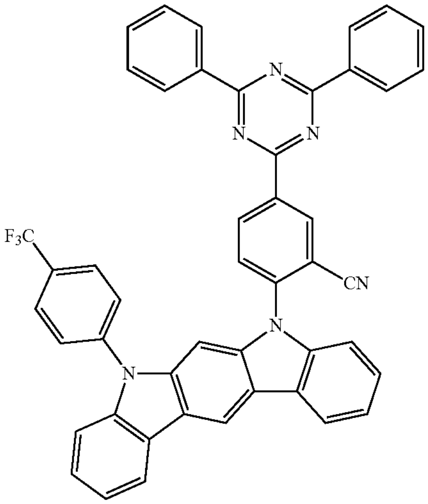
2-75
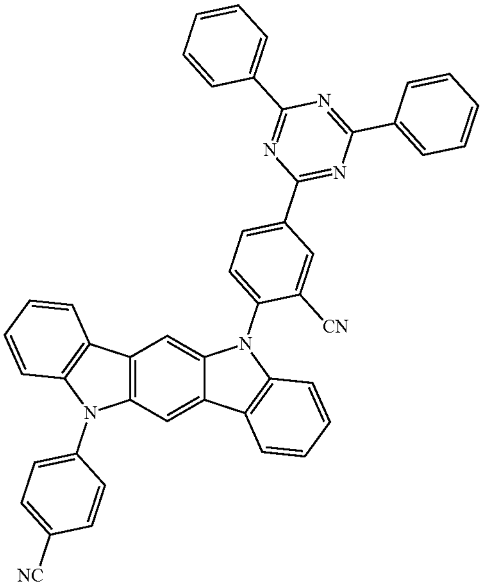
2-76
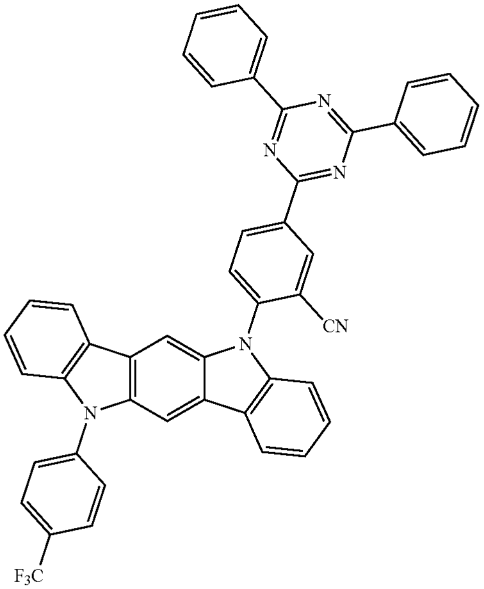

-continued
2-77
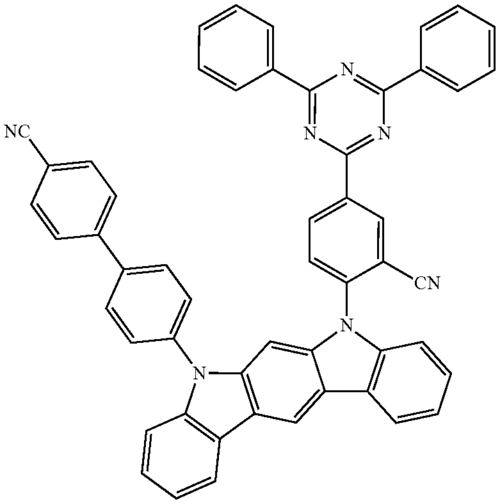
2-78
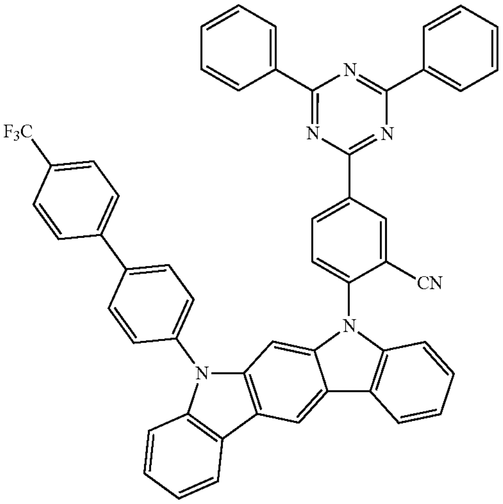
-continued
2-79
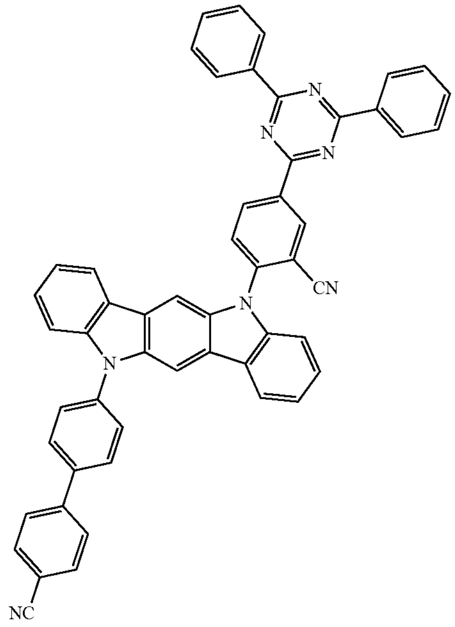
2-80
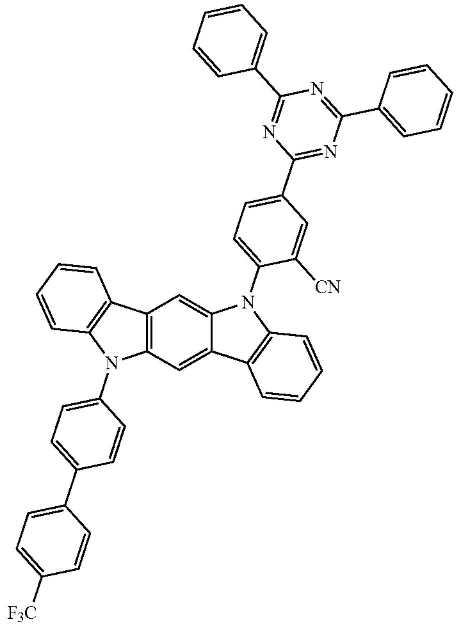

-continued
2-81
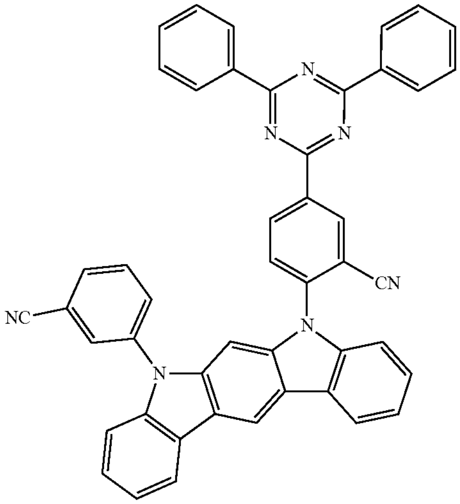
2-82
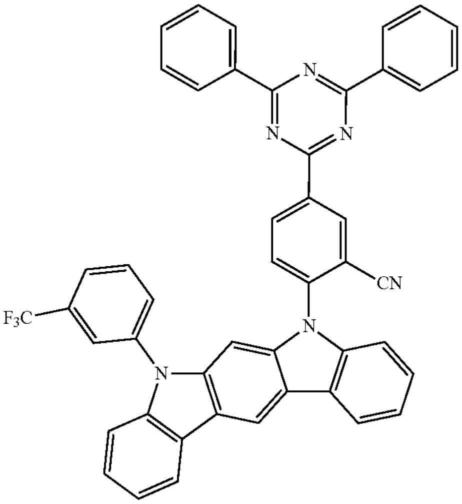
2-83
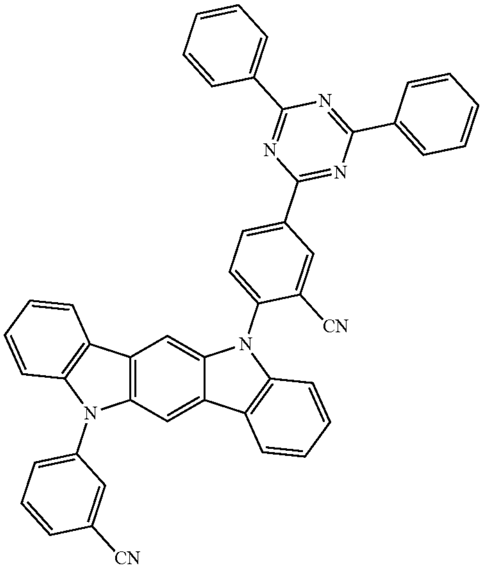
-continued
2-84
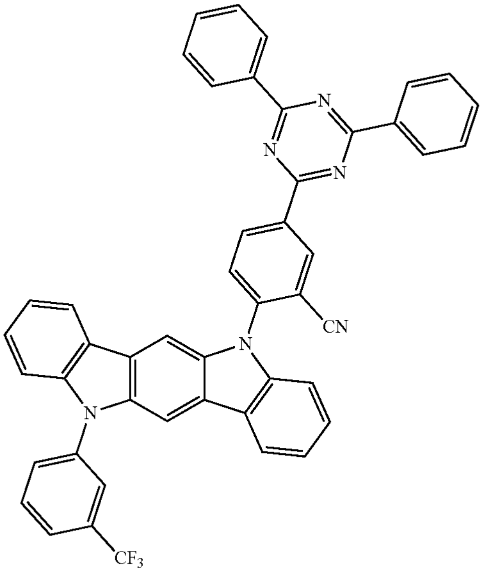
2-85
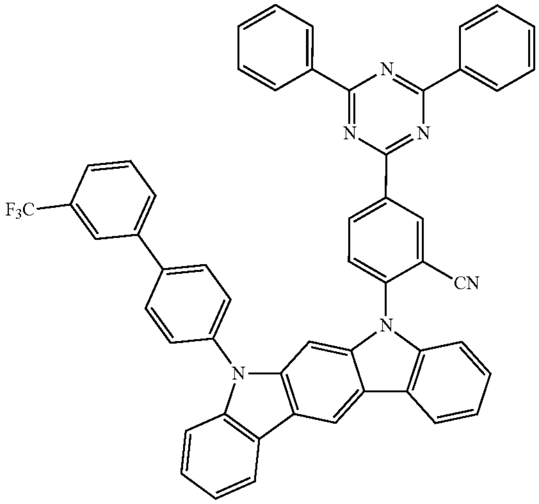
2-86
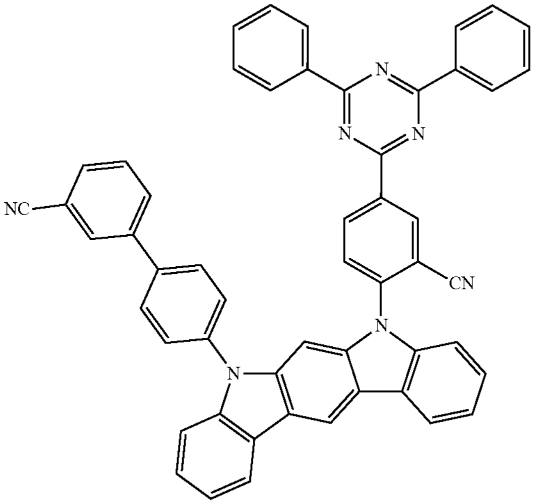

-continued
2-87
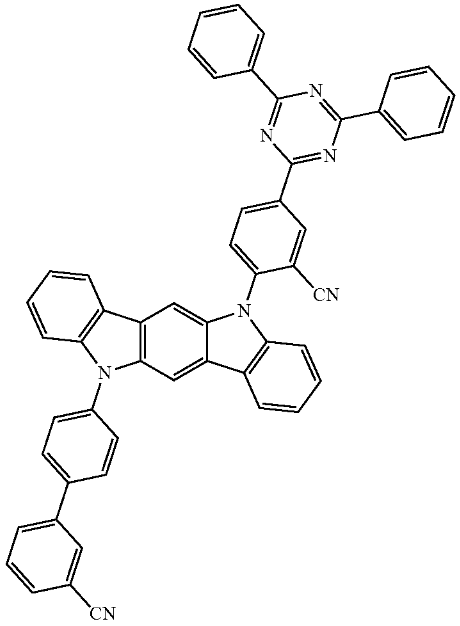
2-88
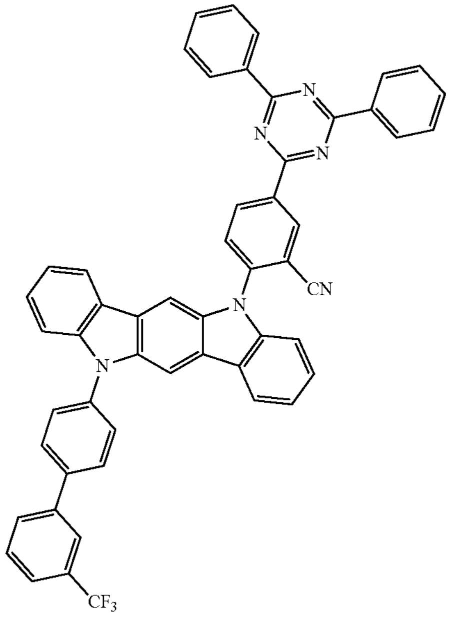
-continued
2-89
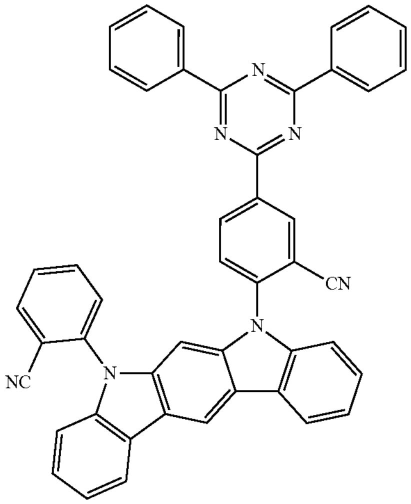
2-90
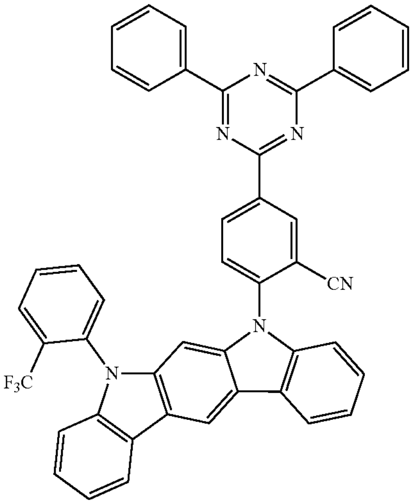
2-91
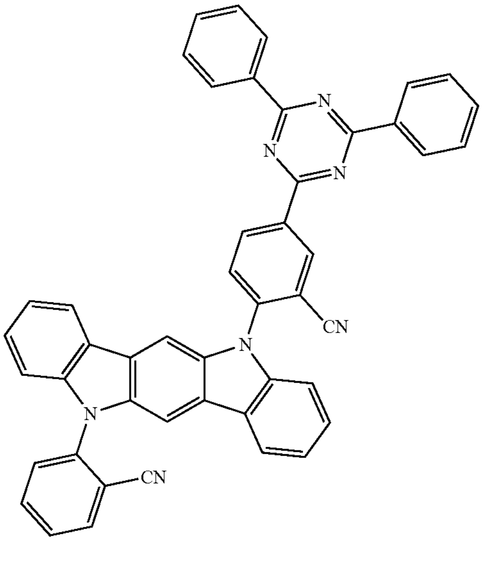

-continued 2-92

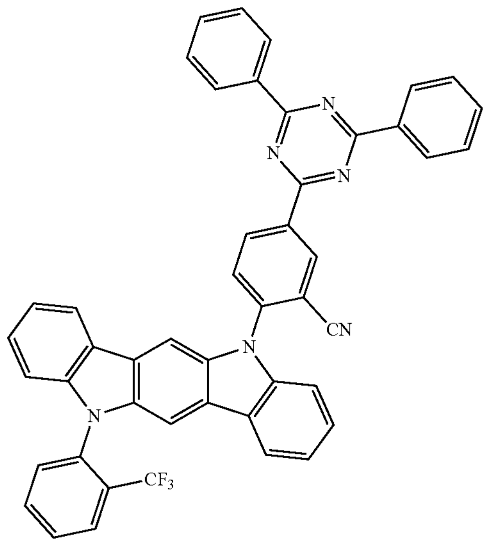

2-93

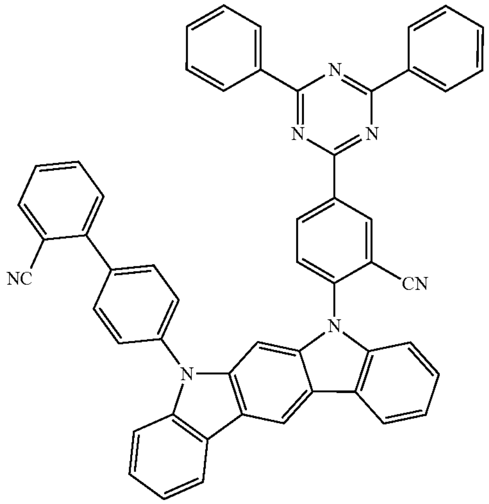

2-94

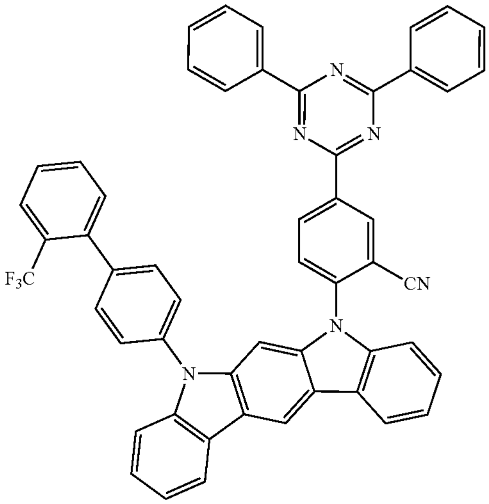

-continued 2-95

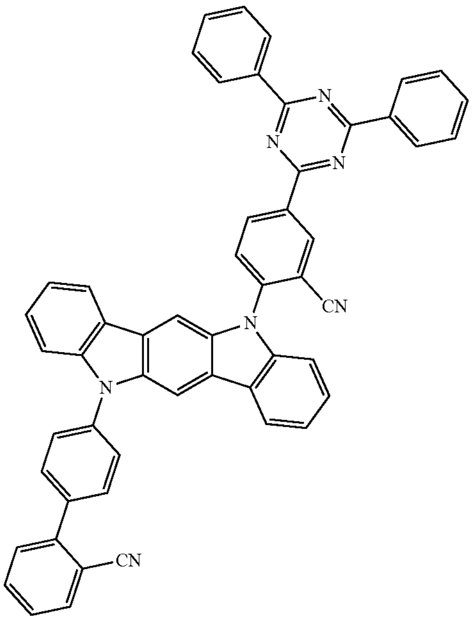

2-96

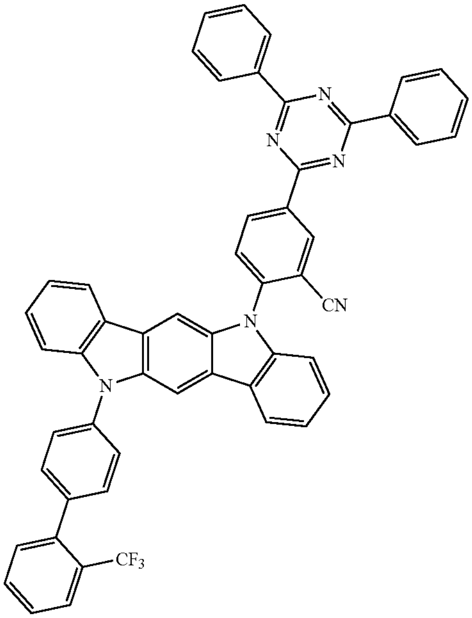

The first compound in Formula 1 emits the green light having narrow full width at half maximum (FWHM). Accordingly, the OLED D1 including the first compound provides the green emission with excellent color purity. However, since only singlet exciton of the first compound in Formula 1 being the fluorescent material is involved in the light emission, the emitting efficiency, e.g., the quantum efficiency, is lowered.

In the other hand, the energy of the triplet exciton of the second compound in Formula 2 being the delayed fluorescent material is converted into the singlet exciton by a reverse intersystem crossing (RISC) such that second compound has high quantum efficiency. However, since the second compound in Formula 2 being the delayed fluorescent material has wide FWHM, the second compound in Formula 2 being the delayed fluorescent material has a disadvantage in a color purity.

In the OLED D1 of the present disclosure, the EML 240 includes the first compound having narrow FWHM and the second compound having high quantum efficiency, the OLED D1 provides a hyper fluorescence.

Namely, the triplet exciton in the second compound is converted into the singlet exciton in the second compound, and the singlet exciton in the second compound is transferred into the first compound. The light emission is provided form the first compound so that the OLED D provides narrow FWHM and high emitting efficiency.

To increase the energy transfer efficiency from the second compound into the first compound, the overlap ratio between the absorption spectrum of the first compound and the emission spectrum of the second compound may be equal to or greater than about 35%.

The EML 240 may further include a third compound as a host. The third compound as the host may be selected from the group consisting of 9-(3-(9H-carbazol-9-yl)phenyl)-9H-carbazole-3-carbonitrile (mCP-CN), 1,3-bis(carbazol-9-yl)benzene (CBP), 3,3'-bis(N-carbazolyl)-1,1'-biphenyl (mCBP), 1,3-bis(carbazol-9-yl)benzene (mCP), oxybis(2,1-phenylene))bis(diphenylphosphine oxide) (DPEPO), 2,8-bis(diphenylphosphoryl)dibenzothiophene (PPT), 1,3,5-tri[(3-pyridyl)-phen-3-yl]benzene (TmPyPB), 2,6-di(9H-carbazol-9-yl)pyridine (PYD-2Cz), 2,8-di(9H-carbazol-9yl)dibenzothiophene (DCzDBT), 3',5'-di(carbazol-9-yl)-[1,1'-bipheyl]-3,5-dicarbonitrile (DCzTPA), 4'-(9H-carbazol-9-yl) biphenyl-3,5-dicarbonitrile (pCzB-2CN), 3'-(9H-carbazol-9-yl) biphenyl-3,5-dicarbonitrile (mCzB-2CN), diphenyl-4-triphenylsilylphenyl-phosphine oxide (TSPO1), 9-(9-phenyl-9H-carbazol-6-yl)-9H-carbazole (CCP), 4-(3-(triphenylen-2-yl)phenyl)dibenzo[b,d]thiophene), 9-(4-(9H-carbazol-9-yl)phenyl)-9H-3,9'-bicarbazole, 9-(3-(9H-carbazol-9-yl)phenyl)-9H-3,9'-bicarbazole, and 9-(6-(9H-carbazol-9-yl)pyridin-3-yl)-9H-3,9'-bicabazole, but it is not limited thereto.

For example, one of the compounds in Formula 5 as the host with the first and second compounds may be included in the EML 240.

[Formula 5]

H1

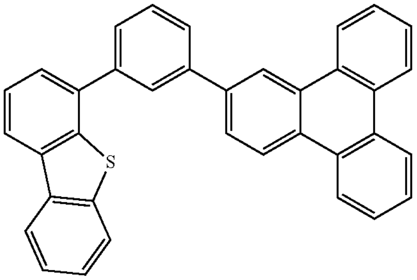

H2

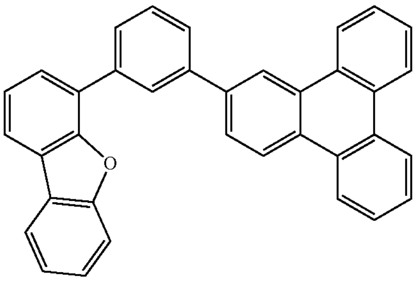

-continued

H3

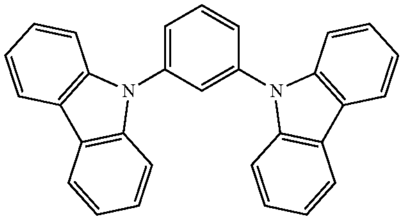

H4

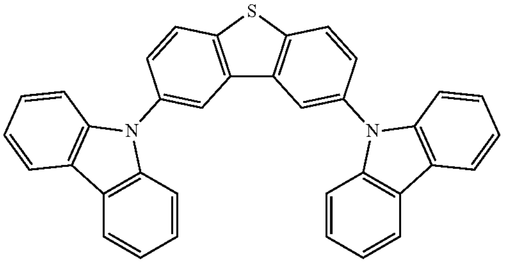

H5

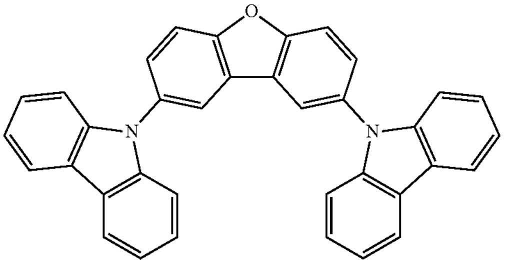

H6

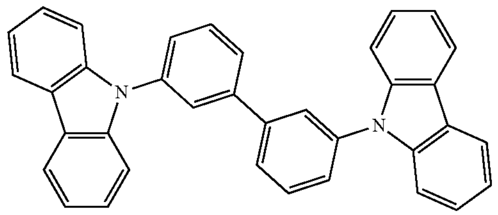

In the EML 240, the energy level of the singlet exciton of the second compound is smaller (lower) than that of the third compound as the host and is greater (higher) than that of the first compound. In addition, the energy level of the triplet exciton of the second compound is smaller than that of the third compound and is greater than the second compound.

In the EML 240, a weight % of the second compound may be greater than that of the first compound and may be equal to or smaller than that of the third compound. When the weight % of the second compound is greater than that of the first compound, the energy of the second compound is sufficiently or efficiently transferred into the first compound. For example, in the EML 240, the first compound may have a weight % of 0.1 to 10, preferably 0.1 to 5, the second compound may have a weight % of 30 to 49.9, preferably 40 to 49.9, and the third compound may have a weight % of 40 to 60. However, it is not limited thereto.

In the OLED according to the second embodiment of the present disclosure, the singlet energy level, e.g., exciton, and the triplet energy level generated in the third compound as the host are transferred into the singlet energy level and the triplet energy level of the second compound being the delayed fluorescent material. Since a difference between a singlet energy level and a triplet energy level of the second compound is relatively small, the energy of the triplet energy level of the second compound is converted into the singlet energy level of second compound by a reverse intersystem crossing (RISC). For example, the difference between a singlet energy level and a triplet energy level of the second compound may be equal to or less than about 0.3 eV. Thereafter, the singlet energy level of the second compound is transferred into the singlet energy level of the first compound, and the light emission is provided form the first compound.

As described above, the second compound having the delayed fluorescent property has high quantum efficiency. However, since the FWHM of the second compound is wide, the light emission from the second compound has poor color purity. On the other hand, the first compound having the fluorescent property has narrow FWHM. However, since the triplet exciton of the first compound is not involved in the light emission, the light emission from the first compound has low emitting efficiency.

In the OLED of the present disclosure, the energy level of the singlet exciton of the second compound being the delayed fluorescent material is transferred into the first compound being the fluorescent material, the light emission is provided from the first compound. Accordingly, the emitting efficiency and the color purity of the OLED D1 are improved. In addition, since the first compound in Formula 1 and the second compound in Formula 2 are included in the EML 240, the emitting efficiency and the color purity of the OLED D1 are further improved.

[OLED]

On an anode (ITO, 70 nm), an HIL (the compound in Formula 6-1, 10 nm), an HTL (the compound in Formula 6-2, 140 nm), an EBL (the compound in Formula 6-3, 10 nm), an EML (40 nm), an HBL (the compound in Formula 6-4, 10 nm), an ETL (the compound in Formula 6-5, 30 nm), an EIL (Liq, 1 nm) and a cathode (Mg:Ag, 10 nm) are sequentially stacked to form the OLED.

[Formula 6-1]

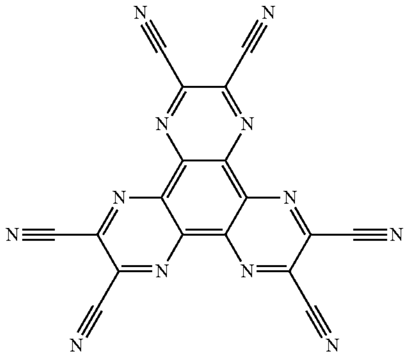

[Formula 6-2]

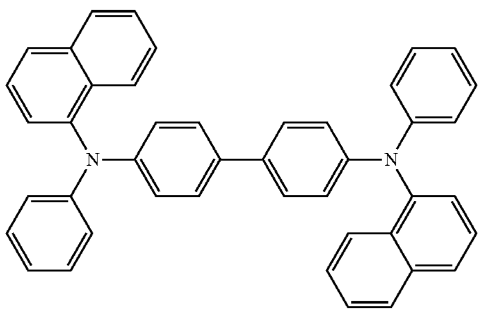

-continued

[Formula 6-3]

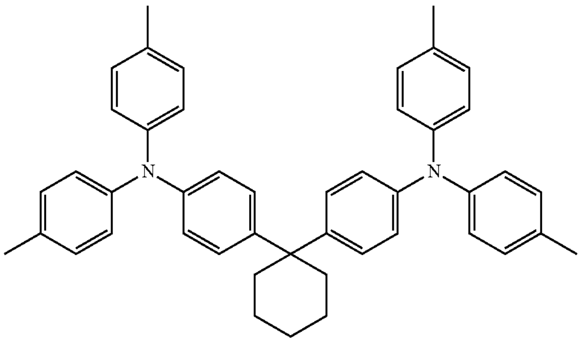

[Formula 6-4]

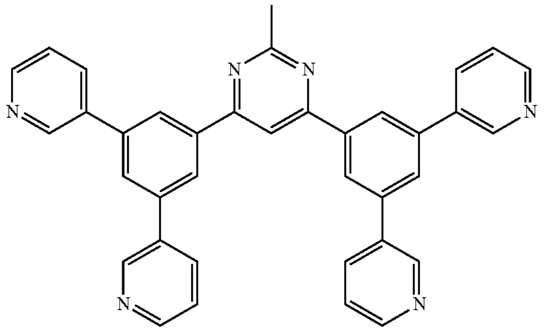

[Formula 6-5]

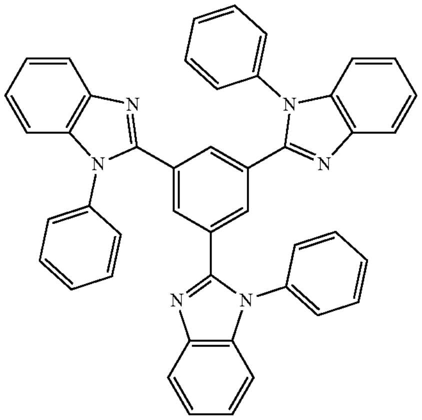

(1) Comparative Example 1 (Ref1)

The compound H6 in Formula 5 (49.9 wt %) as the host, the compound 1-1 in Formula 3 (0.2 wt %) and the compound in Formula 7-1 (49.9 wt %) are used to form the EML.

(2) Comparative Example 2 (Ref2)

The compound H6 in Formula 5 (49.9 wt %) as the host, the compound 1-1 in Formula 3 (0.2 wt %) and the compound in Formula 7-2 (49.9 wt %) are used to form the EML.

(3) Comparative Example 3 (Ref3)

The compound H6 in Formula 5 (49.9 wt %) as the host, the compound 1-4 in Formula 3 (0.2 wt %) and the compound in Formula 7-1 (49.9 wt %) are used to form the EML.

(4) Comparative Example 4 (Ref4)

The compound H6 in Formula 5 (49.9 wt %) as the host, the compound 1-4 in Formula 3 (0.2 wt %) and the compound in Formula 7-2 (49.9 wt %) are used to form the EML.

(5) Example 1 (Ex1)

The compound H6 in Formula 5 (49.9 wt %) as the host, the compound 1-1 in Formula 3 (0.2 wt %) and the compound 2-1 in Formula 4 (49.9 wt %) are used to form the EML.

(6) Example 2 (Ex2)

The compound H6 in Formula 5 (49.9 wt %) as the host, the compound 1-1 in Formula 3 (0.2 wt %) and the compound 2-2 in Formula 4 (49.9 wt %) are used to form the EML.

(7) Example 3 (Ex3)

The compound H6 in Formula 5 (49.9 wt %) as the host, the compound 1-1 in Formula 3 (0.2 wt %) and the compound 2-3 in Formula 4 (49.9 wt %) are used to form the EML.

(8) Example 4 (Ex4)

The compound H6 in Formula 5 (49.9 wt %) as the host, the compound 1-1 in Formula 3 (0.2 wt %) and the compound 2-4 in Formula 4 (49.9 wt %) are used to form the EML.

(9) Example 5 (Ex5)

The compound H6 in Formula 5 (49.9 wt %) as the host, the compound 1-1 in Formula 3 (0.2 wt %) and the compound 2-9 in Formula 4 (49.9 wt %) are used to form the EML.

(10) Example 6 (Ex6)

The compound H6 in Formula 5 (49.9 wt %) as the host, the compound 1-1 in Formula 3 (0.2 wt %) and the compound 2-10 in Formula 4 (49.9 wt %) are used to form the EML.

(11) Example 7 (Ex7)

The compound H6 in Formula 5 (49.9 wt %) as the host, the compound 1-1 in Formula 3 (0.2 wt %) and the compound 2-11 in Formula 4 (49.9 wt %) are used to form the EML.

(12) Example 8 (Ex8)

The compound H6 in Formula 5 (49.9 wt %) as the host, the compound 1-1 in Formula 3 (0.2 wt %) and the compound 2-12 in Formula 4 (49.9 wt %) are used to form the EML.

(13) Example 9 (Ex9)

The compound H6 in Formula 5 (49.9 wt %) as the host, the compound 1-4 in Formula 3 (0.2 wt %) and the compound 2-1 in Formula 4 (49.9 wt %) are used to form the EML.

(14) Example 10 (Ex10)

The compound H6 in Formula 5 (49.9 wt %) as the host, the compound 1-4 in Formula 3 (0.2 wt %) and the compound 2-2 in Formula 4 (49.9 wt %) are used to form the EML.

(15) Example 11 (Ex11)

The compound H6 in Formula 5 (49.9 wt %) as the host, the compound 1-4 in Formula 3 (0.2 wt %) and the compound 2-3 in Formula 4 (49.9 wt %) are used to form the EML.

(16) Example 12 (Ex12)

The compound H6 in Formula 5 (49.9 wt %) as the host, the compound 1-4 in Formula 3 (0.2 wt %) and the compound 2-4 in Formula 4 (49.9 wt %) are used to form the EML.

(17) Example 13 (Ex13)

The compound H6 in Formula 5 (49.9 wt %) as the host, the compound 1-4 in Formula 3 (0.2 wt %) and the compound 2-9 in Formula 4 (49.9 wt %) are used to form the EML.

(18) Example 14 (Ex14)

The compound H6 in Formula 5 (49.9 wt %) as the host, the compound 1-4 in Formula 3 (0.2 wt %) and the compound 2-10 in Formula 4 (49.9 wt %) are used to form the EML.

(19) Example 15 (Ex15)

The compound H6 in Formula 5 (49.9 wt %) as the host, the compound 1-4 in Formula 3 (0.2 wt %) and the compound 2-11 in Formula 4 (49.9 wt %) are used to form the EML.

(20) Example 16 (Ex16)

The compound H6 in Formula 5 (49.9 wt %) as the host, the compound 1-4 in Formula 3 (0.2 wt %) and the compound 2-12 in Formula 4 (49.9 wt %) are used to form the EML.

[Formula 7-1]

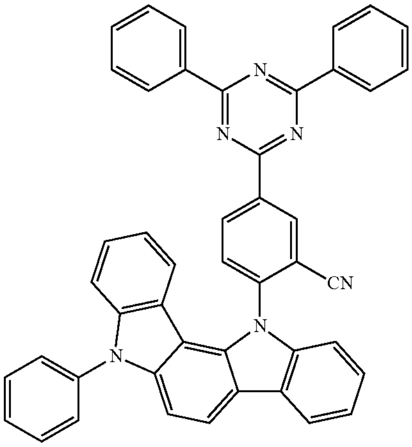

[Formula 7-2]

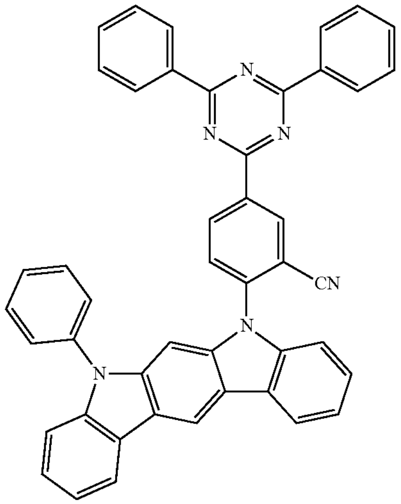

The emitting properties, i.e., the driving voltage "V", the current efficiency "cd/A", the maximum emission peak of the delayed fluorescent material "TDEL", the maximum absorption peak of the fluorescent material "FDabs" and the overlap ratio between the maximum emission peak of the delayed fluorescent material and the maximum absorption peak of the fluorescent material "Overlap (%)", of the OLED in to Ref4 and Ex1 to Ex16 are measured and listed in Table 1.

TABLE 1

| | V | cd/A | λmax | | Overlap |
|---|---|---|---|---|---|
| | | | $TD_{EL}$ | $FD_{abs}$ | (%) |
| Ref1 | 3.7 | 88 | 528 | 516 | 31 |
| Ref2 | 3.7 | 75 | 530 | | 28 |
| Ex1 | 3.8 | 143 | 514 | | 37 |
| Ex2 | 3.8 | 151 | 516 | | 38 |
| Ex3 | 3.8 | 140 | 516 | | 38 |
| Ex4 | 3.7 | 143 | 518 | | 37 |
| Ex5 | 3.6 | 138 | 518 | | 37 |
| Ex6 | 3.7 | 137 | 518 | | 37 |
| Ex7 | 3.8 | 138 | 521 | | 36 |
| Ex8 | 3.7 | 132 | 522 | | 35 |
| Ref3 | 3.8 | 91 | 528 | 518 | 32 |
| Ref4 | 3.8 | 76 | 530 | | 29 |

TABLE 1-continued

| | V | cd/A | λmax | | Overlap |
|---|---|---|---|---|---|
| | | | $TD_{EL}$ | $FD_{abs}$ | (%) |
| Ex9 | 3.9 | 145 | 514 | | 37 |
| Ex10 | 3.8 | 143 | 516 | | 37 |
| Ex11 | 3.9 | 138 | 516 | | 38 |
| Ex12 | 3.8 | 145 | 518 | | 38 |
| Ex13 | 3.6 | 141 | 518 | | 38 |
| Ex14 | 3.8 | 140 | 518 | | 38 |
| Ex15 | 3.8 | 139 | 521 | | 37 |
| Ex16 | 3.8 | 136 | 522 | | 36 |

As shown in Table 1, in comparison to the OLED of to Ref4, the emitting efficiency of the OLED of Ex1 to Ex16, which includes the first compound in Formula 1 and the second compound in Formula 2, is significantly increased.

Figure 4:
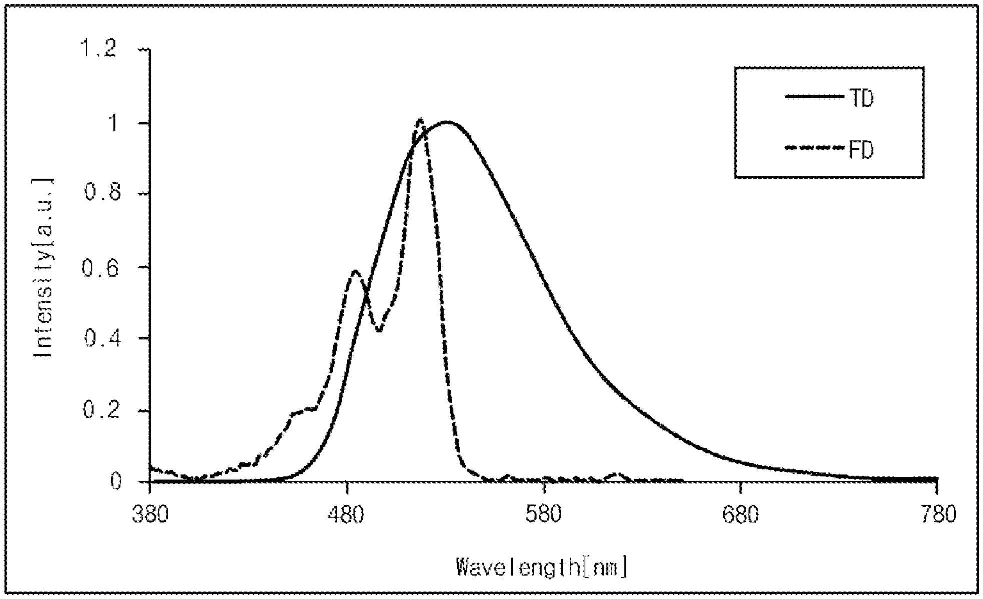
FIG. 4 is a view illustrating a relation between an absorption spectrum of a fluorescent material and an emission spectrum of a delayed fluorescent material in an OLED.

Referring to FIG. 4, which is a view illustrating a relation between an absorption spectrum of a fluorescent material and an emission spectrum of a delayed fluorescent material in an OLED, the maximum emission wavelength, e.g., a peak wavelength, of the delayed fluorescent material, i.e., the compound in Formula 7-1, "TD" and the maximum absorption wavelength, i.e., the compound 1-1 in Formula 3, "FD" have a difference above about 10 nm. As a result, the overlap ratio between the maximum emission wavelength of the delayed fluorescent material, i.e., the compound in Formula 7-1, "TD" and the maximum absorption wavelength, i.e., the compound 1-1 in Formula 3, "FD" is relatively small, e.g., about 31%.

Figure 5:
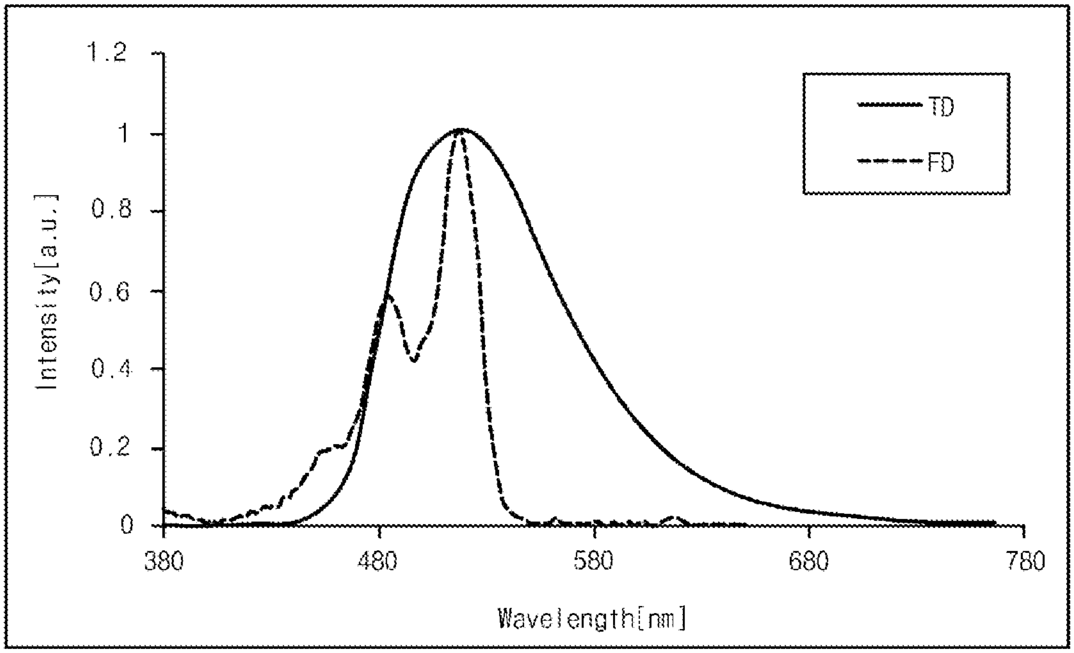
FIG. 5 is a view illustrating a relation between an absorption spectrum of a fluorescent material and an emission spectrum of a delayed fluorescent material in the OLED according to the second embodiment of the present disclosure.

On the other hand, in the second compound in Formula 2, the electron withdrawing group X and the indolocarbazole moiety are linked via a linker L or directly so that the emission peak of the second compound is shifted into a short wavelength. Referring to FIG. 5, which is a view illustrating a relation between an absorption spectrum of a fluorescent material and an emission spectrum of a delayed fluorescent material in the OLED according to the second embodiment of the present disclosure, the overlap ratio between the maximum emission wavelength of the delayed fluorescent material, i.e., the compound 2-1 in Formula 4, "TD" and the maximum absorption wavelength, i.e., the compound 1-1 in Formula 3, "FD" is increased, e.g., about 37%.

Accordingly, the emitting efficiency of the OLED, which includes the first compound in Formula 1 and the second compound in Formula 2, is significantly increased.

Figure 6:
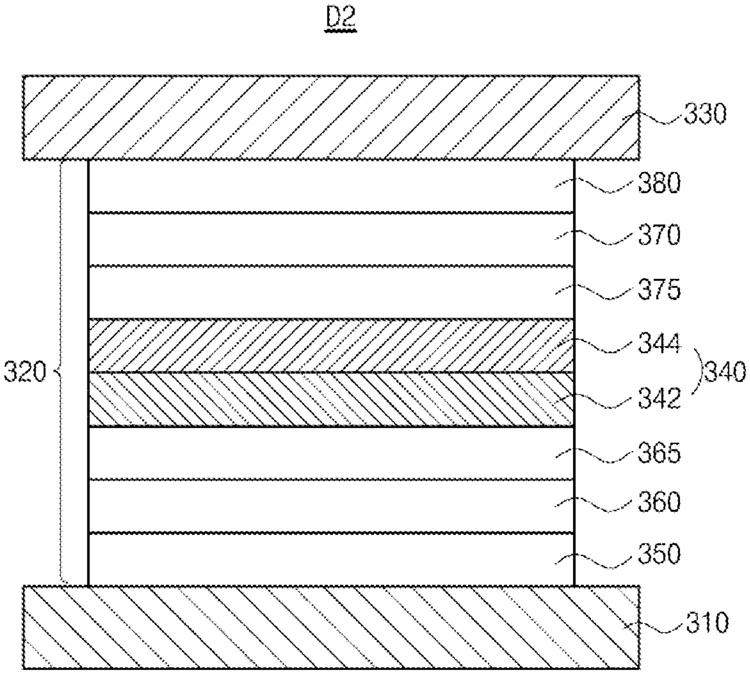
FIG. 6 is a schematic cross-sectional view of an OLED according to a third embodiment of the present disclosure.

FIG. 6 is a schematic cross-sectional view of an OLED according to a third embodiment of the present disclosure.

As shown in FIG. 6, an OLED D2 according to the third embodiment of the present disclosure includes the first and second electrodes 310 and 330, which face each other, and the light emitting layer 320 therebetween. The light emitting layer 320 includes an EML 340. The organic light emitting display device 100 (of FIG. 2) may include a red pixel region, a green pixel region and a blue pixel region, and the OLED D2 may be positioned in the green pixel region.

The first electrode 310 may be an anode, and the second electrode 330 may be a cathode.

The light emitting layer 320 may further include at least one of the HTL 360 between the first electrode 310 and the EML 340 and the ETL 370 between the second electrode 330 and the EML 340.

In addition, the light emitting layer 320 may further include at least one of the HIL 350 between the first electrode 310 and the HTL 360 and the EIL 380 between the second electrode 330 and the ETL 370.

Moreover, the light emitting layer 320 may further include at least one of the EBL 365 between the HTL 360 and the EML 340 and the HBL 375 between the EML 340 and the ETL 370.

The EML 340 includes a first EML (a first layer or a lower emitting material layer) 342 and a second EML (a second layer or an upper emitting material layer) 344 sequentially stacked over the first electrode 310. Namely, the second EML 344 is positioned between the first EML 342 and the second electrode 330.

In the EML 340, one of the first and second EMLs 342 and 344 includes the first compound being the fluorescent material in Formulas 1 and 3, and the other one of the first and second EMLs 342 and 344 includes the second compound being the delayed fluorescent material in Formulas 2 and 4. In addition, the first and second EMLs 342 and 344 further include a fourth compound and a fifth compound as a host, respectively. The fourth compound in the first EML 342 and the fifth compound in the second EML 344 may be same or different. For example, each of the host of the first EML 342, i.e., the fourth compound, and the host of the second EML 344, i.e., the fifth compound, may be the above third compound.

The OLED, where the first EML 342 includes the first compound, will be explained.

The second compound having a delayed fluorescent property has high quantum efficiency. However, since the second compound has wide FWHM, the second compound has a disadvantage in a color purity. On other hand, the first compound having a fluorescent property has narrow FWHM. However, the triplet exciton of the first compound is not involved in the light emission, the first compound has a disadvantage in an emitting efficiency.

In the OLED D2, since the triplet exciton energy of the second compound in the second EML 344 is converted into the singlet exciton energy of the second compound by the RISC, and the singlet exciton energy of the second compound is transferred into the singlet exciton energy of the first compound in the first EML 342. As a result, the first compound provides the light emission. Accordingly, both the singlet exciton energy and the triplet exciton energy are involved in the light emission such that the emitting efficiency is improved. In addition, since the emission is provided from the first compound of the fluorescent material, the light emission having narrow FWHM is provided.

As described above, the absorption spectrum of the first compound and the emission spectrum of the second compound have an overlap ratio being equal to or greater than about 35%. Accordingly, the energy of the second compound in the second EML 344 is efficiently transferred into the first compound in the first EML 342 such that the emitting efficiency of the OLED D2 is further improved.

In the first EML 342, a weight % of the fourth compound may be equal to or greater than that of the first compound. In addition, in the second EML 344, the weight % of the fifth compound may be equal to or greater than the second compound. The weight % of the first compound in the first EML 342 may be smaller than that of the second compound in the second EML 344. As a result, the energy transfer by the FRET from the second compound in the second EML 344 into the first compound in the first EML 342 may be sufficiently or efficiently generated. For example, the weight % of the first compound in the first EML 342 may be 0.01 to 10, preferably 0.1 to 5, and the weight % of the second compound in the second EML 344 may be 30 to 50, preferably 40 to 50.

The host in the first EML 342 may be same as a material of the EBL 365. In this instance, the first EML342 may have an electron blocking function with an emission function. Namely, the first EML 342 may serve as a buffer layer for blocking the electron. When the EBL 365 is omitted, the first EML 342 may serve as an emitting material layer and an electron blocking layer.

When the first compound in included in the second EML 344 and the second compound is included in the first EML 342, the host in the second EML 344 may be same as a material of the HBL 375. In this instance, the second EML344 may have a hole blocking function with an emission function. Namely, the second EML 344 may serve as a buffer layer for blocking the hole. When the HBL 375 is omitted, the second EML 344 may serve as an emitting material layer and a hole blocking layer.

Figure 7:
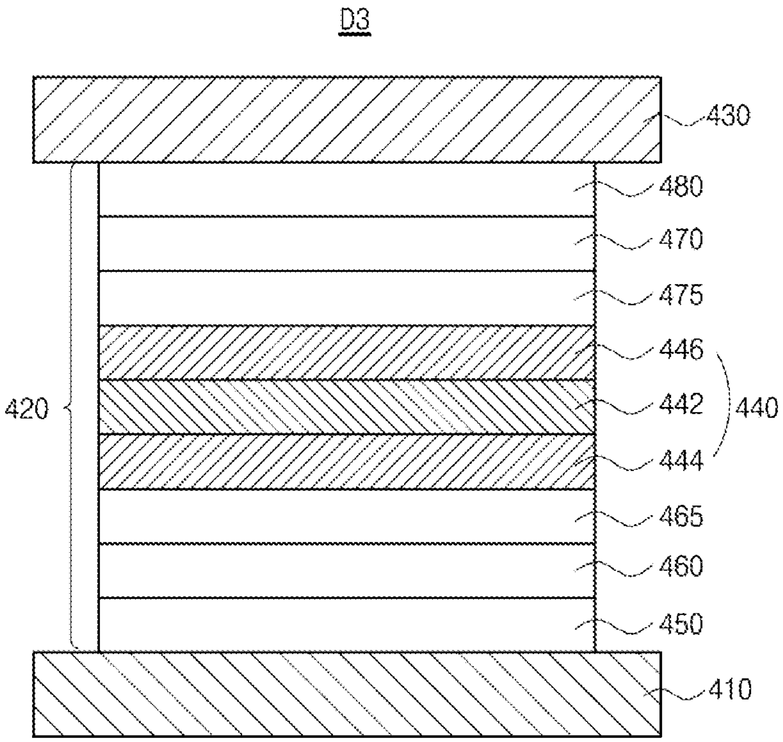
FIG. 7 is a schematic cross-sectional view of an OLED according to a fourth embodiment of the present disclosure.

FIG. 7 is a schematic cross-sectional view of an OLED according to a fourth embodiment of the present disclosure.

As shown in FIG. 7, an OLED D3 according to the fourth embodiment of the present disclosure includes the first and second electrodes 410 and 430, which face each other, and the light emitting layer 420 therebetween. The light emitting layer 420 includes an EML 440. The organic light emitting display device 100 (of FIG. 2) may include a red pixel region, a green pixel region and a blue pixel region, and the OLED D3 may be positioned in the green pixel region.

The first electrode 410 may be an anode, and the second electrode 430 may be a cathode.

The light emitting layer 420 may further include at least one of the HTL 460 between the first electrode 410 and the EML 440 and the ETL 470 between the second electrode 430 and the EML 440.

In addition, the light emitting layer 420 may further include at least one of the HIL 450 between the first electrode 410 and the HTL 460 and the EIL 480 between the second electrode 430 and the ETL 470.

Moreover, the light emitting layer 420 may further include at least one of the EBL 465 between the HTL 460 and the EML 440 and the HBL 475 between the EML 440 and the ETL 470.

The EML 440 includes a first EML (a first layer, an intermediate emitting material layer) 442, a second EML (a second layer, a lower emitting material layer) 444 between the first EML 442 and the first electrode 410, and a third EML (a third layer, an upper emitting material layer) 446 between the first EML 442 and the second electrode 430. Namely, the EML 440 has a triple-layered structure of the second EML 444, the first EML 442 and the third EML 446 sequentially stacked.

For example, the first EML 442 may be positioned between the EBL 465 and the HBL 475, the second EML 444 may be positioned between the EBL 465 and the first EML 442, and the third EML 446 may be positioned between the HBL 475 and the first EML 442.

The first EML 442 includes the second compound being the delayed fluorescent material in Formulas 2 and 4, and each of the second and third EMLs 444 and 446 includes the first compound being the fluorescent material in Formulas 1 and 3. The first compound in the first EML 444 and the first compound in the third EML 446 may be same or different. In addition, the first to third EMLs 442, 444 and 446 further include a sixth compound, a seventh compound and an eighth compound as a host, respectively. The sixth compound in the first EML 442, the seventh compound in the second EML 444 and the eighth compound in the third EML 446 may be same or different. For example, each of the host of the first EML 442, i.e., the sixth compound, the host of the second EML 444, i.e., the seventh compound, and the host of the third EML 446, i.e., the eighth compound, may be the above third compound.

In the OLED D3, since the triplet exciton energy of the second compound in the first EML 442 is converted into the singlet exciton energy of the second compound by the RISC, and the singlet exciton energy of the second compound is transferred into the singlet exciton energy of the first compound in the second EML 444 and into the singlet exciton energy of the first compound in the third EML 446. As a result, the first compound in the second and third EMLs 444 and 446 provides the light emission. Accordingly, both the singlet exciton energy and the triplet exciton energy are involved in the light emission such that the emitting efficiency is improved. In addition, since the emission is provided from the first compound being the fluorescent material, the light emission having narrow FWHM is provided.

As described above, the absorption spectrum of the first compound and the emission spectrum of the second compound have an overlap ration being equal to or greater than about 35%.

Accordingly, the energy of the second compound in the first EML 442 is efficiently transferred into the first compound in each of the second and third EMLs 444 and 446 such that the emitting efficiency of the OLED D3 is further improved.

In the first EML 442, the weight ratio of the sixth compound may be equal to or greater than that of the second compound. In the second EML 444, the weight ratio of the seventh compound may be greater than that of the first compound. In the third EML 446, the weight ratio of the eighth compound may be greater than that of the first compound.

In addition, a weight ratio of the second compound in the first EML 442 may be greater than each of that of the first compound in the second EML 444 and that of the first compound in the third EML 446. As a result, the energy is sufficiently and/or efficiently transferred from the second compound in the first EML 442 into the first compound in the second EML 444 and the first compound in the third EML 446 by the FRET. For example, the second compound may have a weight % of about 30 to 50 in the first EML 442, preferably about 40 to 50. The first compound may have a weight % of about 0.01 to 10 in each of the second EML 444 and the third EML 446, preferably about 0.1 to 5. But, it is not limited thereto.

The host of the second EML 444 may be same as a material of the EBL 465. In this instance, the second EML 444 may have an electron blocking function with an emission function. Namely, the second EML 444 may serve as a buffer layer for blocking the electron. When the EBL 465 is omitted, the second EML 444 may serve as an emitting layer and an electron blocking layer.

The host of the third EML 446 may be same as a material of the HBL 475. In this instance, the third EML 446 may have a hole blocking function with an emission function. Namely, the third EML 446 may serve as a buffer layer for blocking the hole. When the HBL 475 is omitted, the third EML 446 may serve as an emitting layer and a hole blocking layer.

The host in the second EML 444 may be same as a material of the EBL 465, and the host in the third EML 446 may be same as a material of the HBL 475. In this instance, the second EML 444 may have an electron blocking function with an emission function, and the third EML 446 may have a hole blocking function with an emission function. Namely, the second EML 444 may serve as a buffer layer for blocking the electron, and the third EML 446 may serve as a buffer layer for blocking the hole. When the EBL 465 and the HBL 475 are omitted, the second EML 444 may serve as an emitting material layer and an electron blocking layer and the third EML 446 serves as an emitting material layer and a hole blocking layer.

Figure 8:
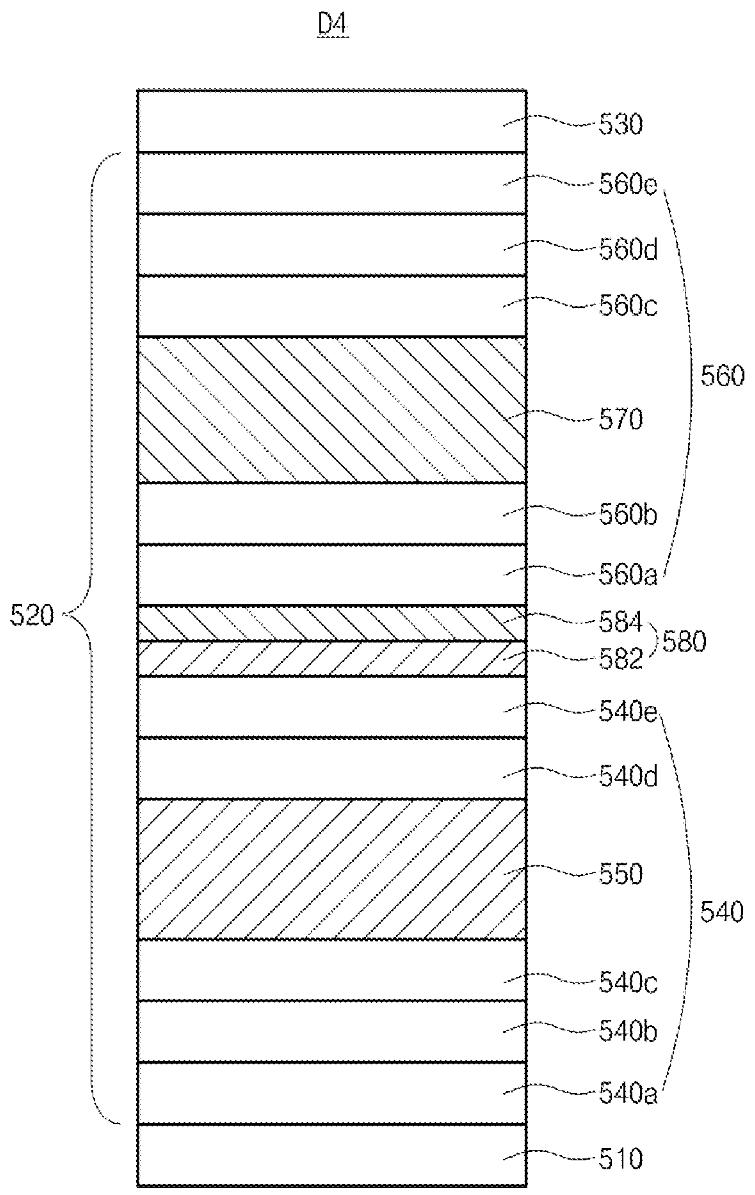
FIG. 8 is a schematic cross-sectional view of an OLED according to a fifth embodiment of the present disclosure.

FIG. 8 is a schematic cross-sectional view of an OLED according to a fifth embodiment of the present disclosure.

As shown in FIG. 8, the OLED D4 includes the first and second electrodes 510 and 530, which face each other, and the light emitting layer 520 therebetween. The organic light emitting display device 100 (of FIG. 2) may include a red pixel region, a green pixel region and a blue pixel region, and the OLED D4 may be positioned in the green pixel region.

The first electrode 510 may be an anode, and the second electrode 530 may be a cathode.

The light emitting layer 520 includes a first emitting part 540 including a first EML 550 and a second emitting part 560 including a second EML 570. In addition, the light emitting layer 520 may further include a charge generation layer (CGL) 580 between the first and second emitting parts 540 and 560.

The CGL 580 is positioned between the first and second emitting parts 540 and 560 such that the first emitting part 540, the CGL 580 and the second emitting part 560 are sequentially stacked on the first electrode 510. Namely, the first emitting part 540 is positioned between the first electrode 510 and the CGL 580, and the second emitting part 580 is positioned between the second electrode 530 and the CGL 580.

The first emitting part 540 includes the first EML 550.

In addition, the first emitting part 540 may further include at least one of a first HTL 540*b* between the first electrode 510 and the first EML 550, an HIL 540*a* between the first electrode 510 and the first HTL 540*b*, and a first ETL 540*e* between the first EML 550 and the CGL 580.

Moreover, the first emitting part 540 may further include at least one of a first EBL 540*c* between the first HTL 540*b* and the first EML 550 and a first HBL 540*d* between the first EML 550 and the first ETL 540*e*.

The second emitting part 560 includes the second EML 570.

In addition, the second emitting part 560 may further include at least one of a second HTL 560*a* between the CGL 580 and the second EML 570, a second ETL 560*d* between the second EML 570 and the second electrode 164, and an EIL 560*e* between the second ETL 560*d* and the second electrode 530.

Moreover, the second emitting part 560 may further include at least one of a second EBL 560*b* between the second HTL 560*a* and the second EML 570 and a second HBL 560*c* between the second EML 570 and the second ETL 560*d*.

The CGL 580 is positioned between the first and second emitting parts 540 and 560. Namely, the first and second emitting parts 540 and 560 are connected to each other through the CGL 580. The CGL 580 may be a P-N junction type CGL of an N-type CGL 582 and a P-type CGL 584.

The N-type CGL 582 is positioned between the first ETL 540*e* and the second HTL 560*a*, and the P-type CGL 584 is positioned between the N-type CGL 582 and the second HTL 560*a*. The N-type CGL 582 provides an electron into the first EML 550 of the first emitting part 540, and the P-type CGL 584 provides a hole into the second EML 570 of the second emitting part 560.

Each of the first and second EMLs 550 and 570 is the green EML. At least one of the first and second EMLs 550 and 570 includes the first compound being the fluorescent material in Formulas 1 and 3 and the second compound being the delayed fluorescent material in Formulas 2 and 4. The first EML 550 may further include the third compound as a host. The third compound may be selected from the compounds in Formula 5.

In the first EML 550, the weight ratio of the second compound may be greater than that of the first compound and may be equal to or smaller than that of the third compound. When the weight ratio of the second compound is greater than that of the first compound, the energy transfer from the second compound into the first compound is sufficiently generated. For example, in the first EML 550, the first compound may have a weight % of 0.01 to 10, preferably 0.1 to 5, the second compound may have a weight % of 30 to 49.9, preferably 40 to 49.9, and the third compound may have a weight % of 40 to 60. However, it is not limited thereto.

The second EML 570 may include the first compound of Formula 1 and the second compound of Formula 2. Alternatively, the second EML 570 may include a compound being different from at least one of the first compound and the second compound in the first EML 550 such that the first and second EMLs 550 and 570 have a different in an emitted-light wavelength or an emitting efficiency.

In the OLED D4 of the present disclosure, the singlet energy level of the second compound as the delayed fluorescent material is transferred into the first compound as the fluorescent dopant, and the light emission is generated from the first compound. Accordingly, the emitting efficiency and the color purity of the OLED D4 are improved. In addition, since the first compound of Formula 1 and the second compound of Formula 2 are included in the first EML 550, the emitting efficiency and the color purity of the OLED D4 are further improved. Moreover, since the OLED D4 has a two-stack structure (double-stack structure) with two green EMLs, the color sense of the OLED D4 is improved and/or the emitting efficiency of the OLED D4 is optimized.

Figure 9:
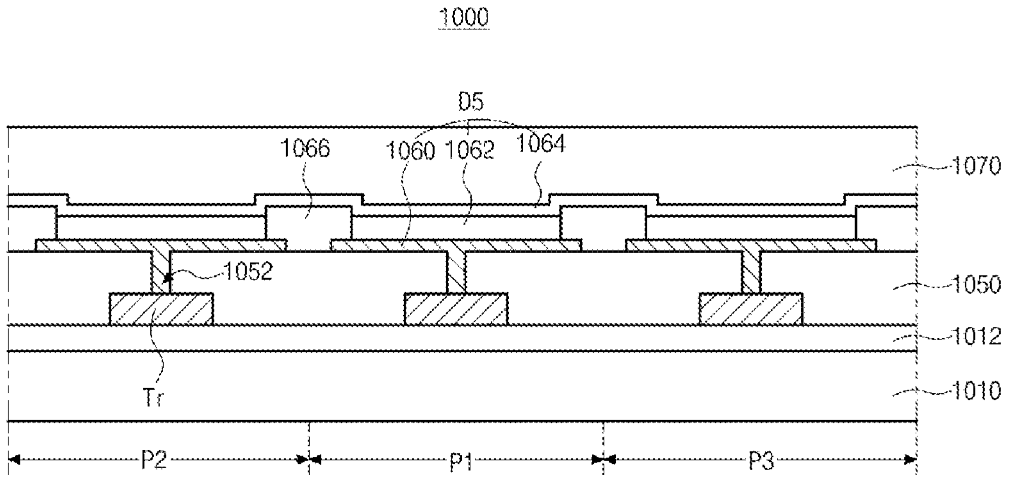
FIG. 9 is a schematic cross-sectional view of an organic light emitting display device according to a sixth embodiment of the present disclosure.

FIG. 9 is a schematic cross-sectional view of an organic light emitting display device according to a sixth embodiment of the present disclosure.

As shown in FIG. 9, the organic light emitting display device 1000 includes a substrate 1010, wherein first to third pixel regions P1, P2 and P3 are defined, a TFT Tr over the substrate 1010 and an OLED D5. The OLED D5 is disposed over the TFT Tr and is connected to the TFT Tr. For example, the first to third pixel regions P1, P2 and P3 may be a green pixel region, a red pixel region and a blue pixel region, respectively.

The substrate 1010 may be a glass substrate or a flexible substrate. For example, the flexible substrate may be a polyimide (PI) substrate, a polyethersulfone (PES) substrate, a polyethylenenaphthalate (PEN) substrate, a polyethylene terephthalate (PET) substrate or a polycarbonate (PC) substrate.

A buffer layer 1012 is formed on the substrate 1010, and the TFT Tr is formed on the buffer layer 1012. The buffer layer 1012 may be omitted.

As explained with FIG. 2, the TFT Tr may include a semiconductor layer, a gate electrode, a source electrode and a drain electrode and may serve as a driving element.

A planarization layer (or passivation layer) 1050 is formed on the TFT Tr. The planarization layer 1050 has a flat top surface and includes a drain contact hole 1052 exposing the drain electrode of the TFT Tr.

The OLED D5 is disposed on the planarization layer 1050 and includes a first electrode 1060, an emitting layer 1062 and a second electrode 1064. The first electrode 1060 is connected to the drain electrode of the TFT Tr, and the light emitting layer 1062 and the second electrode 1064 are sequentially stacked on the first electrode 1060. The OLED D5 is disposed in each of the first to third pixel regions P1 to P3 and emits different color light in the first to third pixel regions P1 to P3. For example, the OLED D5 in the first pixel region PI may emit the green light, the OLED D5 in the second pixel region P2 may emit the red light, and the OLED D5 in the third pixel region P3 may emit the blue light.

The first electrode 1060 is formed to be separate in the first to third pixel regions P1 to P3, and the second electrode 1064 is formed as one-body to cover the first to third pixel regions P1 to P3.

The first electrode 1060 is one of an anode and a cathode, and the second electrode 1064 is the other one of the anode and the cathode. In addition, one of the first and second electrodes 1060 and 1064 may be a light transmitting electrode (or a semi-transmitting electrode), and the other one of the first and second electrodes 1060 and 1064 may be a reflecting electrode.

For example, the first electrode 1060 may be the anode and may include a transparent conductive oxide material layer formed of a transparent conductive oxide (TCO) material having a relatively high work function. The second electrode 1064 may be the cathode and may include a metallic material layer formed of a low resistance metallic material having a relatively low work function. For example, the transparent conductive oxide material layer of the first electrode 1060 include at least one of indium-tin-oxide (ITO), indium-zinc-oxide (IZO), indium-tin-zinc oxide (ITZO), tin oxide (SnO), zinc oxide (ZnO), indium-copper-oxide (ICO) and aluminum-zinc oxide alloy (Al:ZnO), and the second electrode 1064 may include Al, Mg, Ca, Ag, their alloy, e.g., Mg—Ag alloy, or their combination.

In the bottom-emission type organic light emitting display device 1000, the first electrode 1060 may have a single-layered structure of the transparent conductive oxide material layer.

On the other hand, in the top-emission type organic light emitting display device 1000, a reflection electrode or a reflection layer may be formed under the first electrode 1060. For example, the reflection electrode or the reflection layer may be formed of Ag or aluminum-palladium-copper (APC) alloy. In this instance, the first electrode 1060 may have a triple-layered structure of ITO/Ag/ITO or ITO/APC/ITO. In addition, the second electrode 1064 may have a thin profile (small thickness) to provide a light transmittance property (or a semi-transmittance property).

A bank layer 1066 is formed on the planarization layer 1050 to cover an edge of the first electrode 1060. Namely, the bank layer 1066 is positioned at a boundary of the first to third pixel regions P1 to P3 and exposes a center of the first electrode 1060 in the first to third pixel regions P1 to P3.

The light emitting layer 1062 as an emitting unit is formed on the first electrode 1060. The light emitting layer 1062 may have a single-layered structure of an EML. Alternatively, the light emitting layer 1062 may further include at least one of an HIL, an HTL, an EBL, which are sequentially stacked between the first electrode 1060 and the EML, an HBL, an ETL and an EIL, which are sequentially stacked between the EML and the second electrode 1064.

In the first pixel region P1 being the green pixel region, the EML of the light emitting layer 1062 includes the first compound being the fluorescent material and the second compound being the delayed fluorescent material. The EML of the light emitting layer 1062 may further include the third compound as the host. The first compound is represented by Formula 1, and the second compound is represented by Formula 2.

An encapsulation film 1070 is formed on the second electrode 1064 to prevent penetration of moisture into the OLED D5. The encapsulation film 1070 may have a triple-layered structure including a first inorganic insulating layer, an organic insulating layer and a second inorganic insulating layer, but it is not limited thereto.

The organic light emitting display device 1000 may further include a polarization plate (not shown) for reducing an ambient light reflection. For example, the polarization plate may be a circular polarization plate. In the bottom-emission type organic light emitting display device 1000, the polarization plate may be disposed under the substrate 1010. In the top-emission type organic light emitting display device 1000, the polarization plate may be disposed on or over the encapsulation film 1070.

Figure 10:
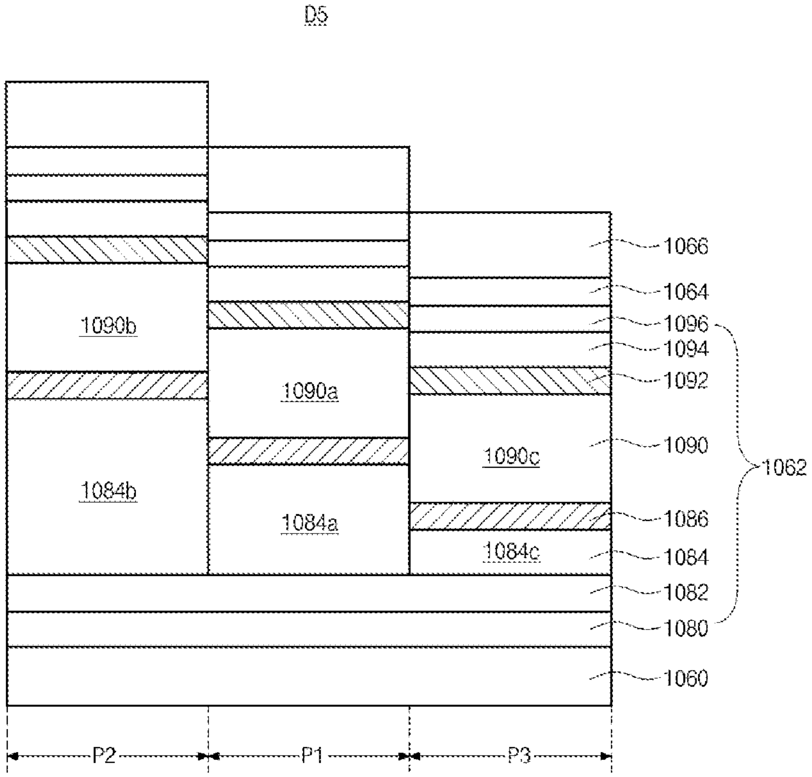
FIG. 10 is a schematic cross-sectional view of an OLED according to a seventh embodiment of the present disclosure.

FIG. 10 is a schematic cross-sectional view of an OLED according to a seventh embodiment of the present disclosure.

Referring to FIG. 10 with FIG. 9, the OLED D5 is positioned in each of first to third pixel regions P1 to P3 and includes the first and second electrodes 1060 and 1064, which face each other, and the light emitting layer 1062 therebetween. The light emitting layer 1062 includes an EML 1090.

The first electrode 1060 may be an anode, and the second electrode 1064 may be a cathode. For example, the first electrode 1060 may be a reflective electrode, and the second electrode 1064 may be a transmitting electrode (or a semi-transmitting electrode).

The light emitting layer 1062 may further include an HTL 1082 between the first electrode 1060 and the EML 1090 and an ETL 1094 between the EML 1090 and the second electrode 1064.

In addition, the light emitting layer 1062 may further include an HIL 1080 between the first electrode 1060 and the HTL 1082 and an EIL 1096 between the ETL 1094 and the second electrode 1064.

Moreover, the light emitting layer 1062 may further include an EBL 1086 between the EML 1090 and the HTL 1082 and an HBL 1092 between the EML 1090 and the ETL 1094.

Furthermore, the light emitting layer 1062 may further include an auxiliary HTL 1084 between the HTL 1082 and the EBL 1086. The auxiliary HTL 1084 may include a first auxiliary HTL 1084*a* in the first pixel region P1, a second auxiliary HTL 1084*b* in the second pixel region P2 and a third auxiliary HTL 1084*c* in the third pixel region P3.

The first auxiliary HTL 1084*a* has a first thickness, the second auxiliary HTL 1084*b* has a second thickness, and the third auxiliary HTL 1084*c* has a third thickness. The first thickness is smaller than the second thickness and greater than the third thickness such that the OLED D5 provides a micro-cavity structure.

Namely, by the first to third auxiliary HTLs 1084*a*, 1084*b* and 1084*c* having a difference in a thickness, a distance between the first and second electrodes 1060 and 1064 in the first pixel region P1, in which a first wavelength range light, e.g., green light, is emitted, is smaller than a distance between the first and second electrodes 1060 and 1064 in the second pixel region P2, in which a second wavelength range light, e.g., red light, being greater than the first wavelength range is emitted, and is greater than a distance between the first and second electrodes 1060 and 1064 in the third pixel region P3, in which a third wavelength range light, e.g., blue light, being smaller than the first wavelength range is emitted. Accordingly, the emitting efficiency of the OLED D5 is improved.

In FIG. 10, the third auxiliary HTL 1084*c* is formed in the third pixel region P3. Alternatively, a micro-cavity structure may be provided without the third auxiliary HTL 1084*c*.

A capping layer (not shown) for improving a light-extracting property may be further formed on the second electrode 1084.

The EML 1090 includes a first EML 1090*a* in the first pixel region P1, a second EML 1090*b* in the second pixel region P2 and a third EML 1090*c* in the third pixel region P3. The first to third EMLs 1090*a*, 1090*b* and 1090*c* may be a green EML, a red EML and a blue EML, respectively.

The first EML 1090*a* in the first pixel region P1 includes the first compound being the fluorescent material and the second compound being the delayed fluorescent material. The first EML 1090*a* in the first pixel region P1 may further include the third compound as the host. The first compound is represented by Formula 1, and the second compound is represented by Formula 2. The third compound may be selected from the compounds in Formula 5.

In the first EML 1090*a* in the first pixel region P1, the weight ratio of the second compound may be greater than that of the first compound and may be equal to or smaller than that of the third compound. When the weight ratio of the second compound is greater than that of the first compound, the energy transfer from the third compound into the first compound is sufficiently generated.

For example, in the first EML 1090*a* in the first pixel region P1, the first compound may have a weight % of 0.01 to 10, preferably 0.1 to 5, the second compound may have a weight % of 30 to 49.9, preferably 40 to 49.9, and the third compound may have a weight % of 40 to 60. However, it is not limited thereto.

Each of the second EML 1090*b* in the second pixel region P2 and the third EML 1090*c* in the third pixel region P3 may include a host and a dopant. For example, in each of the second EML 1090*b* in the second pixel region P2 and the third EML 1090*c* in the third pixel region P3, the dopant may include at least one of a phosphorescent compound, a fluorescent compound and a delayed fluorescent compound.

The OLED D5 in FIG. 10 respectively emits the green light, the red light and the blue light in the first to third pixel regions P1 to P3 such that the organic light emitting display device 1000 (of FIG. 9) can provide a full-color image.

The organic light emitting display device 1000 may further include a color filter layer corresponding to the first to third pixel regions P1 to P3 to improve the color purity. For example, the color filter layer may include a first color filter layer, e.g., a green color filter layer, corresponding to the first pixel region P1, a second color filter layer, e.g., a red color filter layer, corresponding to the second pixel region P2, and a third color filter layer, e.g., a blue color filter layer, corresponding to the third pixel region P3.

In the bottom-emission type organic light emitting display device 1000, the color filter layer may be disposed between the OLED D5 and the substrate 1010. On the other hand, in the top-emission type organic light emitting display device 1000, the color filter layer may be disposed on or over the OLED D5.

Figure 11:
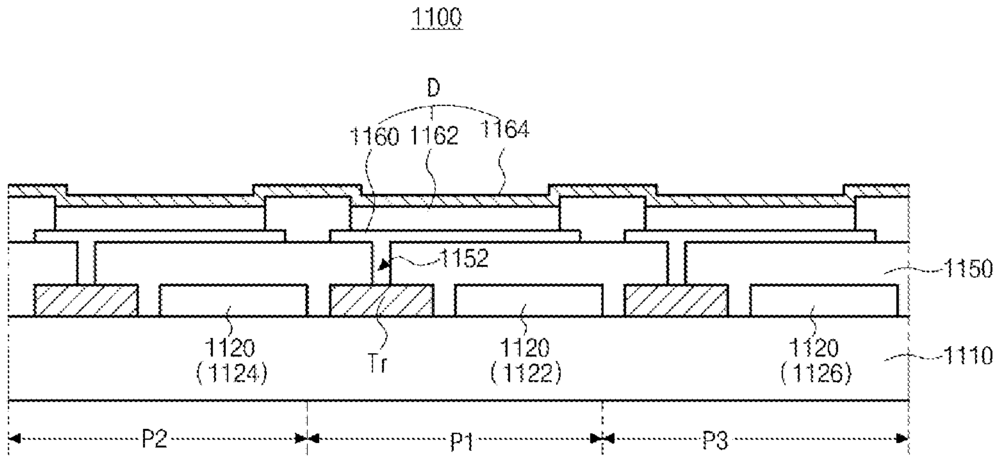
FIG. 11 is a schematic cross-sectional view of an organic light emitting display device according to an eighth embodiment of the present disclosure.

FIG. 11 is a schematic cross-sectional view of an organic light emitting display device according to an eighth embodiment of the present disclosure.

As shown in FIG. 11, the organic light emitting display device 1100 includes a substrate 1110, wherein first to third pixel regions P1, P2 and P3 are defined, a TFT Tr over the substrate 1110, an OLED D, which is disposed over the TFT Tr and is connected to the TFT Tr, and a color filter layer 1120 corresponding to the first to third pixel regions P1 to P3. For example, the first to third pixel regions P1, P2 and P3 may be a green pixel region, a red pixel region and a blue pixel region, respectively.

The substrate 1110 may be a glass substrate or a flexible substrate. For example, the flexible substrate may be a polyimide (PI) substrate, a polyethersulfone (PES) substrate, a polyethylenenaphthalate (PEN) substrate, a polyethylene terephthalate (PET) substrate or a polycarbonate (PC) substrate.

The TFT Tr is formed on the substrate 1110. Alternatively, a buffer layer (not shown) may be formed on the substrate 1110, and the TFT Tr may be formed on the buffer layer.

As explained with FIG. 2, the TFT Tr may include a semiconductor layer, a gate electrode, a source electrode and a drain electrode and may serve as a driving element.

In addition, the color filter layer 1120 is disposed on the substrate 1110. For example, the color filter layer 1120 may include a first color filter layer 1122 corresponding to the first pixel region P1, a second color filter layer 1124 corresponding to the second pixel region P2, and a third color filter layer 1126 corresponding to the third pixel region P3. The first to third color filter layers 1122, 1124 and 1126 may be a green color filter layer, a red color filter layer and a blue color filter layer, respectively. For example, the first color filter layer 1122 may include at least one of a green dye and a green pigment, and the second color filter layer 1124 may include at least one of a red dye and a red pigment. The third color filter layer 1126 may include at least one of a blue dye and a blue pigment.

A planarization layer (or passivation layer) 1150 is formed on the TFT Tr and the color filter layer 1120. The planarization layer 1150 has a flat top surface and includes a drain contact hole 1152 exposing the drain electrode of the TFT Tr.

The OLED D is disposed on the planarization layer 1150 and corresponds to the color filter layer 1120. The OLED D includes a first electrode 1160, an emitting layer 1162 and a second electrode 1164. The first electrode 1160 is connected to the drain electrode of the TFT Tr, and the light emitting layer 1162 and the second electrode 1164 are sequentially stacked on the first electrode 1160. The OLED D emits the white light in each of the first to third pixel regions P1 to P3.

The first electrode 1160 is formed to be separate in the first to third pixel regions P1 to P3, and the second electrode 1164 is formed as one-body to cover the first to third pixel regions P1 to P3.

The first electrode 1160 is one of an anode and a cathode, and the second electrode 1164 is the other one of the anode and the cathode. In addition, the first electrode 1160 may be a light transmitting electrode (or a semi-transmitting electrode), and the second electrode 1164 may be a reflecting electrode.

For example, the first electrode 1160 may be the anode and may include a transparent conductive oxide material layer formed of a transparent conductive oxide (TCO) material having a relatively high work function. The second electrode 1164 may be the cathode and may include a metallic material layer formed of a low resistance metallic material having a relatively low work function. For example, the transparent conductive oxide material layer of the first electrode 1160 include at least one of indium-tin-oxide (ITO), indium-zinc-oxide (IZO), indium-tin-zinc oxide (ITZO), tin oxide (SnO), zinc oxide (ZnO), indium-copper-oxide (ICO) and aluminum-zinc oxide alloy (Al:ZnO), and the second electrode 1164 may include Al, Mg, Ca, Ag, their alloy, e.g., Mg—Ag alloy, or their combination.

The light emitting layer 1162 as an emitting unit is formed on the first electrode 1160. The light emitting layer 1162 includes at least two emitting parts emitting different color light. Each emitting part may have a single-layered structure of an EML. Alternatively, each emitting part may further include at least one of an HIL, an HTL, an EBL, an HBL, an ETL and an EIL. In addition, the light emitting layer 1162 may further include a charge generation layer (CGL) between the emitting parts.

The EML of one of the emitting parts includes the first compound in Formula 1 and the second compound in Formula 2. Namely, the EML of one of the emitting parts includes the fluorescent material and the delayed fluorescent material. The EML of one of the emitting parts may further include the third compound as the host. The third compound may be selected from the compounds in Formula 5.

A bank layer 1166 is formed on the planarization layer 1150 to cover an edge of the first electrode 1160. Namely, the bank layer 1166 is positioned at a boundary of the first to third pixel regions P1 to P3 and exposes a center of the first electrode 1160 in the first to third pixel regions P1 to P3. As mentioned above, since the OLED D emits the white light in the first to third pixel regions P1 to P3, the light emitting layer 1162 may be formed as a common layer in the first to third pixel regions P1 to P3 without separation in the first to third pixel regions P1 to P3. The bank layer 1166 may be formed to prevent the current leakage at an edge of the first electrode 1160 and may be omitted.

Although not shown, the organic light emitting display device 1100 may further include an encapsulation film is formed on the second electrode 1164 to prevent penetration of moisture into the OLED D. In addition, the organic light emitting display device 1100 may further include a polarization plate under the substrate 1110 for reducing an ambient light reflection.

In the organic light emitting display device 1100 (of FIG. 11), the first electrode 1160 is a transparent electrode (light transmitting electrode), and the second electrode 1164 is a reflecting electrode. In addition, the color filter layer 1120 is positioned between the substrate 1110 and the OLED D. Namely, the organic light emitting display device 11000 is a bottom-emission type.

Alternatively, in the organic light emitting display device 1100, the first electrode 1160 may be a reflecting electrode, and the second electrode 1154 may be a transparent electrode (or a semi-transparent electrode). In this case, the color filter layer 1120 is positioned on or over the OLED D.

In the organic light emitting display device 1100, the OLED D in the first to third pixel regions P1 to P3 emits the white light, and the white light passes through the first to third color filter layers 1122, 1124 and 1126. Accordingly, the green light, the red light and the blue light are displayed in the first to third pixel regions P1 to P3, respectively.

Although not shown, a color conversion layer may be formed between the OLED D and the color filter layer 1120. The color conversion layer may include a green color conversion layer, a red color conversion layer and a blue color conversion layer respectively corresponding to the first to third pixel regions P1 to P3, and the white light from the OLED D can be converted into the green light, the red light and the blue light. The color conversion layer may include a quantum dot. Accordingly, the color purity of the OLED D may be further improved.

The color conversion layer may be included instead of the color filter layer 1120.

Figure 12:
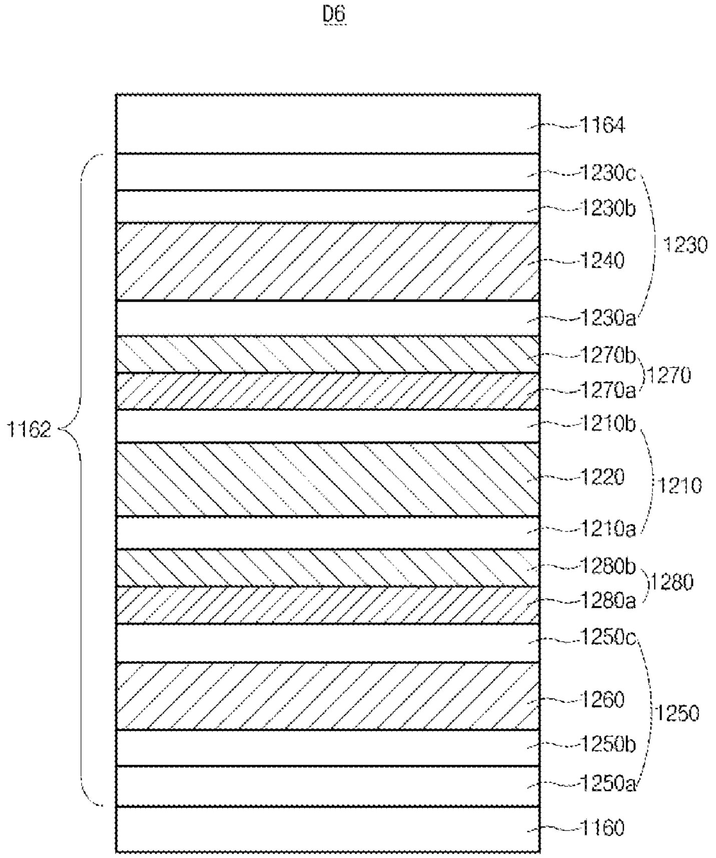
FIG. 12 is a schematic cross-sectional view of an OLED according to a ninth embodiment of the present disclosure.

FIG. 12 is a schematic cross-sectional view of an OLED according to a ninth embodiment of the present disclosure.

As shown in FIG. 12, the OLED D6 includes the first and second electrodes 1160 and 1164, which face each other, and the light emitting layer 1162 therebetween.

The first electrode 1160 may be an anode, and the second electrode 1164 may be a cathode. The first electrode 1160 is a transparent electrode (a light transmitting electrode), and the second electrode 1164 is a reflecting electrode.

The light emitting layer 1162 includes a first emitting part 1210 including a first EML 1220, a second emitting part 1230 including a second EML 1240 and a third emitting part 1250 including a third EML 1260. In addition, the light emitting layer 1162 may further include a first CGL 1270 between the first and second emitting parts 1210 and 1230 and a second CGL 1280 between the first emitting part 1210 and the third emitting part 1250.

The first CGL 1270 is positioned between the first and second emitting parts 1210 and 1230, and the second CGL 1280 is positioned between the first and third emitting parts 1210 and 1250. Namely, the third emitting part 1250, the second CGL 1280, the first emitting part 1210, the first CGL 1270 and the second emitting part 1230 are sequentially stacked on the first electrode 1160. In other words, the first emitting part 1210 is positioned between the first and second CGLs 1270 and 1280, and the second emitting part 1230 is positioned between the first CGL 1270 and the second electrode 1164. The third emitting part 1250 is positioned between the second CGL 1280 and the first electrode 1160.

The first emitting part 1210 may further include a first HTL 1210*a* under the first EML 1220 and a first ETL 1210*b* over the first EML 1220. Namely, the first HTL 1210*a* may positioned between the first EML 1220 and the second CGL 1270, and the first ETL 1210*b* may be positioned between the first EML 1220 and the first CGL 1270.

In addition, the first emitting part 1210 may further include an EBL (not shown) between the first HTL 1210*a* and the first EML 1220 and an HBL (not shown) between the first ETL 1210*b* and the first EML 1220.

The second emitting part 1230 may further include a second HTL 1230*a* under the second EML 1240, a second ETL 1230*b* over the second EML 1240 and an EIL 1230*c* on the second ETL 1230*b*. Namely, the second HTL 1230*a* may be positioned between the second EML 1240 and the first CGL 1270, and the second ETL 1230*b* and the EIL 1230*c* may be positioned between the second EML 1240 and the second electrode 1164.

In addition, the second emitting part 1230 may further include an EBL (not shown) between the second HTL 1230*a* and the second EML 1240 and an HBL (not shown) between the second ETL 1230*b* and the second EML 1240.

The third emitting part 1250 may further include a third HTL 1250*b* under the third EML 1260, an HIL 1250*a* under the third HTL 1250*b* and a third ETL 1250*c* over the third EML 1260. Namely, the HIL 1250*a* and the third HTL 1250*b* may be positioned between the first electrode 1160 and the third EML 1260, and the third ETL 1250*c* may be positioned between the third EML 1260 and the second CGL 1280.

In addition, the third emitting part 1250 may further include an EBL (not shown) between the third HTL 1250*b* and the third EML 1260 and an HBL (not shown) between the third ETL 1250*c* and the third EML 1260.

One of the first to third EMLs 1220, 1240 and 1260 is a green EML. Another one of the first to third EMLs 1220, 1240 and 1260 may be a blue EML, and the other one of the first to third EMLs 1220, 1240 and 1260 may be a red EML.

For example, the first EML 1220 may be the green EML, the second EML 1240 may be the blue EML, and the third EML 1260 may be the red EML. Alternatively, the first EML 1220 may be the green EML, the second EML 1240 may be the red EML, and the third EML 1260 may be the blue EML.

The first EML 1220 includes the first compound being the fluorescent material and the second compound being the delayed fluorescent material. In addition, the first EML 1220 may further include the third compound as the host. The first compound is represented by Formula 1, and the second compound is represented by Formula 2. The third compound may be selected from the compounds in Formula 5.

In the first EML 1220, the weight ratio of the second compound may be greater than that of the first compound and may be equal to or smaller than that of the third compound. When the weight ratio of the second compound is greater than that of the first compound, the energy transfer from the third compound into the first compound is sufficiently generated. For example, in the first EML 1220, the first compound may have a weight % of 0.01 to 10, preferably 0.1 to 5, the second compound may have a weight % of 30 to 49.9, preferably 40 to 49.9, and the third compound may have a weight % of 40 to 60. However, it is not limited thereto.

The second EML 1240 includes a host and a blue dopant (or a red dopant), and the third EML 1260 includes a host and a red dopant (or a blue dopant). For example, in each of the second and third EMLs 1240*a* and 1260, the dopant may include at least one of a phosphorescent compound, a fluorescent compound and a delayed fluorescent compound.

The OLED D6 in the first to third pixel regions P1 to P3 (of FIG. 11) emits the white light, and the white light passes through the color filter layer 1120 (of FIG. 11) in the first to third pixel regions P1 to P3. Accordingly, the organic light emitting display device 1100 (of FIG. 11) can provide a full-color image.

Figure 13:
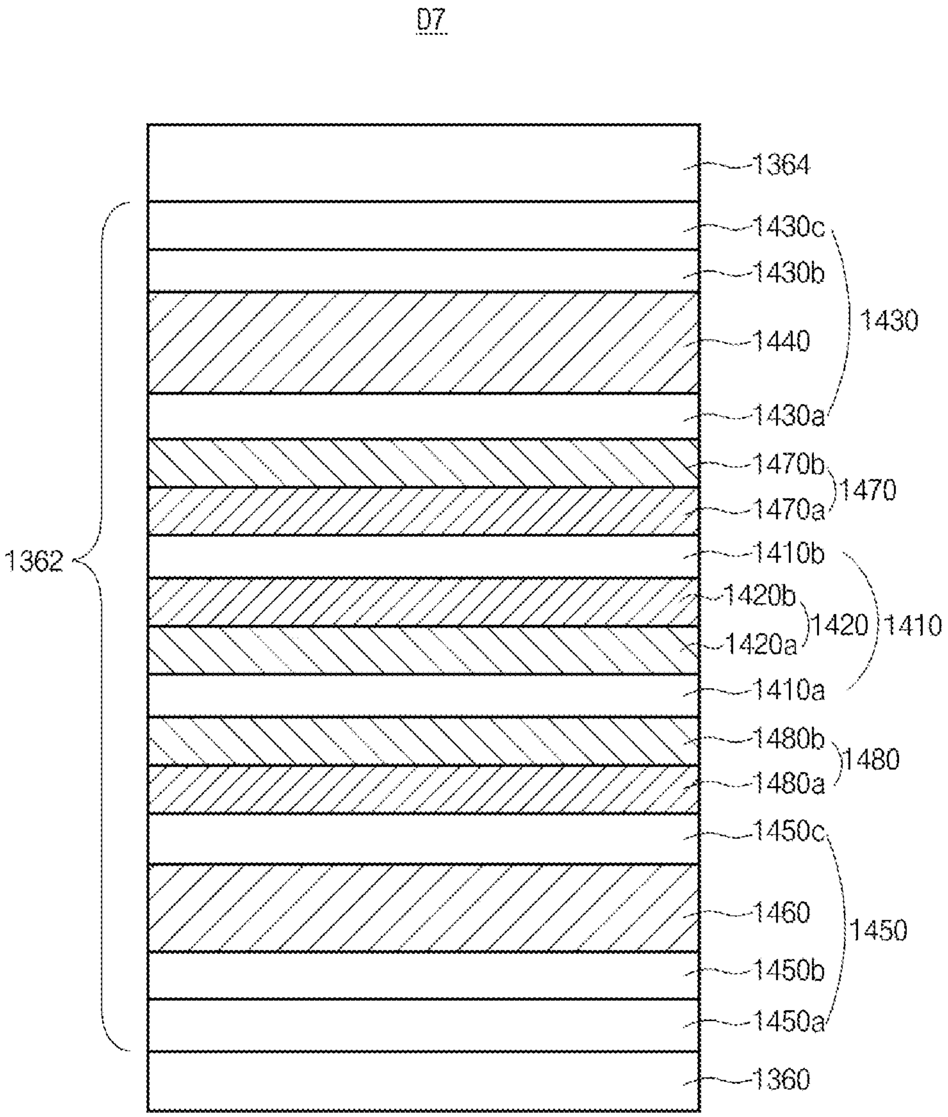
FIG. 13 is a schematic cross-sectional view of an OLED according to a tenth embodiment of the present disclosure.

FIG. 13 is a schematic cross-sectional view of an OLED according to a tenth embodiment of the present disclosure.

As shown in FIG. 13, the OLED D7 includes the first and second electrodes 1360 and 1364, which face each other, and the light emitting layer 1362 therebetween.

The first electrode 1360 may be an anode, and the second electrode 1364 may be a cathode. The first electrode 1360 is a transparent electrode (a light transmitting electrode), and the second electrode 1364 is a reflecting electrode.

The light emitting layer 1362 includes a first emitting part 1410 including a first EML 1420, a second emitting part 1430 including a second EML 1440 and a third emitting part 1450 including a third EML 1460. In addition, the light emitting layer 1362 may further include a first CGL 1470 between the first and second emitting parts 1410 and 1430 and a second CGL 1480 between the first emitting part 1410 and the third emitting part 1450.

The first emitting part 1420 includes a lower EML 1420*a* and an upper EML 1420*b*. Namely, the lower EML 1420*a* is positioned to be closer to the first electrode 1360, and the upper EML 1420*b* is positioned to be closer to the second electrode 1364.

The first CGL 1470 is positioned between the first and second emitting parts 1410 and 1430, and the second CGL 1480 is positioned between the first and third emitting parts 1410 and 1450. Namely, the third emitting part 1450, the second CGL 1480, the first emitting part 1410, the first CGL 1470 and the second emitting part 1430 are sequentially stacked on the first electrode 1360. In other words, the first emitting part 1410 is positioned between the first and second CGLs 1470 and 1480, and the second emitting part 1430 is positioned between the first CGL 1470 and the second electrode 1364. The third emitting part 1450 is positioned between the second CGL 1480 and the first electrode 1360.

The first emitting part 1410 may further include a first HTL 1410*a* under the first EML 1420 and a first ETL 1410*b* over the first EML 1420.

In addition, the first emitting part 1410 may further include an EBL (not shown) between the first HTL 1410*a* and the first EML 1420 and an HBL (not shown) between the first ETL 1410*b* and the first EML 1420.

The second emitting part 1430 may further include a second HTL 1430*a* under the second EML 1440, a second ETL 1430*b* over the second EML 1440 and an EIL 1430*c* on the second ETL 1430*b*. Namely, the second HTL 1430*a* may be positioned between the second EML 1440 and the first CGL 1470, and the second ETL 1430*b* and the EIL 1430*c* may be positioned between the second EML 1440 and the second electrode 1364.

In addition, the second emitting part 1430 may further include an EBL (not shown) between the second HTL 1430*a* and the second EML 1440 and an HBL (not shown) between the second ETL 1430*b* and the second EML 1440.

The third emitting part 1450 may further include a third HTL 1450*b* under the third EML 1460, an HIL 1450*a* under the third HTL 1450*b* and a third ETL 1450*c* over the third EML 1460. Namely, the HIL 1450*a* and the third HTL 1450*b* may be positioned between the first electrode 1360 and the third EML 1460, and the third ETL 1450*c* may be positioned between the third EML 1460 and the second CGL 1480.

In addition, the third emitting part 1450 may further include an EBL (not shown) between the third HTL 1450*b* and the third EML 1460 and an HBL (not shown) between the third ETL 1450*c* and the third EML 1460.

One of the lower and upper EMLs 1420*a* and 1420*b* of the first EML 1420 is a green EML, and the other one of the lower and upper EMLs 1420*a* and 1420*b* of the first EML 1420 may be a red EML. Namely, the green EML (or the red EML) and the red EML (or the green EML) are sequentially stacked to form the first EML 1420.

For example, the upper EML 1420*b* being the green EML includes the first compound being the fluorescent material and the second compound being the delayed fluorescent material. In addition, the upper EML 1420*b* may further include the third compound as the host. The first compound is represented by Formula 1, and the second compound is represented by Formula 2. The third compound may be selected from the compounds in Formula 5.

In the upper EML 1420*b*, the weight ratio of the second compound may be greater than that of the first compound and may be equal to or smaller than that of the third compound. When the weight ratio of the second compound is greater than that of the first compound, the energy transfer from the third compound into the first compound is sufficiently generated. For example, in the upper EML 1420*b*, the first compound may have a weight % of 0.01 to 10, preferably 0.1 to 5, the second compound may have a weight % of 30 to 49.9, preferably 40 to 49.9, and the third compound may have a weight % of 40 to 60. However, it is not limited thereto.

The lower EML 1420*a* being the red EML may include a host and a red dopant.

Each of the second and third EMLs 1440 and 1460 may be a blue EML. Each of the second and third EMLs 1440 and 1460 may include a host and a blue dopant. The host and the dopant of the second EML 1440 may be same as the host and the dopant of the third EML 1460. Alternatively, the host and the dopant of the second EML 1440 may be different from the host and the dopant of the third EML 1460. For example, the dopant in the second EML 1440 may have a difference in the emitting efficiency and/or the emitting light wavelength from the dopant in the third EML 1460.

In each of the lower EML 1420*a*, the second EML 1440 and the third EML 1460, the dopant may include at least one of a phosphorescent compound, a fluorescent compound and a delayed fluorescent compound.

The OLED D7 in the first to third pixel regions P1 to P3 (of FIG. 11) emits the white light, and the white light passes through the color filter layer 1120 (of FIG. 11) in the first to third pixel regions P1 to P3. Accordingly, the organic light emitting display device 1100 (of FIG. 11) can provide a full-color image.

In FIG. 13, the OLED D7 has a three-stack (triple-stack) structure including the second and third EMLs 1440 and 1460 being the blue EML with the first EML 1420. Alternatively, one of the second and third EMLs 1440 and 1460 may be omitted such that the OLED D7 may have a two-stack (double-stack) structure.

As shown in FIGS. 8, 12 and 13, the OLED in each pixel region includes a first EML, e.g., a green EML, including the organic compound of the present disclosure, one or more second EML and a CGL so that the OLED has a tandem structure. In this instance, one or more second EML is at least one of a red EML, a green EML and a blue EML so that the OLED provides the green emission or the white emission.

While the present disclosure has been described with reference to exemplary embodiments and examples, these embodiments and examples are not intended to limit the scope of the present disclosure. Rather, it will be apparent to those skilled in the art that various modifications and variations can be made in the present disclosure without departing from the spirit or scope of the invention. Thus, it is intended that the present disclosure cover the modifications and variations of the present disclosure provided they come within the scope of the appended claims and their equivalents.

The various embodiments described above can be combined to provide further embodiments. All of patents, patent application publications, patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An organic light emitting diode, comprising:

a first electrode;

a second electrode facing the first electrode; and a first emitting material layer including a first compound and a second compound, the first emitting material layer positioned between the first electrode and the second electrode, wherein the first compound is represented by Formula 1:

[Formula 1]

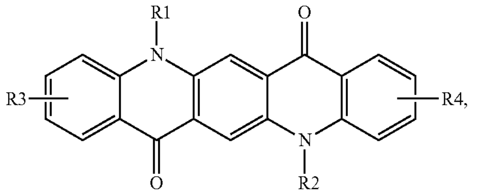

wherein each of R1 and R2 is independently selected from a group consisting of hydrogen, deuterium, C1 to C20 alkyl group, C6 to C30 aryl group, and C3 to C40 heteroaryl group, wherein each of R3 and R4 is independently selected from a group consisting of hydrogen, deuterium, C1 to C20 alkyl group, C6 to C30 aryl group, and C4 to C40 heteroaryl group, or at least one pair of adjacent two of R3 and adjacent two R4 are linked to each other to form a fused ring, wherein the second compound is one of compounds in Formula 4:

[Formula 4]

2-1

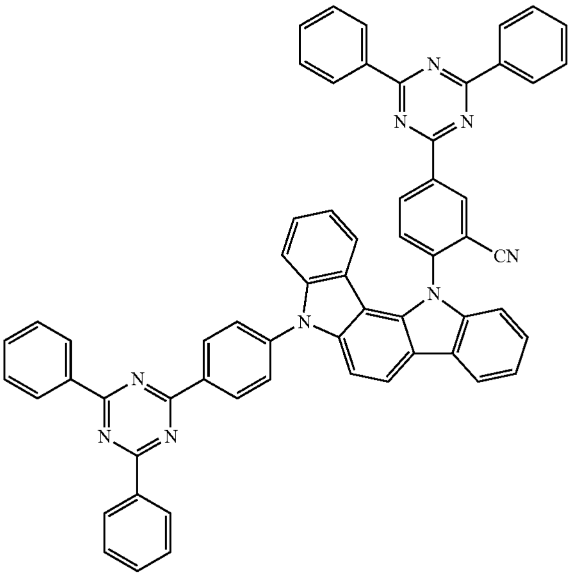

-continued 2-2

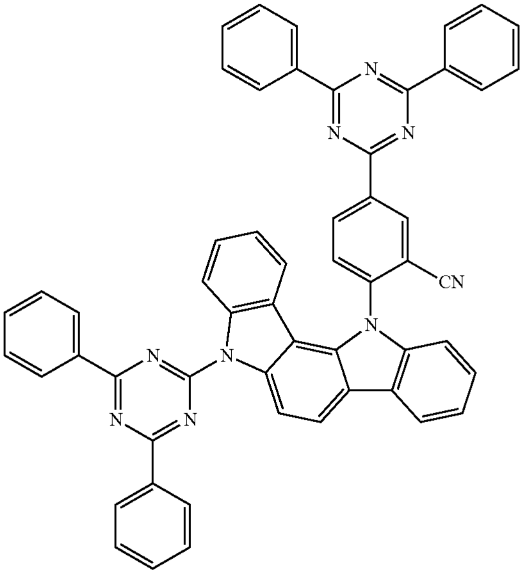

2-3

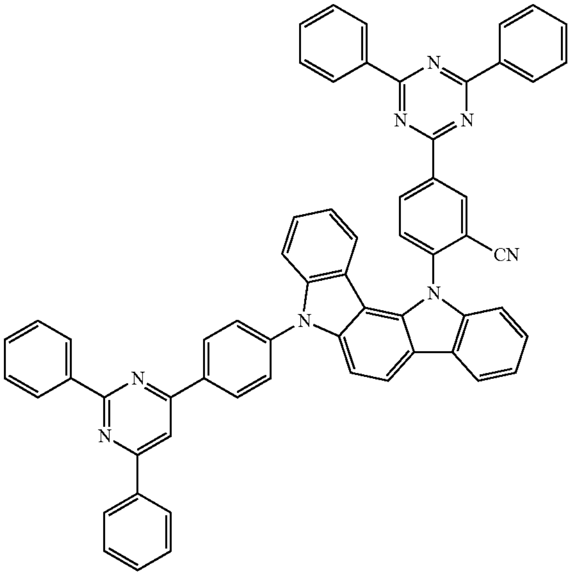

-continued
2-4
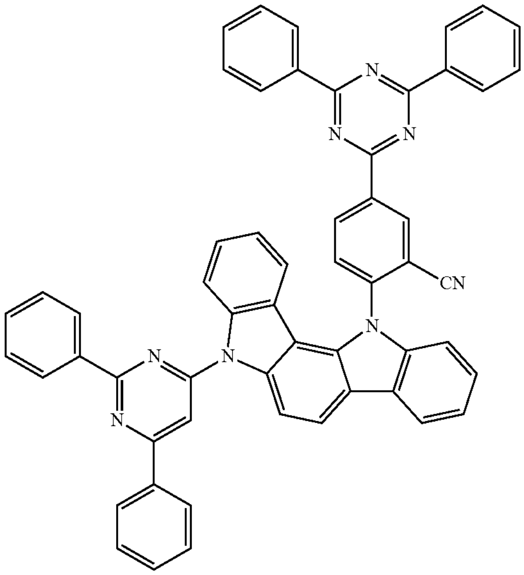
2-5
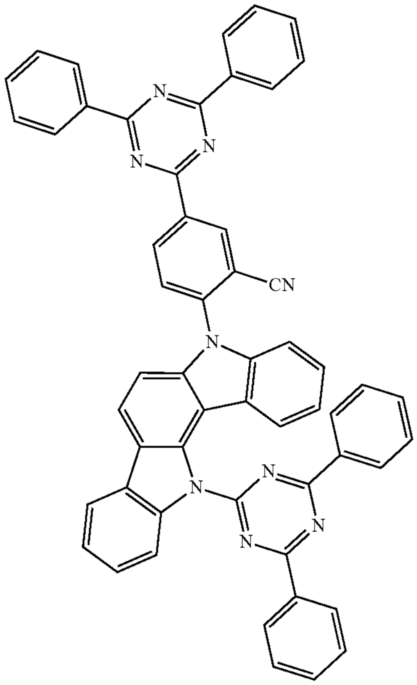
-continued
2-6
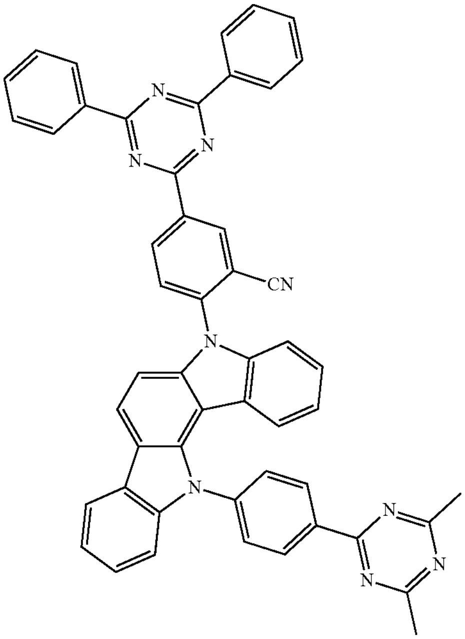
2-7
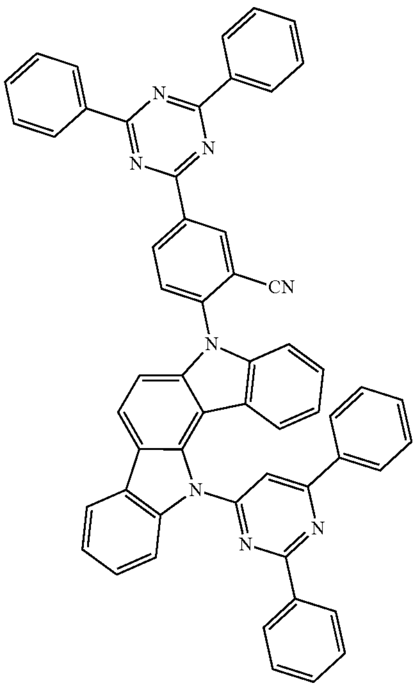

-continued
2-8
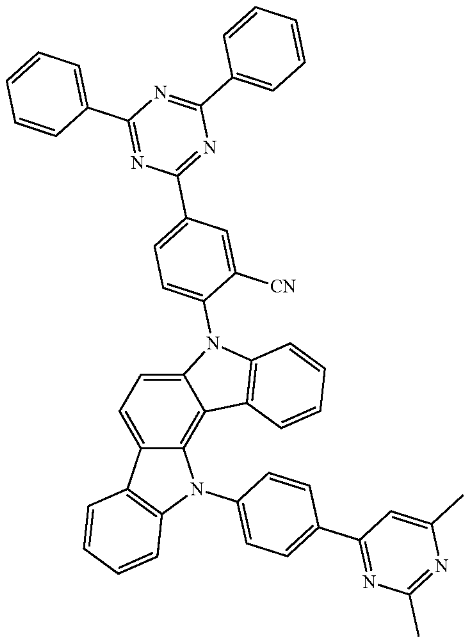
2-9
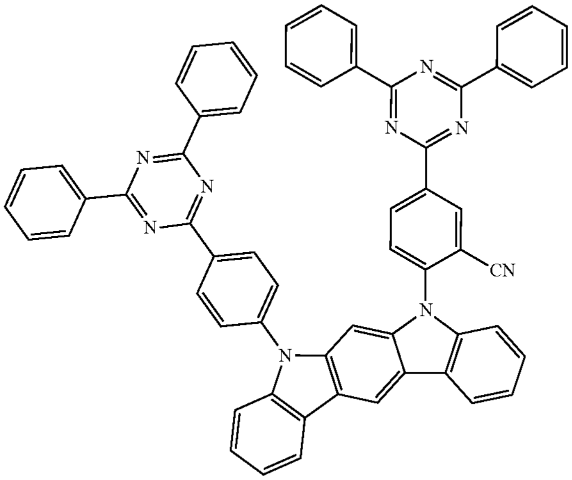
2-10
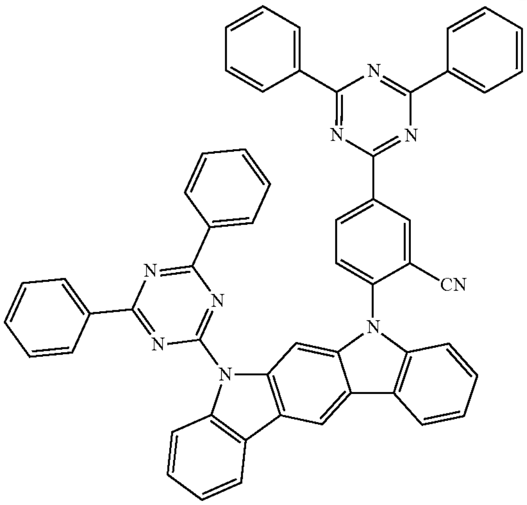
-continued
2-11
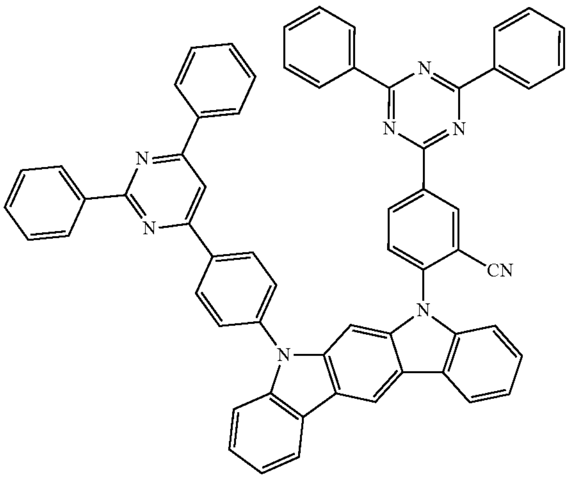
2-12
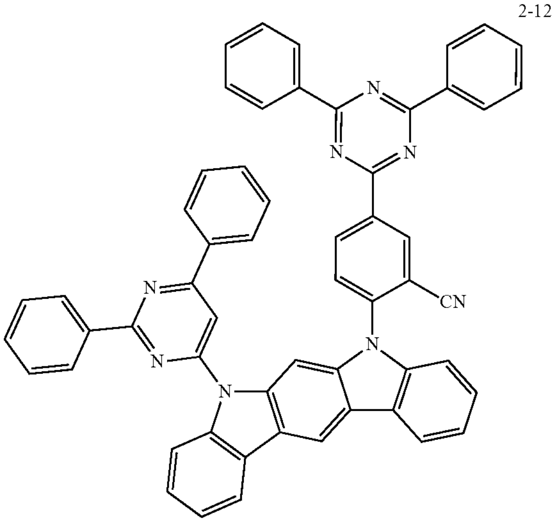
2-13
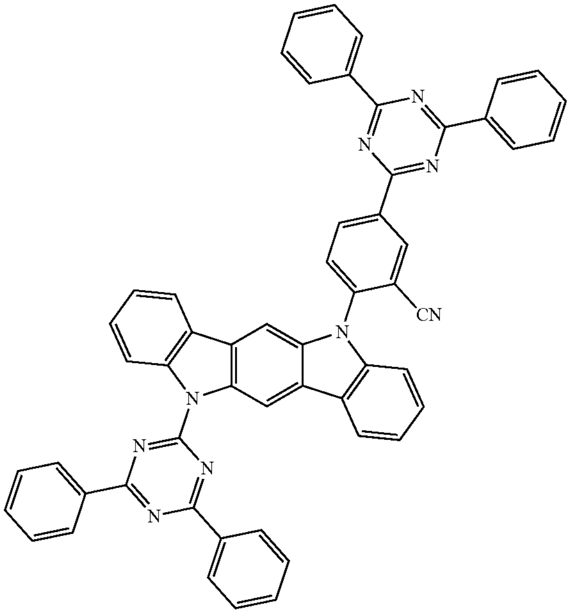

2-14
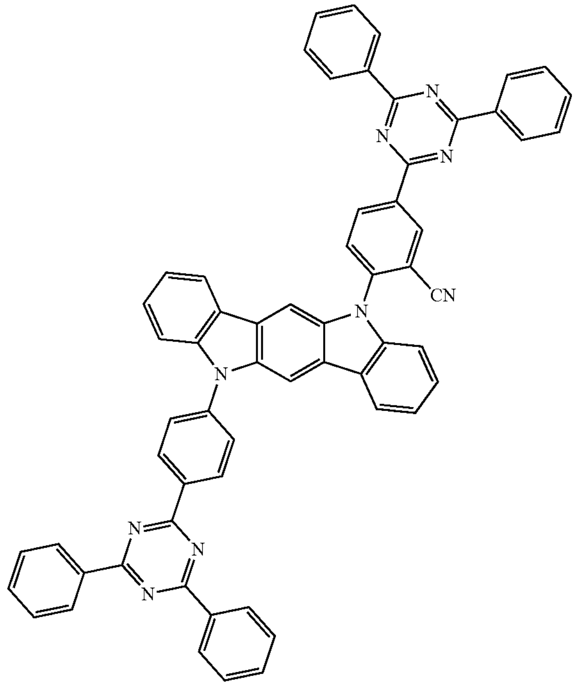
2-15
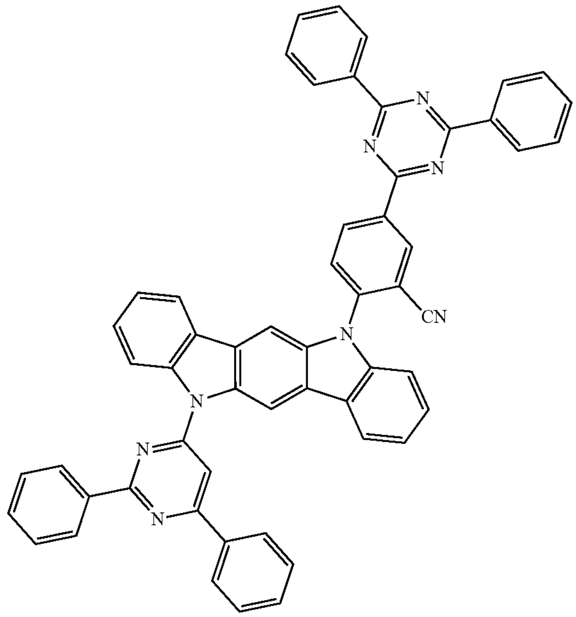
2-16
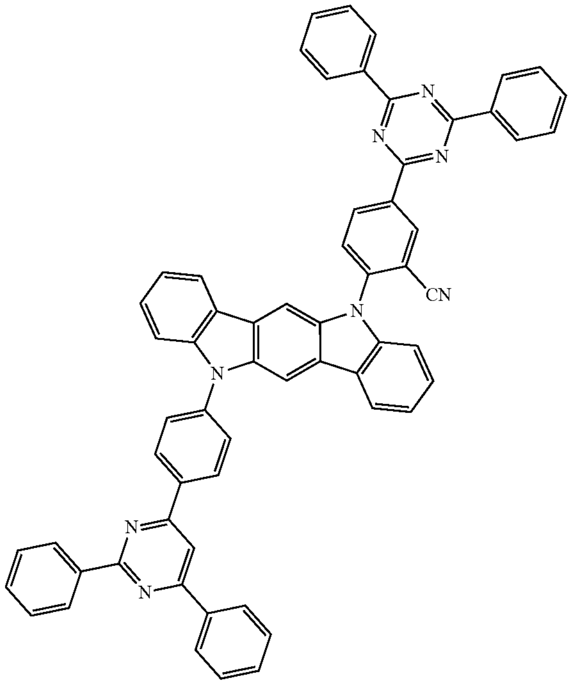
2-17
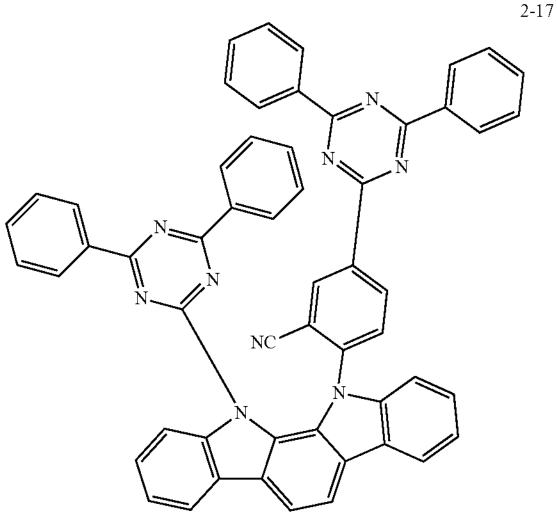

-continued
2-18
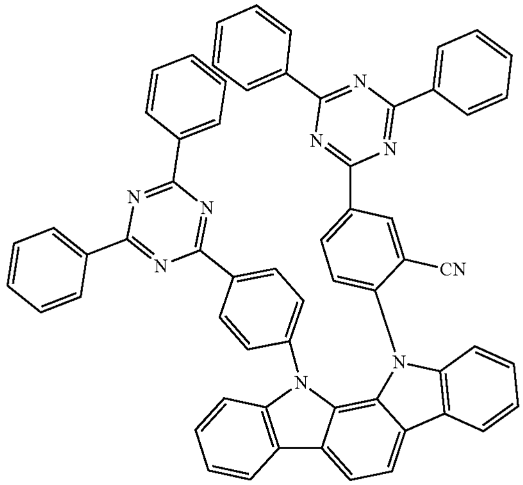
2-19
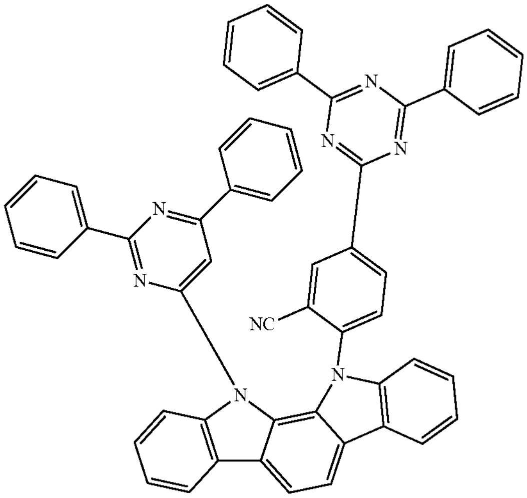
2-20
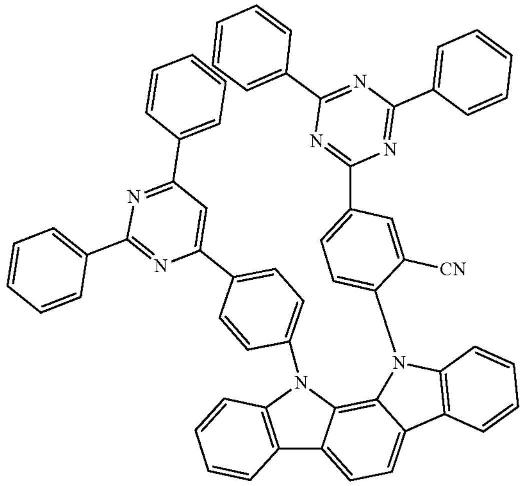
-continued
2-21
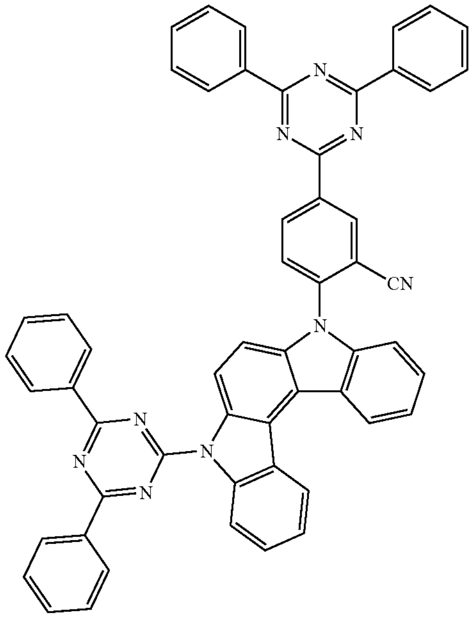
2-22
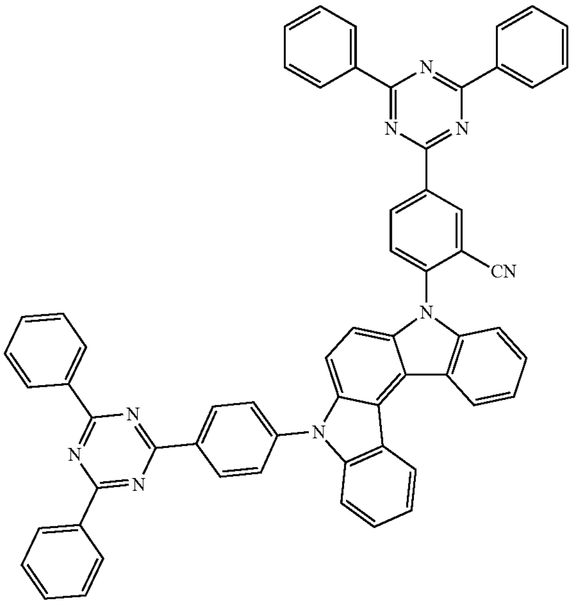

-continued
2-23
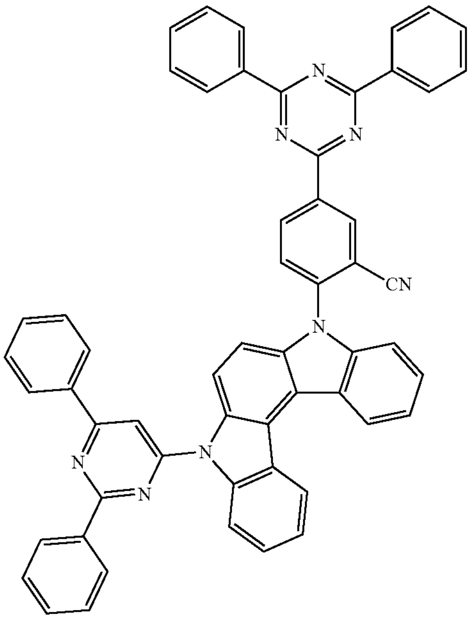
2-24
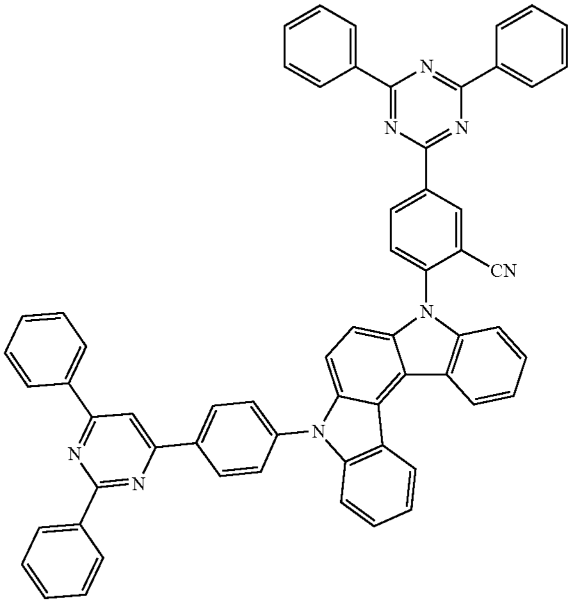
-continued
2-25
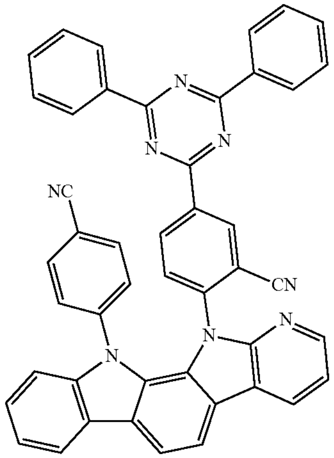
2-26
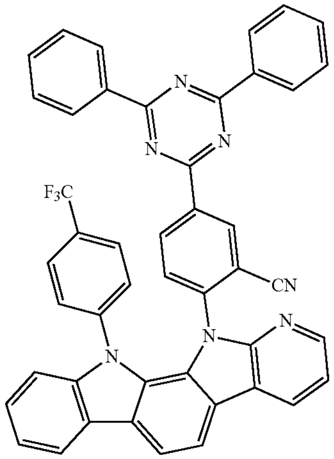
2-27
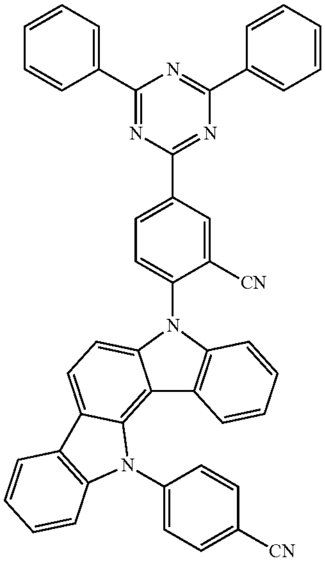

-continued
2-28
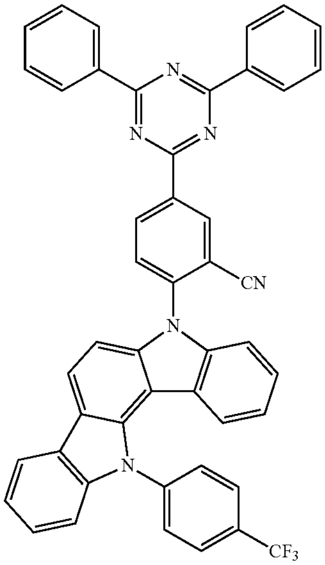
2-30
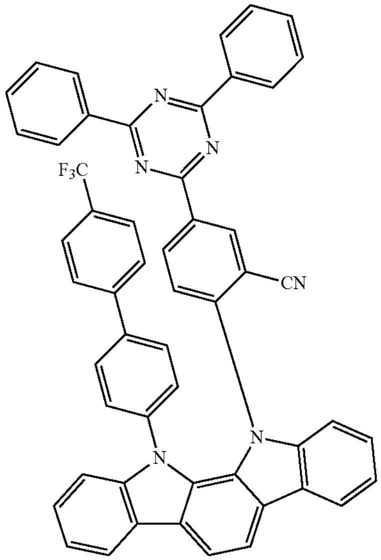
2-29
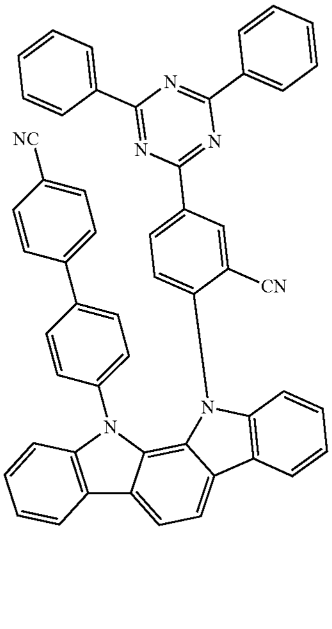
2-31
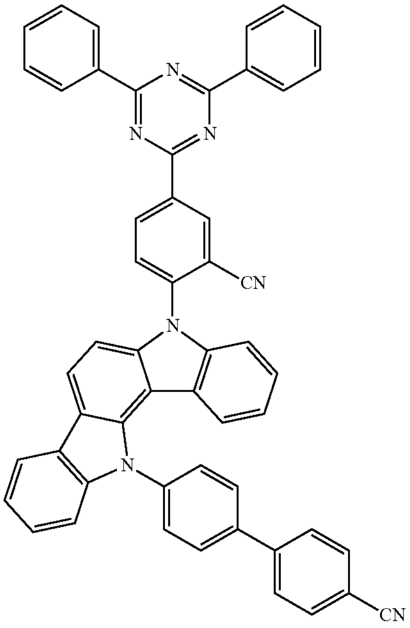

-continued
2-32
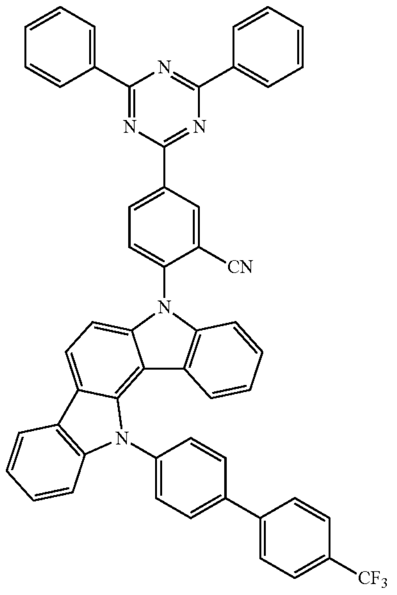
2-33
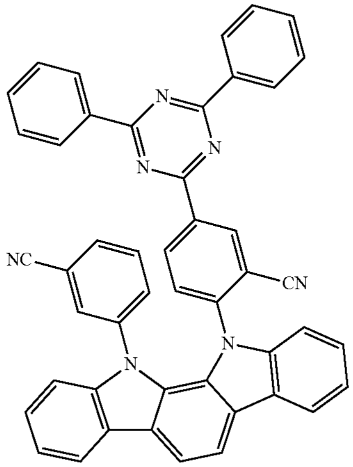
2-34
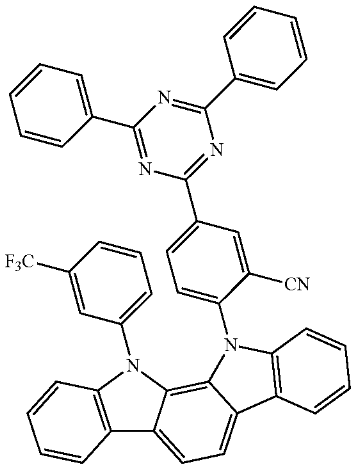
-continued
2-35
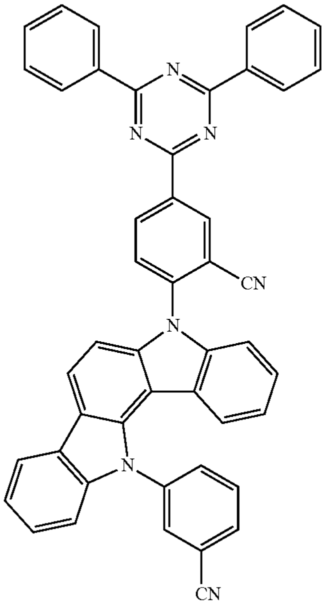
2-36
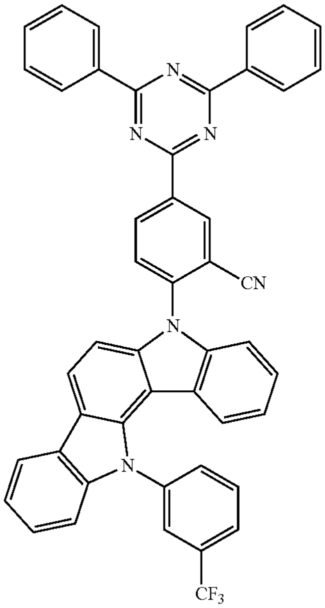

-continued
2-37
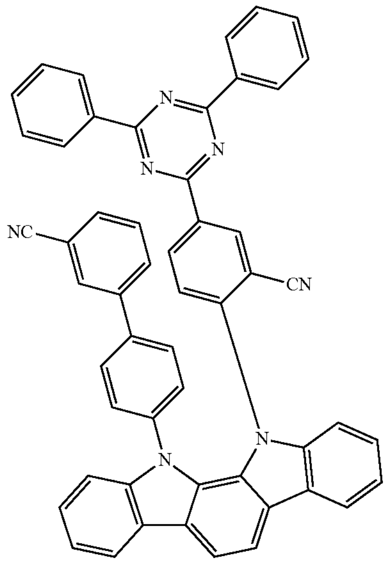
2-38
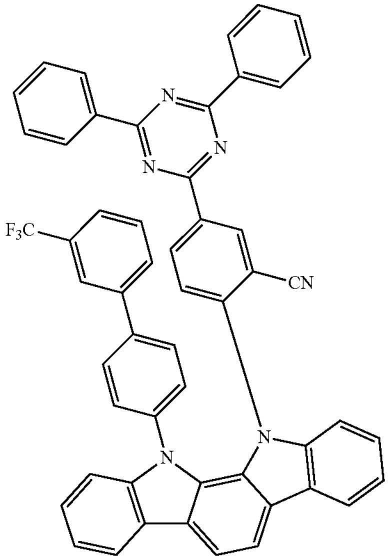
-continued
2-39
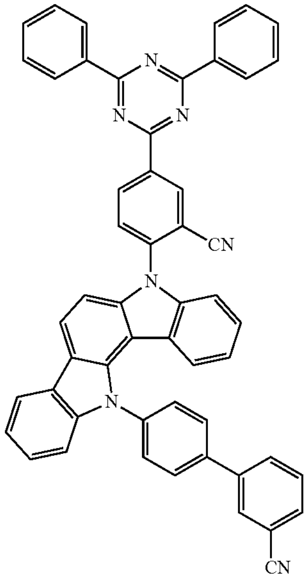
2-40
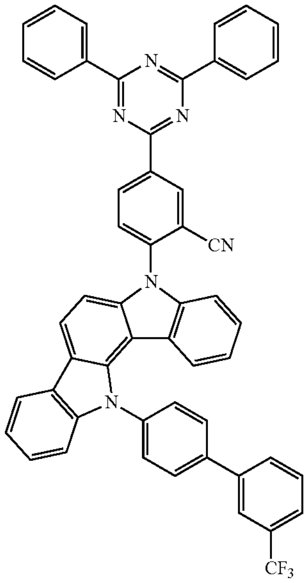
2-41
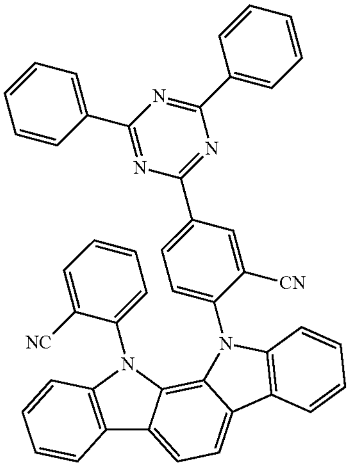

-continued
2-42
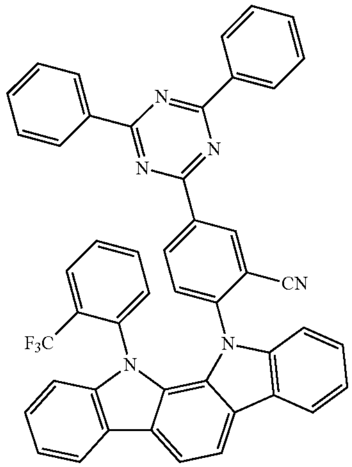
2-43
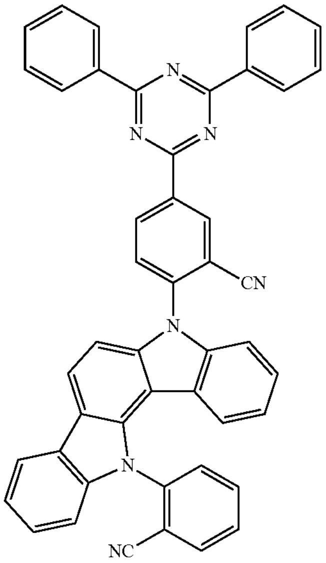
2-44
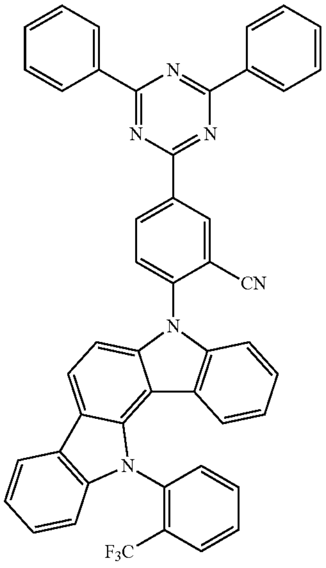
-continued
2-45
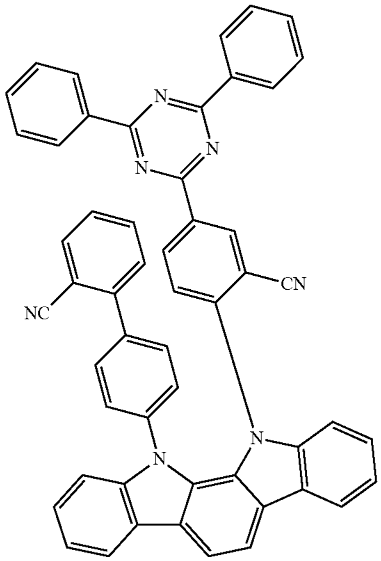
2-46
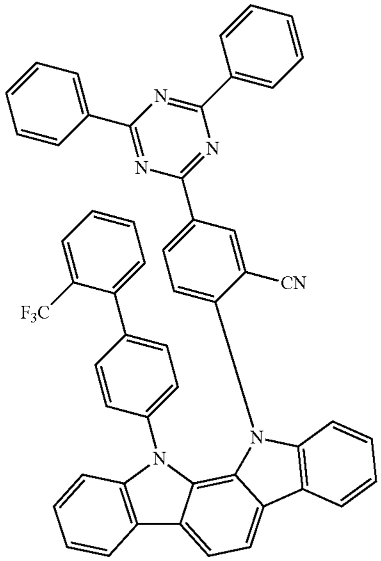

-continued
2-47
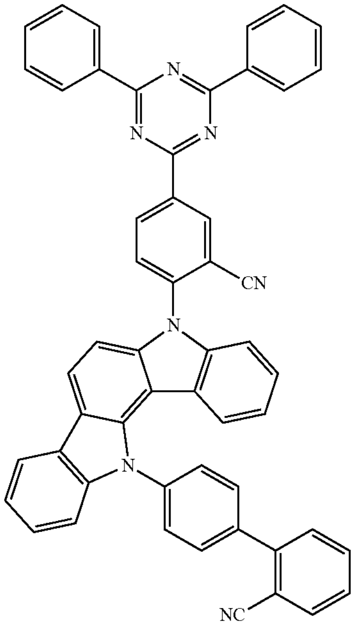
2-48
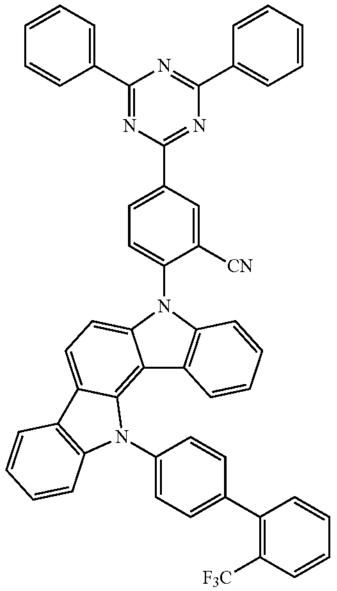
2-49
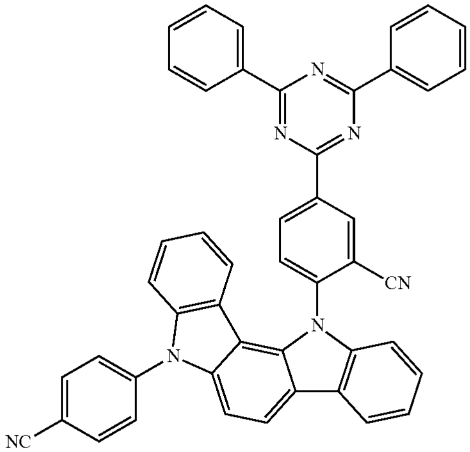
-continued
2-50
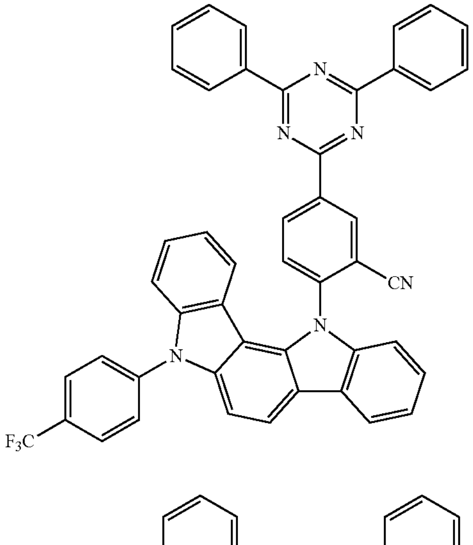
2-51
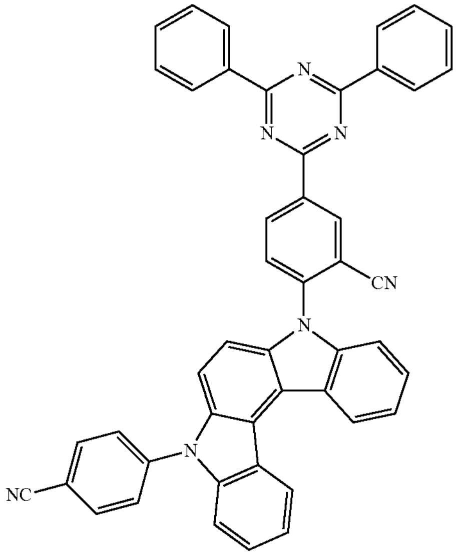
2-52
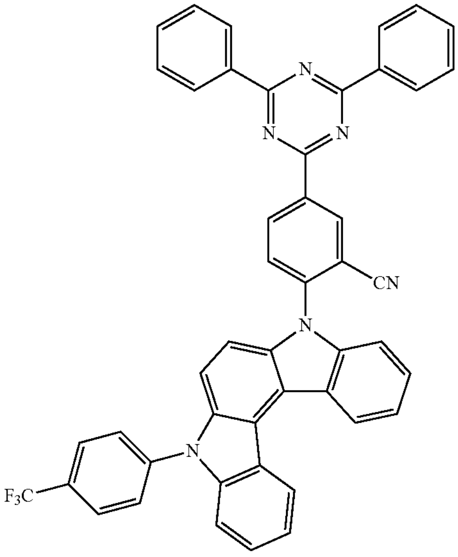

-continued
2-53
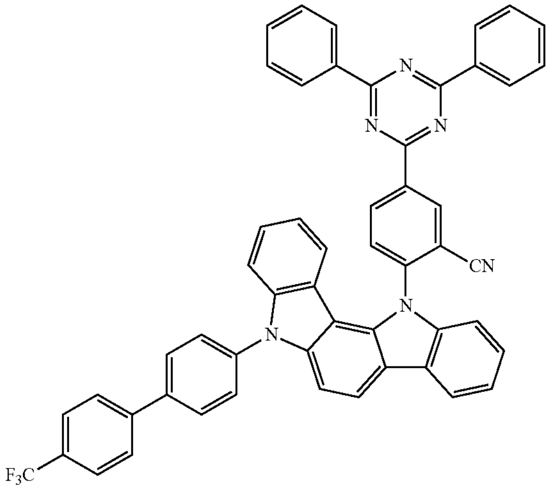
2-54
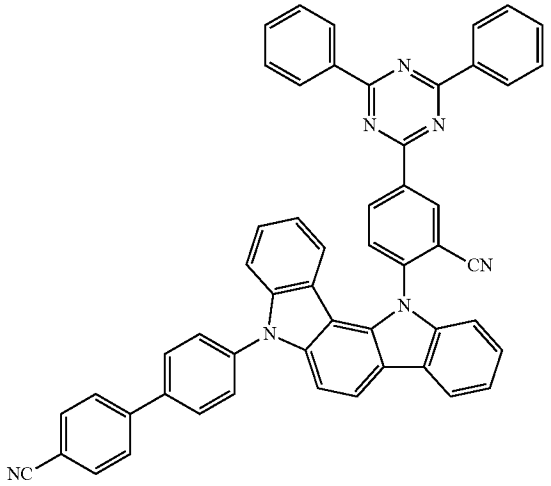
2-55
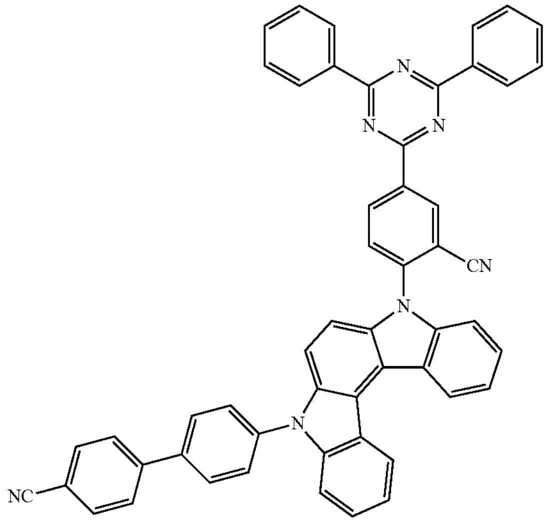
-continued
2-56
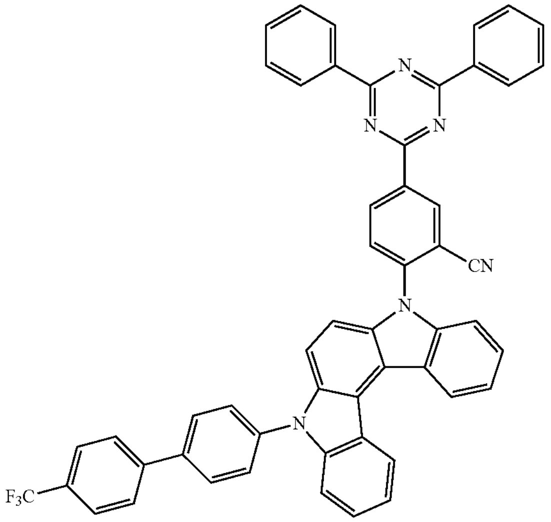
2-57
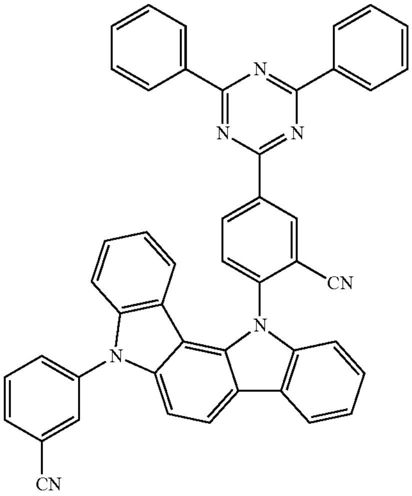
2-58
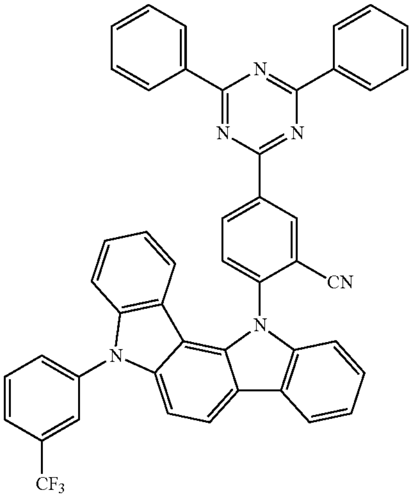

-continued
2-59
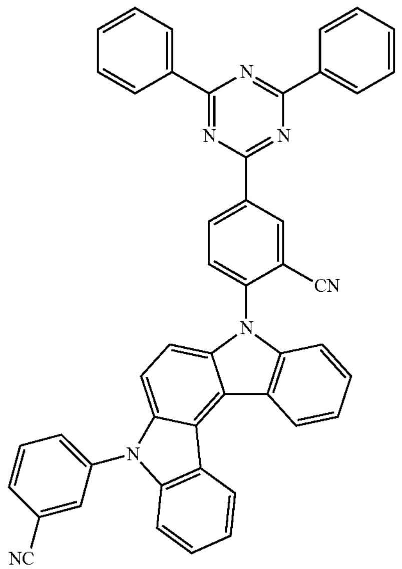
2-60
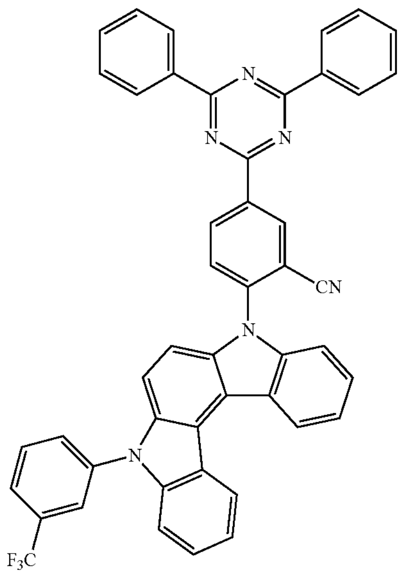
-continued
2-61
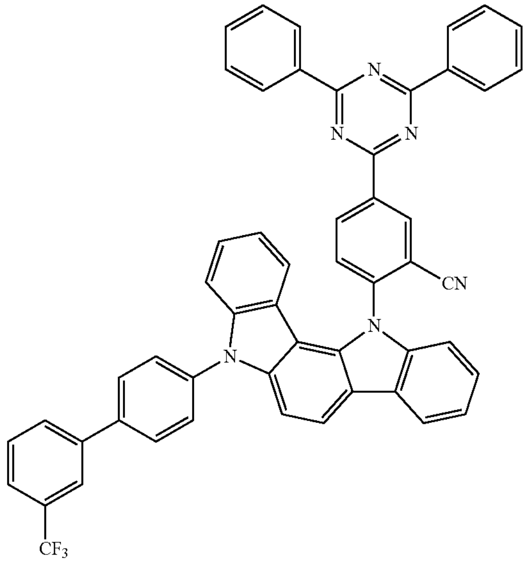
2-62
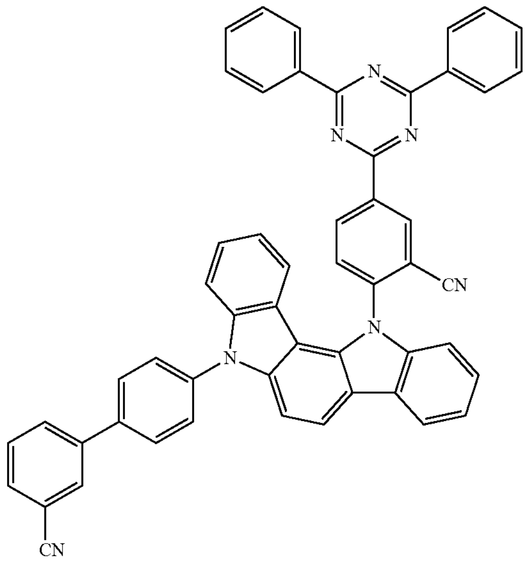

-continued
2-63
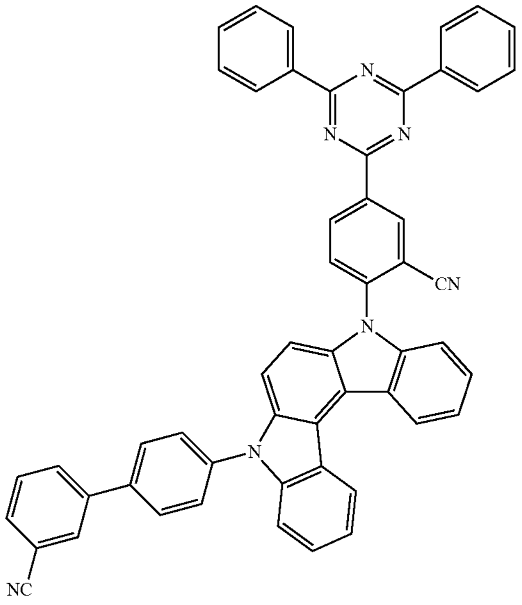
2-64
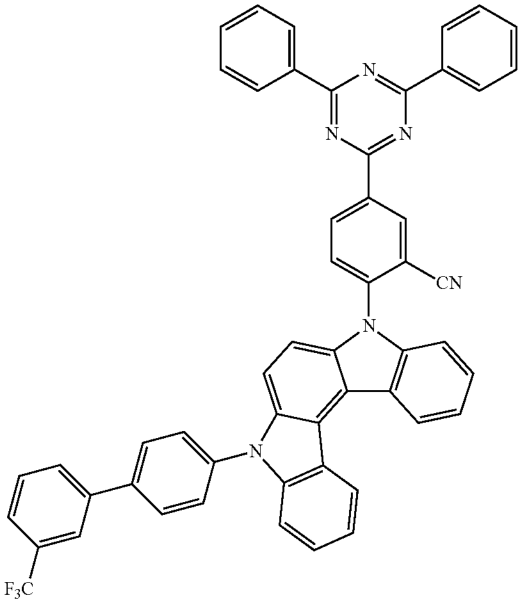
-continued
2-65
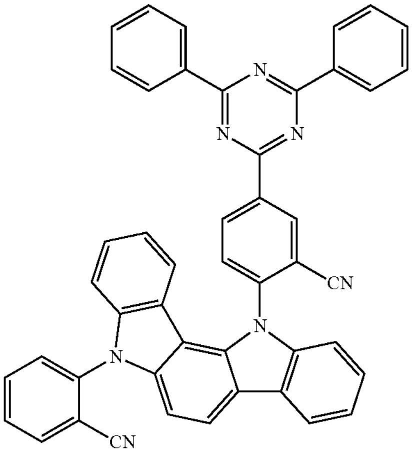
2-66
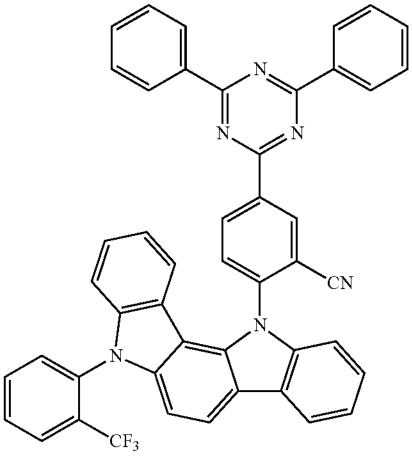
2-67
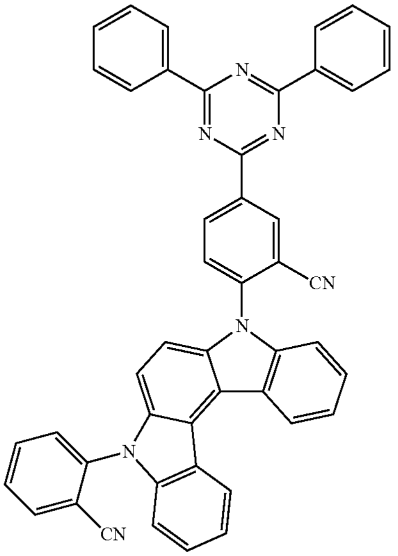

-continued
2-68
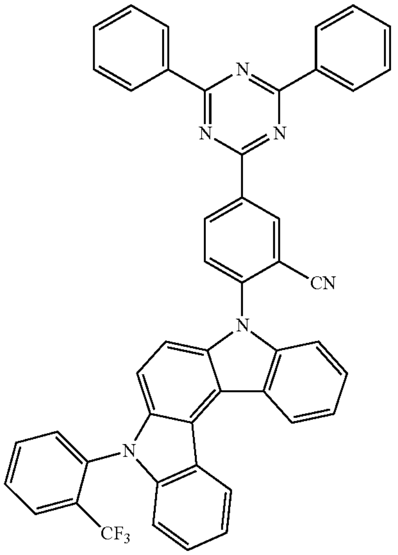
2-69
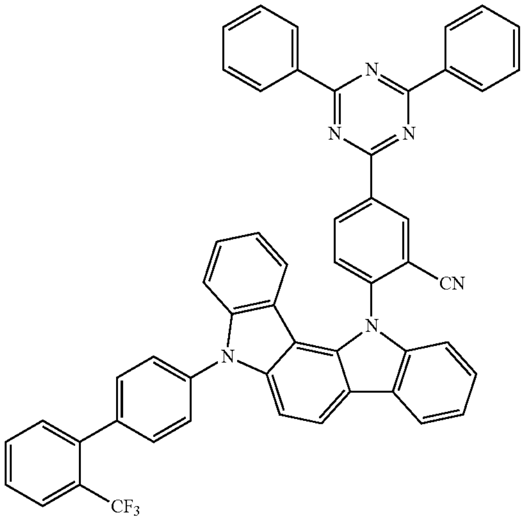
2-70
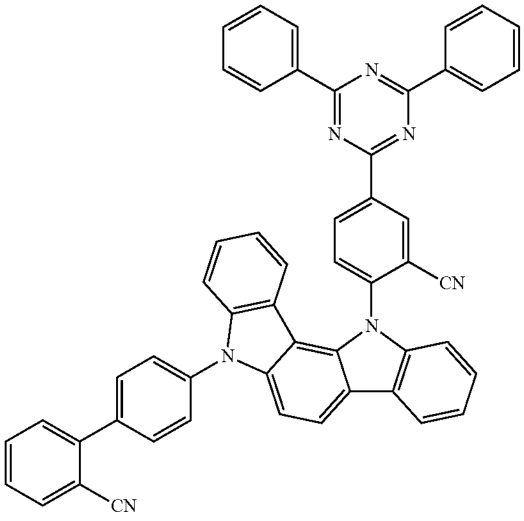
-continued
2-71
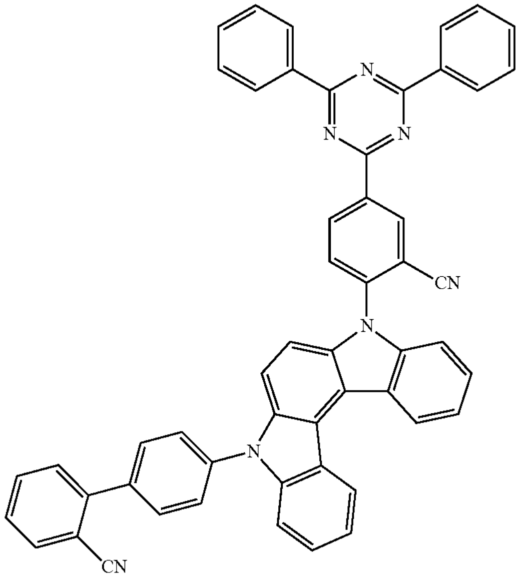
2-72
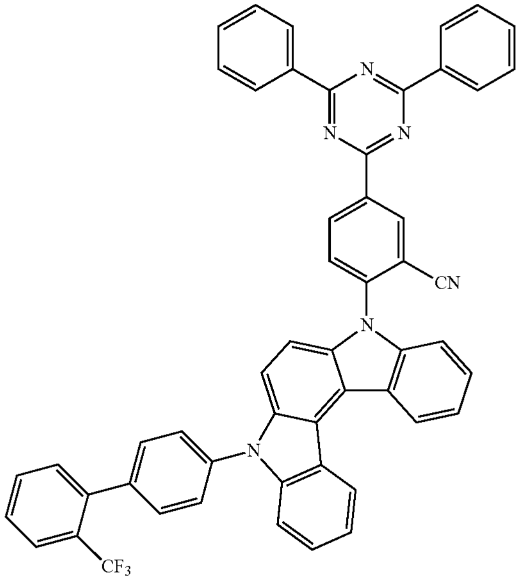

-continued
2-73
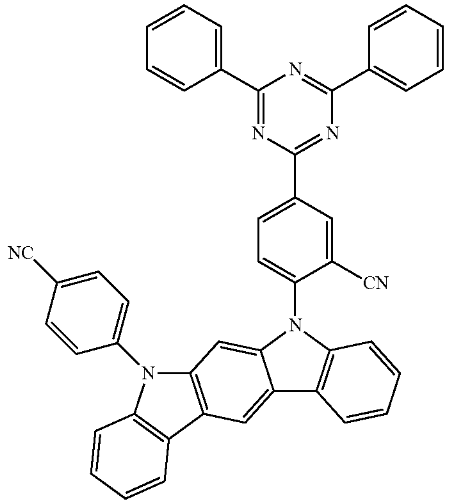
2-74
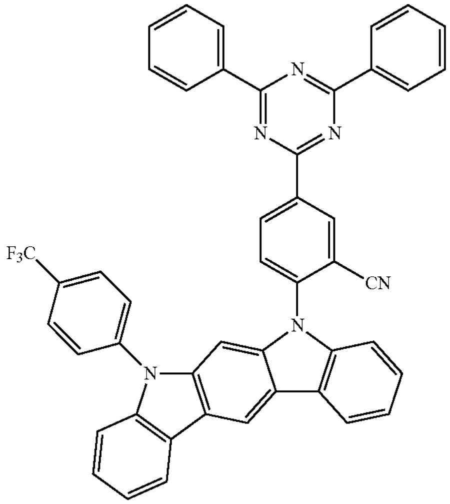
2-75
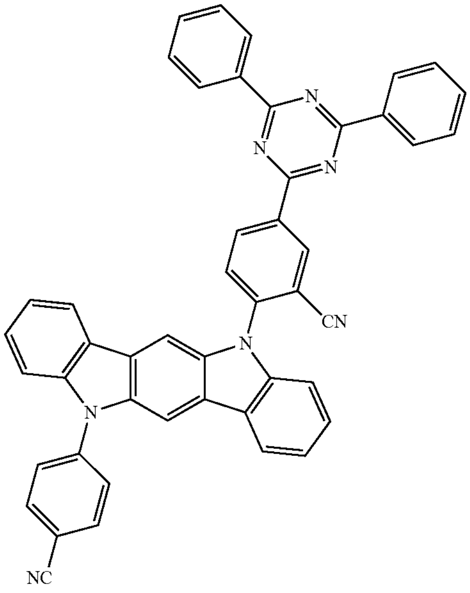
-continued
2-76
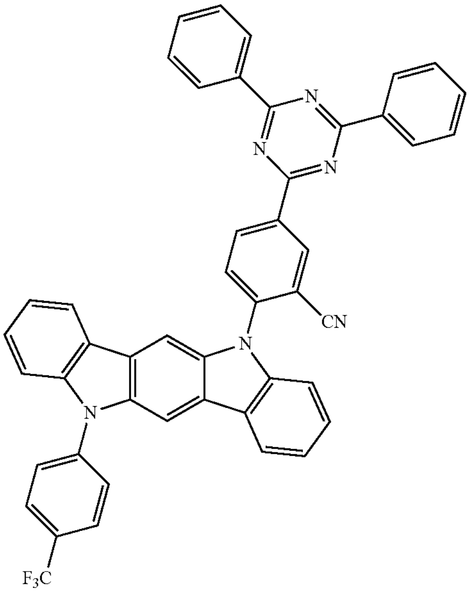
2-77
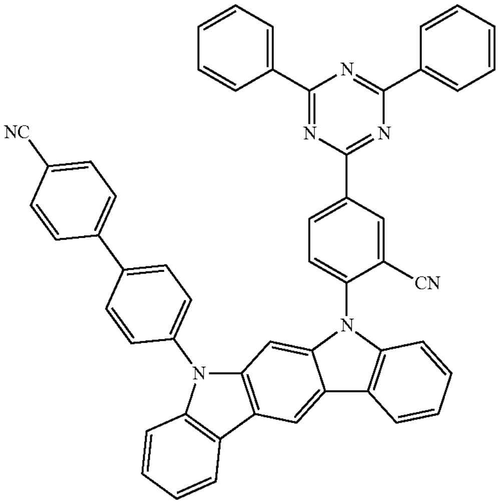

-continued
2-78
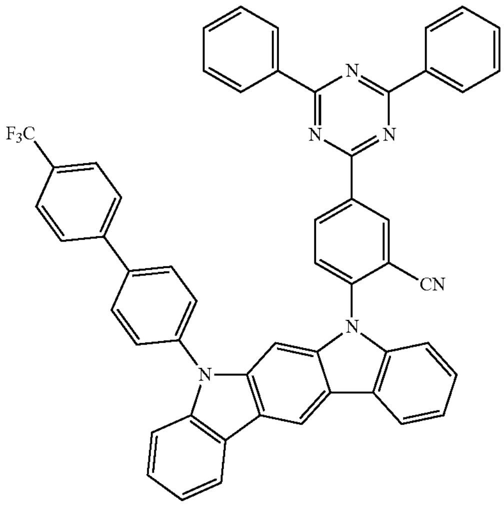
2-79
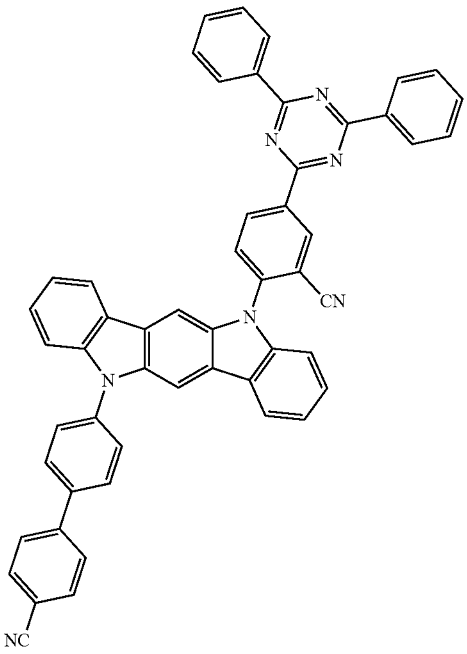
-continued
2-80
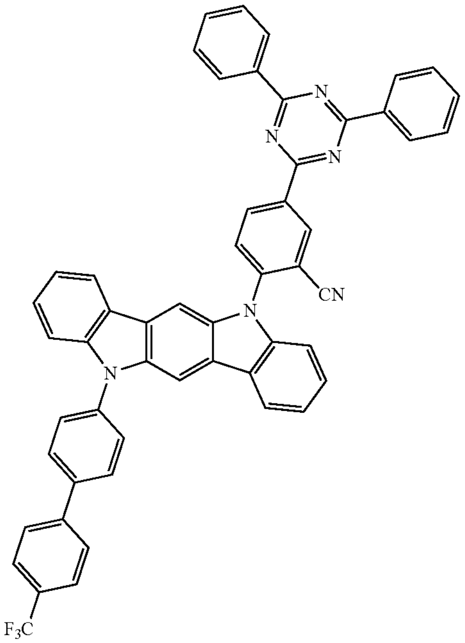
2-81
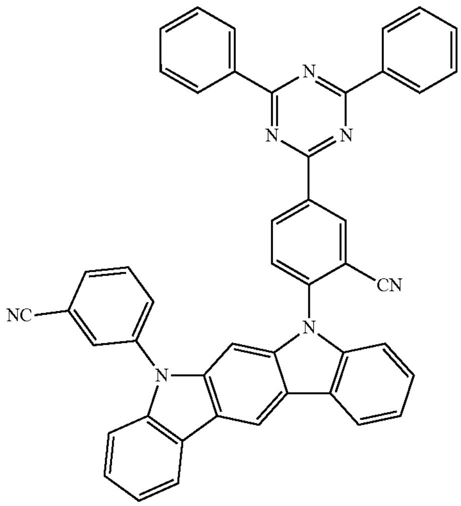
2-82
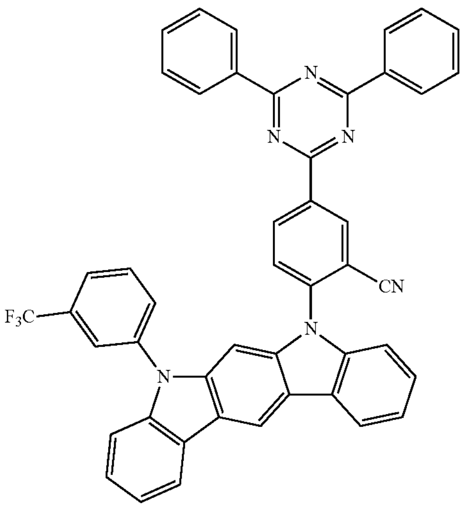

-continued
2-83
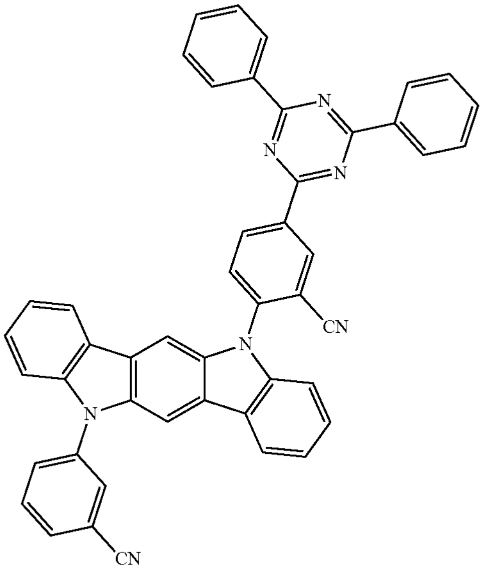
2-84
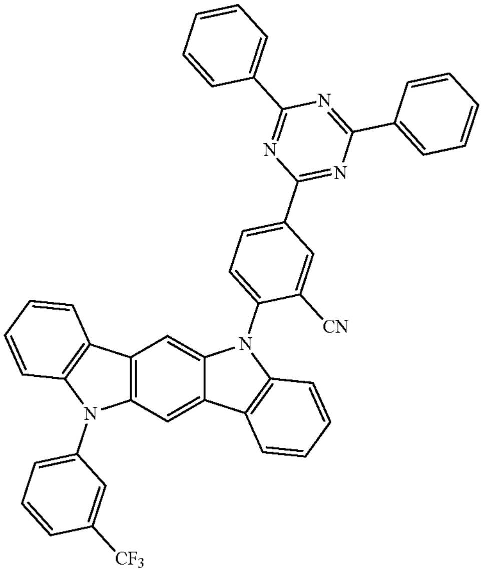
-continued
2-85
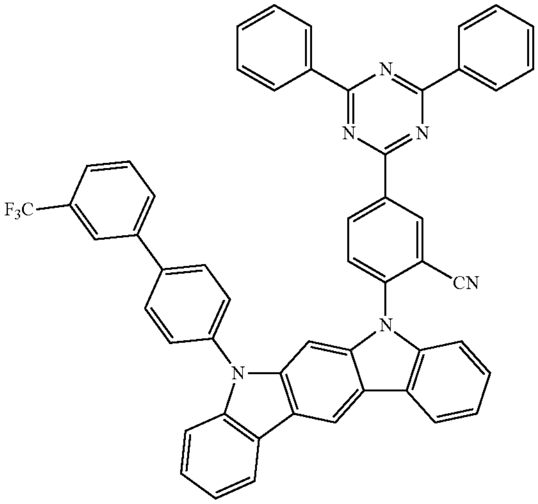
2-86
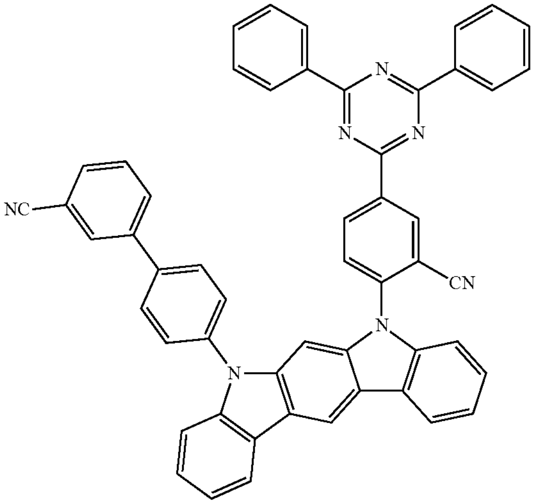

-continued
2-87
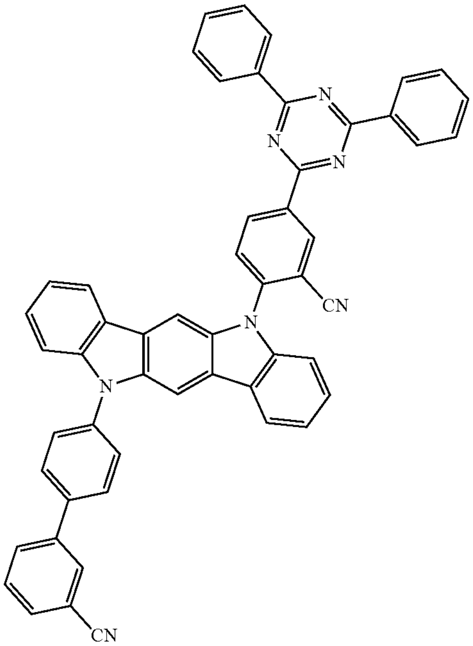
2-88
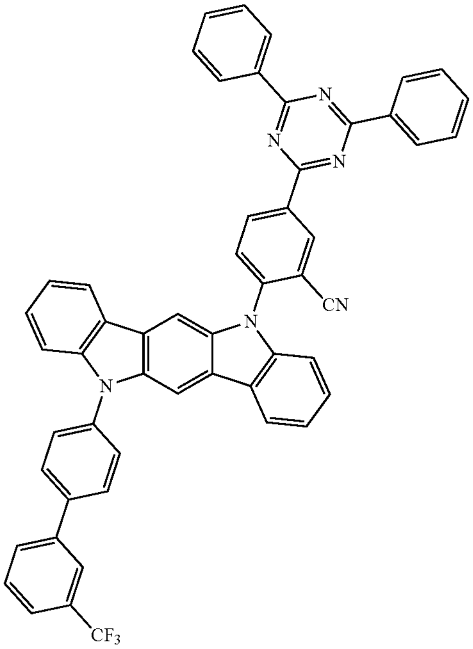
-continued
2-89
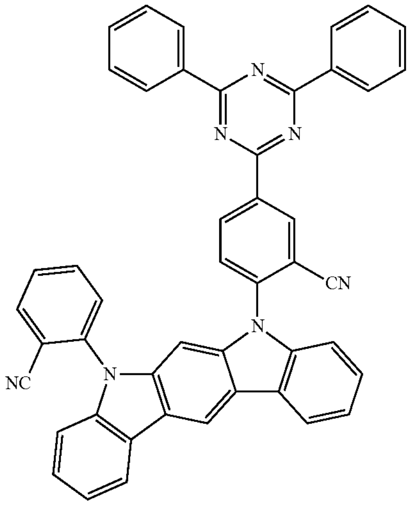
2-90
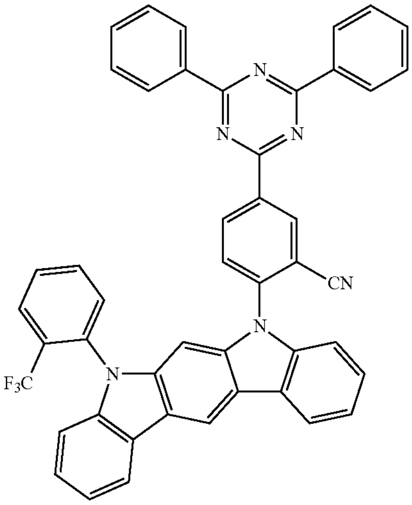
2-91
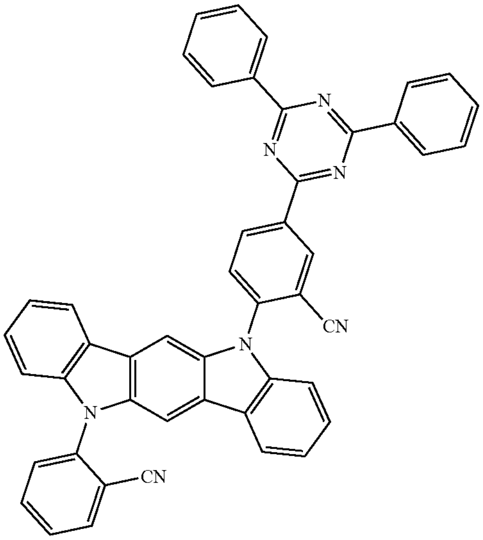

2-92
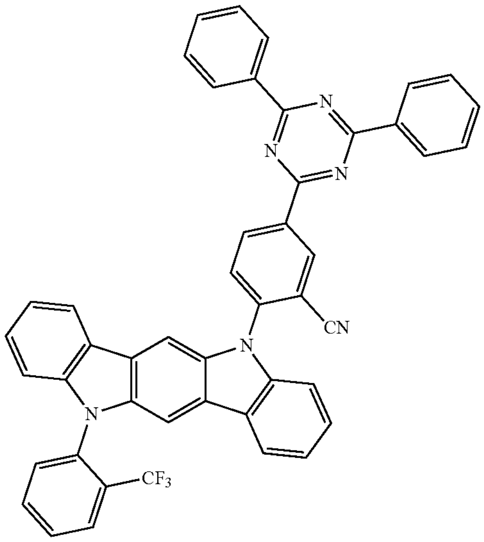
2-93
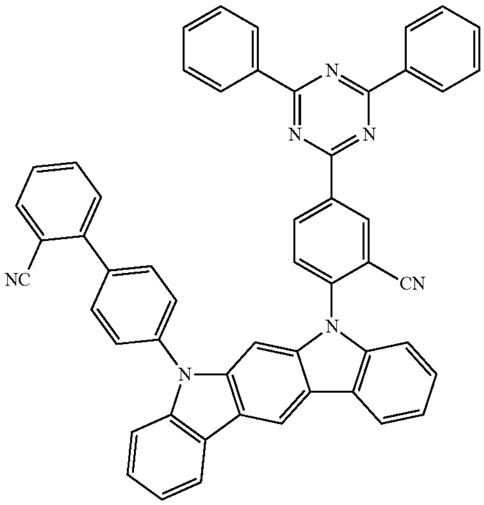
2-94
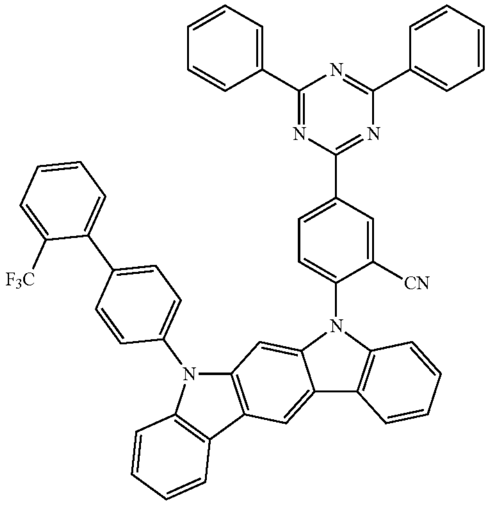
2-95
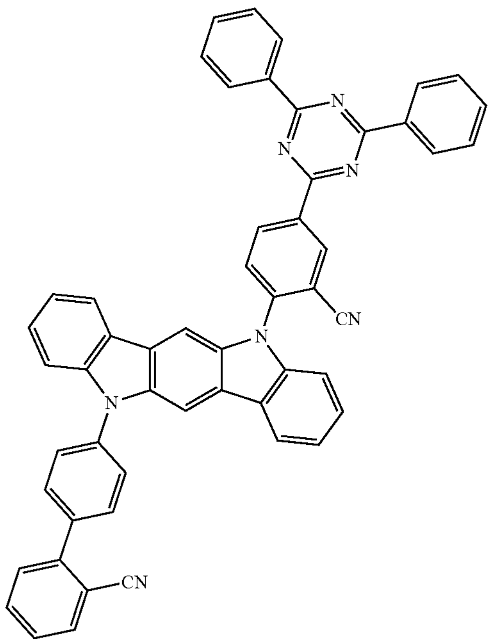
2-96
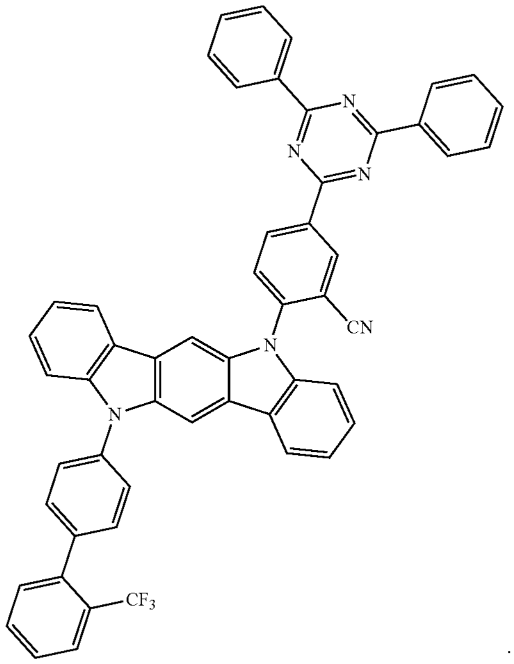
2. The organic light emitting diode according to claim 1, wherein the first compound is one of compounds in Formula 3:

[Formula 3]
1-1
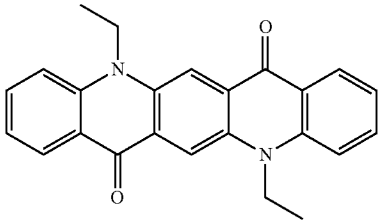
1-2
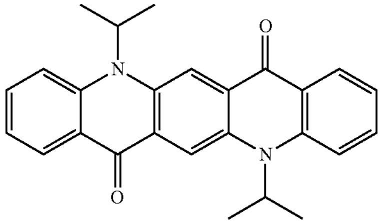
1-3
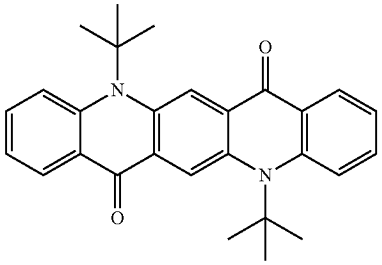
1-4
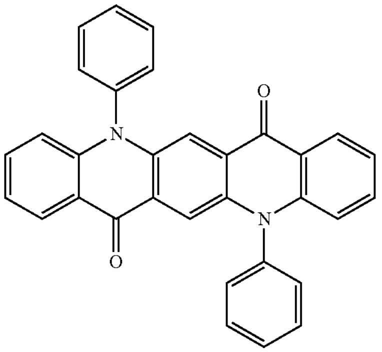
1-5
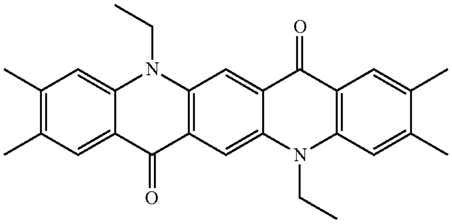
1-6
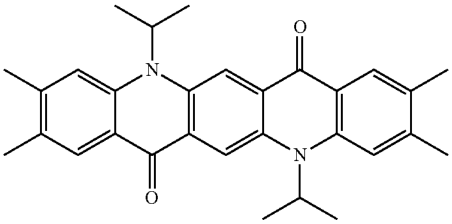
-continued
1-7
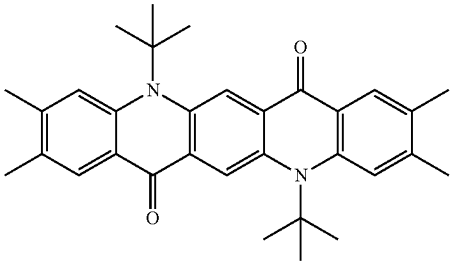
1-8
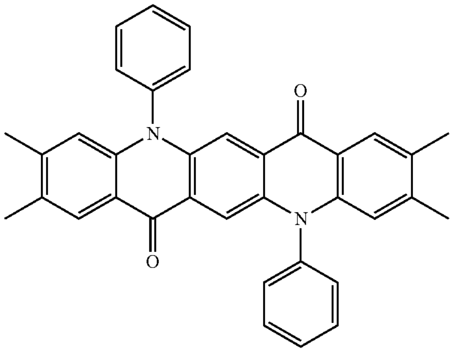
1-9
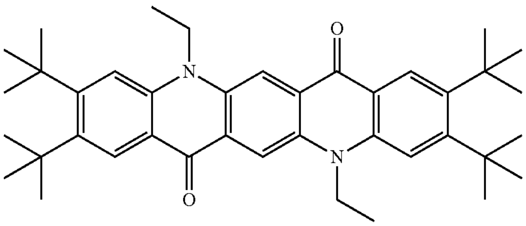
1-10
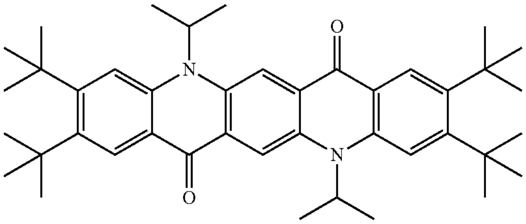
1-11
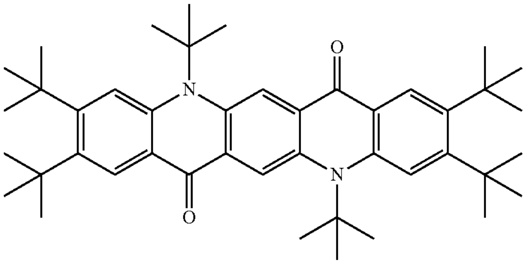

-continued 1-12

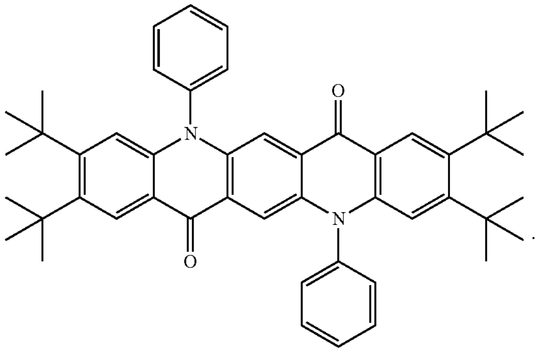

3. The organic light emitting diode according to claim 1, wherein an overlap ratio between an absorption spectrum of the first compound and an emission spectrum of the second compound is equal to or greater than 35%.

4. The organic light emitting diode according to claim 1, wherein a weight % of the second compound is greater than a weight % of the first compound.

5. The organic light emitting diode according to claim 1, wherein the first emitting material layer further includes a first host.

6. The organic light emitting diode according to claim 1, wherein the first emitting material layer includes a first layer and a second layer, and the second layer is positioned between the first layer and the second electrode, and wherein the first layer includes the first compound and a first host, and the second layer includes the second compound and a second host.

7. The organic light emitting diode according to claim 6, wherein the first emitting material layer further includes a third layer including the first compound and a third host and positioned between the second layer and the second electrode.

8. The organic light emitting diode according to claim 7, further comprising:

a hole blocking layer between the second electrode and the third layer, wherein the third host is same as a material of the hole blocking layer.

9. The organic light emitting diode according to claim 6, further comprising:

an electron blocking layer between the first electrode and the first layer, wherein the first host is same as a material of the electron blocking layer.

10. The organic light emitting diode according to claim 1, wherein the first emitting material layer includes a first layer and a second layer, and the second layer is positioned between the first layer and the first electrode, and wherein the first layer includes the second compound and a first host, and the second layer includes the first compound and a second host.

11. The organic light emitting diode according to claim 10, further comprising:

a hole blocking layer between the second electrode and the second layer, wherein the first host is same as a material of the hole blocking layer.

12. The organic light emitting diode according to claim 1, further comprising:

a second material layer between the first electrode and the first emitting material layer; and a charge generation layer between the first emitting material layer and the second emitting material layer, wherein the second emitting material layer is one of a red emitting material layer, a green emitting material layer and a third emitting material layer.

13. An organic light emitting display device, comprising:

a substrate;

the organic light emitting diode of claim 1 over the substrate; and an encapsulation film covering the organic light emitting diode.

14. The organic light emitting display device according to claim 13, wherein the encapsulation film includes a first inorganic insulating layer, an organic insulating layer and a second inorganic insulating layer.

* * * * *